(12) United States Patent
Reategui et al.

(10) Patent No.: US 9,427,408 B2
(45) Date of Patent: Aug. 30, 2016

(54) SILICA-MATRIX FORMING COMPOSITIONS, MATERIALS FORMED THEREFROM, AND METHODS OF USING THE SAME

(71) Applicants: Eduardo Reategui, Minneapolis, MN (US); Lisa Kasinkas, Minneapolis, MN (US); Alptekin Aksan, Minneapolis, MN (US)

(72) Inventors: Eduardo Reategui, Minneapolis, MN (US); Lisa Kasinkas, Minneapolis, MN (US); Alptekin Aksan, Minneapolis, MN (US)

(73) Assignees: Lisa Kasinkas, Minneapolis, MN (US); Eduardo Reategui, Revere, MA (US); Alptekin Aksan, Minneapolis, MN (US)

( * ) Notice: Subject to any disclaimer, the term of this patent is extended or adjusted under 35 U.S.C. 154(b) by 0 days.

(21) Appl. No.: 14/355,341

(22) PCT Filed: Nov. 7, 2012

(86) PCT No.: PCT/US2012/063960
§ 371 (c)(1),
(2) Date: Apr. 30, 2014

(87) PCT Pub. No.: WO2013/070778
PCT Pub. Date: May 16, 2013

(65) Prior Publication Data
US 2014/0302130 A1    Oct. 9, 2014

Related U.S. Application Data

(60) Provisional application No. 61/556,631, filed on Nov. 7, 2011.

(51) Int. Cl.
| | |
|---|---|
| A61K 9/48 | (2006.01) |
| B82Y 5/00 | (2011.01) |
| C12N 5/00 | (2006.01) |
| C12N 11/14 | (2006.01) |
| A61K 35/12 | (2015.01) |
| A61K 35/13 | (2015.01) |

(52) U.S. Cl.
CPC ............. *A61K 9/4816* (2013.01); *A61K 35/12* (2013.01); *A61K 35/13* (2013.01); *C12N 5/0068* (2013.01); *C12N 11/14* (2013.01); *C12N 2533/12* (2013.01)

(58) Field of Classification Search
CPC .................................. A61K 9/48; B82Y 5/00
USPC ......................................... 424/451; 977/721
See application file for complete search history.

(56) References Cited

U.S. PATENT DOCUMENTS

| | | | |
|---|---|---|---|
| 4,148,689 | A | 4/1979 | Hino et al. |
| 4,391,909 | A | 7/1983 | Lim |
| 5,200,334 | A | 4/1993 | Dunn et al. |
| 5,229,096 | A | 7/1993 | Cohen |
| 5,508,193 | A | 4/1996 | Mandelbaum et al. |
| 5,693,513 | A | 12/1997 | Pope |
| 5,739,020 | A | 4/1998 | Pope |
| 6,214,593 | B1 | 4/2001 | Carturan et al. |
| 6,248,321 | B1 | 6/2001 | Winder et al. |
| 6,284,522 | B1 | 9/2001 | Wackett et al. |
| 6,303,290 | B1 | 10/2001 | Liu |
| 6,369,299 | B1 | 4/2002 | Sadowsky et al. |
| 6,495,352 | B1 | 12/2002 | Brinker et al. |
| 6,673,582 | B2 | 1/2004 | McTavish |
| 6,825,001 | B2 | 11/2004 | Wackett et al. |
| 7,052,913 | B2 | 5/2006 | Babich et al. |
| 7,510,656 | B2 | 3/2009 | Shafer et al. |
| 2001/0055797 | A1 | 12/2001 | Conroy |
| 2005/0095690 | A1 | 5/2005 | Naik et al. |
| 2006/0171990 | A1 | 8/2006 | Asgari |
| 2009/0300745 | A1 | 12/2009 | Dispensa |
| 2010/0190666 | A1 | 7/2010 | Ali et al. |
| 2014/0051144 | A1 | 2/2014 | Wackett et al. |

FOREIGN PATENT DOCUMENTS

| | | |
|---|---|---|
| WO | WO-2007129991 A1 | 11/2007 |
| WO | WO-2011011468 A2 | 5/2011 |
| WO | WO-2012116013 A2 | 8/2012 |
| WO | WO-2013070778 A1 | 5/2013 |

OTHER PUBLICATIONS

"International Application Serial No. PCT/US2012/026031, International Preliminary Report on Patentability mailed Mar. 27, 2014", 7 pgs.
"International Application Serial No. PCT/US2012/026031, International Search Report mailed Jun. 6, 2012", 2 pgs.
"International Application Serial No. PCT/US2012/026031, Written Opinion mailed Jun. 6, 2012", 5 pgs.
"International Application Serial No. PCT/US2012/063960, International Search Report mailed Jan. 23, 2013", 4 pgs.
"International Application Serial No. PCT/US2012/063960, Written Opinion mailed Jan. 23, 2013", 8 pgs.

(Continued)

*Primary Examiner* — Yan Xiao
(74) *Attorney, Agent, or Firm* — Fredrikson & Byron, P.A.

(57) ABSTRACT

The present invention provides compositions for encapsulation of biomaterials in a silica-matrix. The present invention also provides methods of making silica-matrix encapsulated biomaterials, and to methods of using silica-matrix encapsulated biomaterials. In one embodiment, the present invention provides a method of encapsulating mammalian cells in a silica-matrix while maintaining metabolic activity. In another embodiment, the present invention provides a method of purifying cancer cells using a silica-matrix.

14 Claims, 34 Drawing Sheets

(56) References Cited

OTHER PUBLICATIONS

"Russian Application Serial No. 2013142684, Office Action mailed Nov. 28, 2013", 4 pgs.

"Science in Action:Hydraulic Fracturing Research Study", U.S. Environmental Protection Agency (EPA) Office of Research and Development, Document No. EPA/600/F-10/002, (Jun. 2010), 2 pgs.

Brinker, C. J, et al., "Sol-Gel Science: The Physics and Chemistry of Sol-Gel Processing", Pgs. from Chapter 3: Hydrolysis and Condensation II-Silicates, Academic Press, Inc. San Diego, CA, (1990), 99-107.

Dickson, D J, et al., "Photobiological hydrogen production from *Synechocystis* sp. PCC 6803 encapsulated in silica sol-gel", International Journal of Hydrogen Energy, Elsivier Science Publishers B. V. Banking, GB vol. 34, No. 1, (Jan. 1, 2009), 204-215.

Ho, C, et al., "Enzymatic Properties of Atrazine Chlorohydrolase Entrapped in Biomimetic Silica", Journal of Applied Biological Chemistry, 51(4), (2008), 143-147.

Kauffmann, C., et al., "Entrapment of atrazine chlorohydrolase in sol-gel glass matrix", Journal of Biotechnology, 62, (1998), 169-176.

Kauffmann, C., et al., "Entrapment of atrazine chlorohydrolase in sol-gel glass matrix", Journal of Biotechnology, 62(3), (1998), 169-176.

Kauffmann, C., et al., "Novel Methodology for Enzymatic Removal of Atrazine from Water by CBD-Fusion Protein Immobilized on Cellulose", Environ. Sci. Technol., 34, (2000), 1292-1296.

Kirby, J. R, "Designer bacteria degrades toxin", Nat Chem Biol., 6(6), (Jun. 2010), 398-9.

Ma, T., et al., "Enhancement of atrazine degradation by crude and immobilized enzymes in two agricultural soils", Environ Earth Sci., Online Publication, (2011), 7 pgs.

Ma, Y., et al., "The Research of Immobilized Atrazine Degrading Bacteria Degrading Characteristics", International Conference on Environmental Science and Information Application Technology, 2009. ESIAT 2009, vol. 1, (2009), 677-680.

Macias-Flores, A., et al., "Atrazine biodegradation by a bacterial community immobilized in two types of packed-bed biofilm reactors", World J Microbiol Biotechnol., 25, (2009), 2195-2204.

Mantsch, H. H, et al., "Infrared Spectroscopy of Biomolecules", Pg. from Chapter 9, Section 9.7.2.1, Wily-Liss, Inc., New York, (1996), 266.

Meunier, C F, et al., "Encapsulation of cells within silica matrixes: Towards a new advance in the conception of living hybrid materials", Journal of Colloid and Interface Science, Acadamic Press, New York, NY, US, vol. 342, No. 2, (Feb. 15, 2010), 211-224.

Nedovic, V., et al., Fundamentals of Cell Immobilization Biotechnology, Adapted from p. 15, Part 1, 15.

Reategui, E., et al., "Encapsulation of Mammalian Cells in Hybrid Inorganic Matrices for Developing Bio-detection Applications", Alley Conference 2010, Poster, (2010).

Reategui, E., et al., "Silica gel-encapsulated AtzA biocatalyst for atrazine biodegradation", Appl Microbiol Biotechnol., [Epub ahead of print], (Jan. 7, 2012), 10 pgs.

Reetz, Manfred T., "Chapter 6—Practical Protocols for Lipase Immobilization", Immobilization of Enzymes and Cells, Second Edition—Edited by Jose M. Guisan, (2006), 66.

Riddle, Kathryn W, et al., "Biomaterials for Cell Immobilization: A look at carrier design", Kathryn W. Riddle and David J. Mooney University of Michigan, Chemical Engineering, 19 pages.

Ruiz-Hitzky, Eduardo, et al., "An Introduction to Bio-nanohybrid Materials", Bio-inorganic Hybrid Nanomaterials, Edited by Eduardo Ruiz-Hitzky, Katsuhiko Ariga and Yuri Lvov, (2008), 1.

Shona, Pek Y, et al., "A thixotropic nanocomposite gel for three-dimensional cell culture", Nature Nanotechnology vol. 3, No. 11, (Sep. 28, 2008), 671-675.

Siripattanakul, S., et al., "Atrazine removal in agricultural infiltrate by bioaugmented polyvinyl alcohol immobilized and free Agrobacterium radiobacter J14a: A sand column study", Chemosphere, 74, (2009), 308-313.

Tafoya-Garnica, A., et al., "Kinetics of atrazine biodegradation by suspended and immobilized mixed microbial cells cultivated in continuous systems", Journal of Chemical Technology & Biotechnology, 84(7), (Jul. 2009), 982-991.

Vivek, Kandimalla, et al., "Immobilization of Biomolecules in Sol-Gels Biological and Analytical Applications", Critical Reiviews in Analytical Chemistry, vol. 36, No. 2, (Jul. 1, 2006), 73-106.

Wright, J. D, "Sol-Gel Materials: Chemistry and Applications", Chapter 2: Silica Sol-Gels: Reaction Mechanisms, Gordon and Breach Science Publishers, (2001), 15-31.

Yu, M., et al., "RNA sequencing of pancreatic circulating tumour cells implicates WNT signalling in metastasis", Nature, 487(7408), (2012), 510-515.

FIG. 12A  FIG. 12B
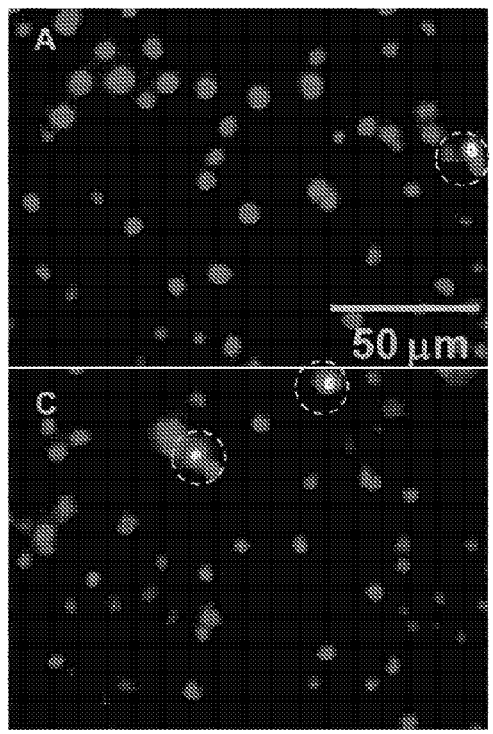
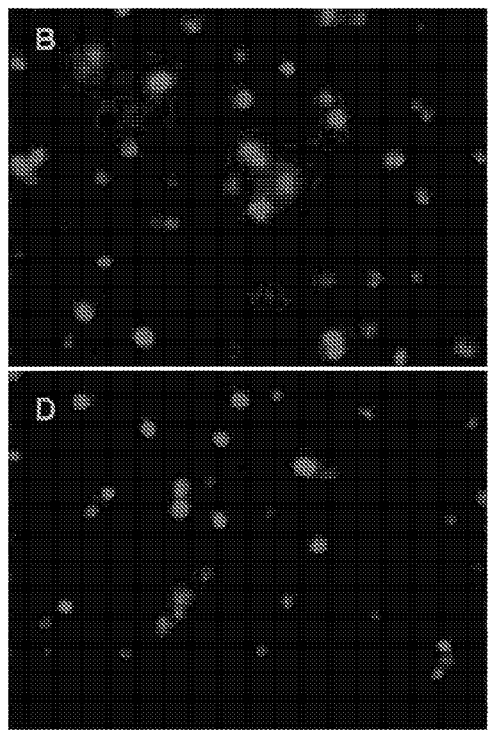
FIG. 12C  FIG. 12D
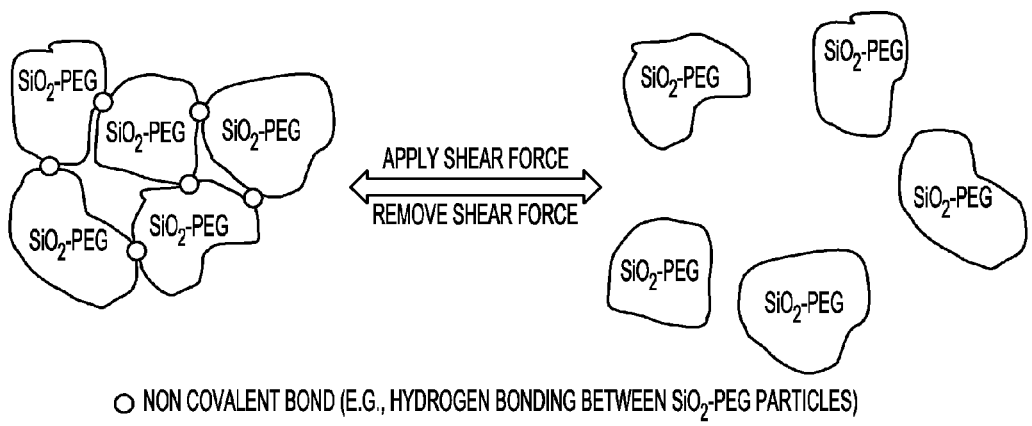
○ NON COVALENT BOND (E.G., HYDROGEN BONDING BETWEEN SiO$_2$-PEG PARTICLES)
FIG. 13

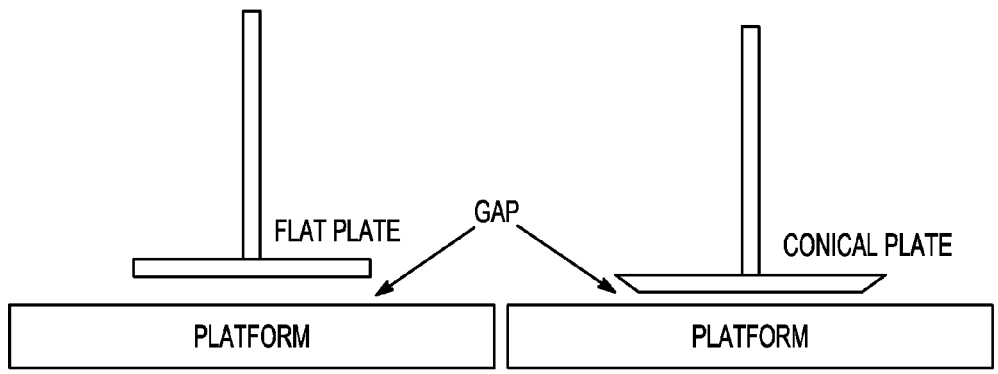
FIG. 14
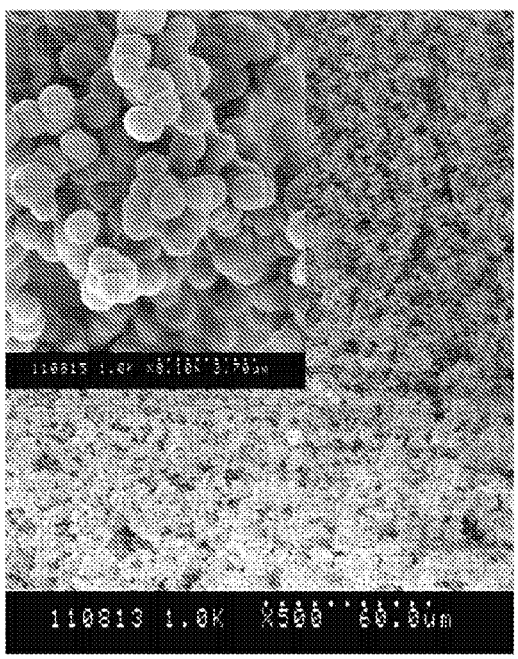  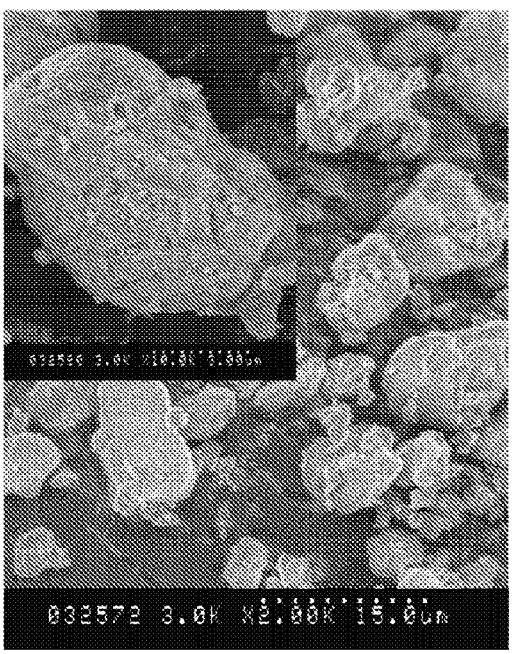
FIG. 15A          FIG. 15B

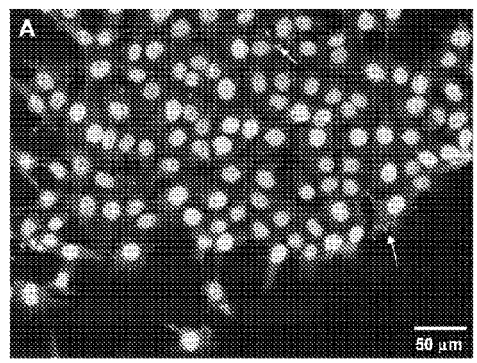
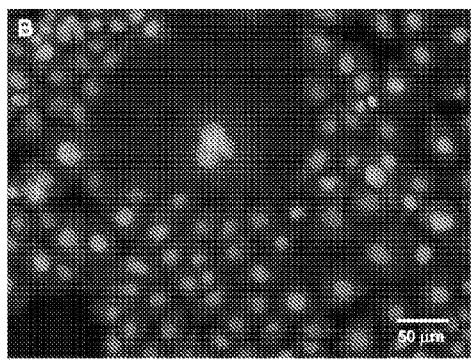
FIG. 23A                FIG. 23B
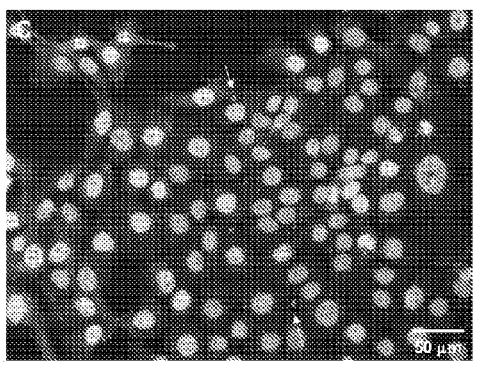
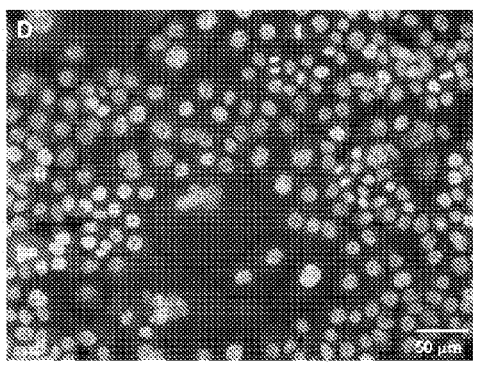
FIG. 23C                FIG. 23D

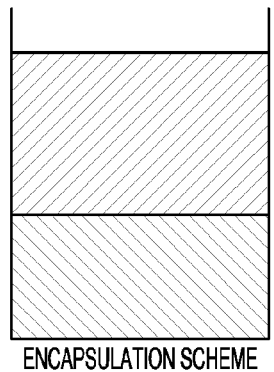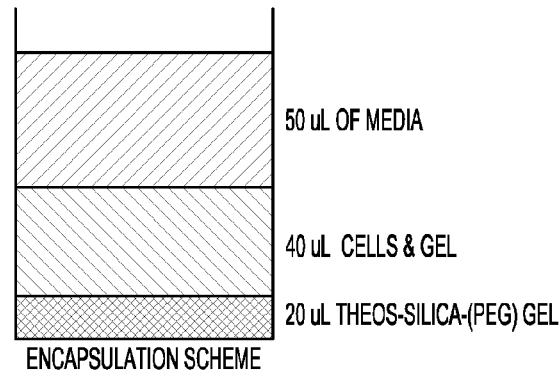
FIG. 25A  FIG. 25B
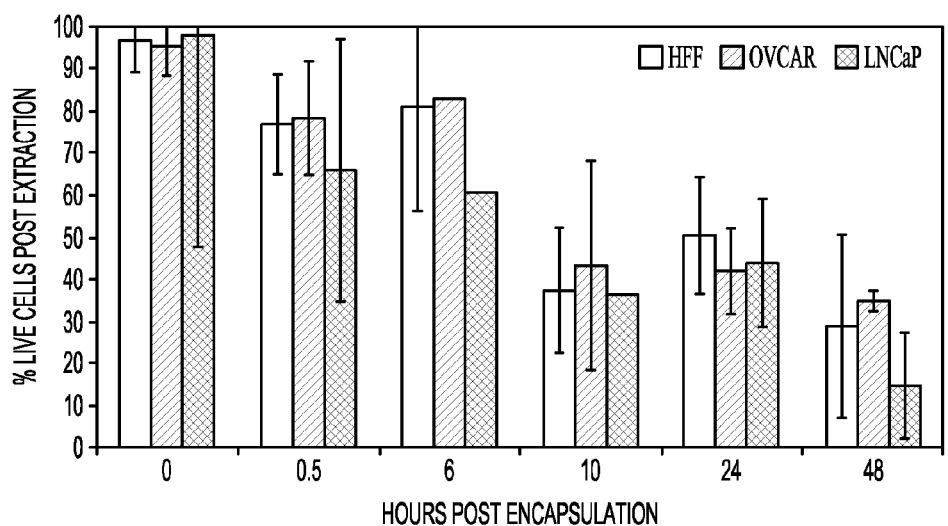
FIG. 26

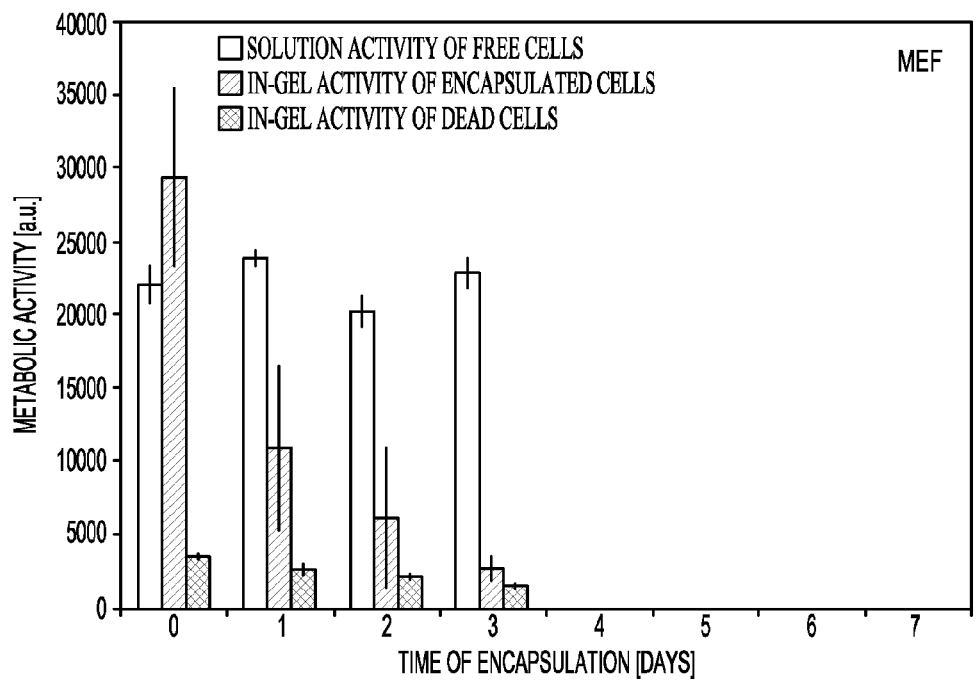
FIG. 37B1
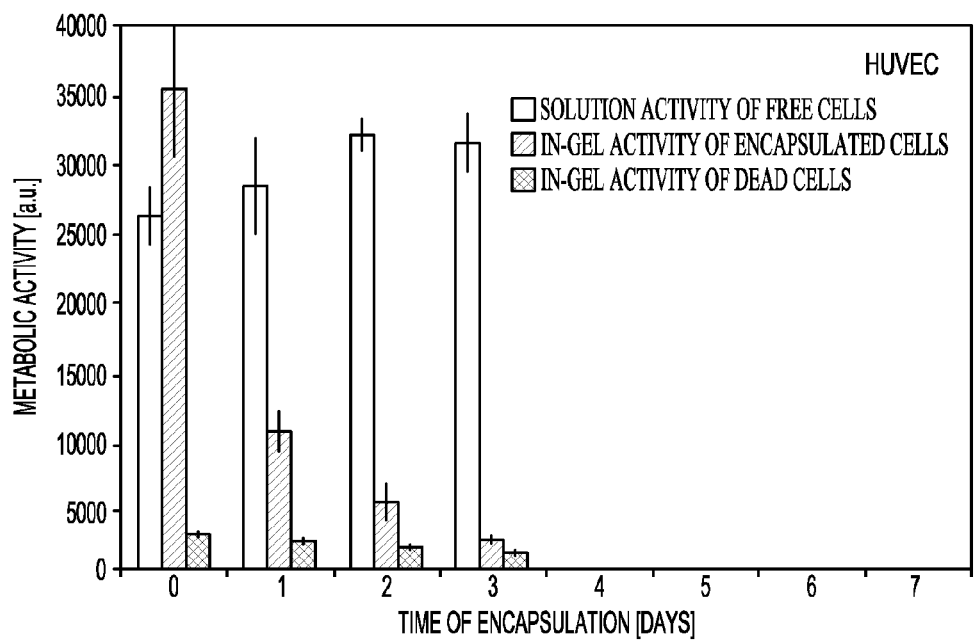
FIG. 37B2

SILICA-MATRIX FORMING COMPOSITIONS, MATERIALS FORMED THEREFROM, AND METHODS OF USING THE SAME

CLAIM OF PRIORITY

This patent application is a U.S. National Stage Filing under 35 U.S.C. 371 from International Application No. PCT/US2012/063960, filed on 7 Nov 2012, and published as WO 2013/070778 A1 on 16 May 2013, which claims the benefit of priority, under 35 U.S.C. Section 119(e), to U.S. Provisional Patent Application Serial Number 61/556,631, filed on Nov. 7, 2011, which are hereby incorporated by reference herein in its entirety.

STATEMENT OF GOVERNMENT SUPPORT

This invention was made with government support under grant number 0644784 awarded by the National Science Foundation (NSF). The government has certain rights in this invention.

BACKGROUND OF THE INVENTION

In tumors, not only there are cancer cells of different phenotypes, but there are also normal cells (e.g., fibroblasts, myoblasts, endothelial cells, epithelial cells, and stromal cells). This makes detecting or isolating cancer cells from tumor specimens and biopsies an extremely time-consuming process since all cell types usually grow together in the culture environment. Therefore, researchers who work with isolated cancer cell lines use special isolation processes. However, these processes are very intricate and time-consuming, requiring repetitive processing of the cells over time.

Biomaterials often exhibit properties that can have utility in a wide variety of applications. The metabolic functionality of biomaterials can have extensive applications in biotechnology (e.g., biosensing, biocatalysis, bioremediation, and photobioreactors), medicine (e.g., regenerative medicine, tissue engineering, and recombinant protein production), and in new hybrid materials with improved functional and structural properties.

Many problems have been experienced in immobilization or isolation of biomaterials or cancer cells. For example, when immobilizing cells using silica nanoparticles, there could be detrimental interactions between the silica surface and the cell membranes. The silica surface interactions can damage the cells. When proteins and enzymes are encapsulated in the gels, they can get adsorbed onto the gel, which can cause denaturation and aggregation of the absorbed proteins and therefore loss of structure and catalytic activity. In some examples, immobilization or isolation of cells can cause cell death.

SUMMARY OF THE INVENTION

In various embodiments, the present invention provides a silica-matrix encapsulated biomaterial, including a reaction product of a mixture. The mixture includes a reactive silicon compound. The mixture also includes a biomaterial including at least one cell that includes a non-cancerous mammalian cell or a cancerous mammalian cell. The at least one cell has a metabolic activity before it is encapsulated in the silica-matrix. After formation of the silica-matrix encapsulated biomaterial, the at least one cell at least partially retains its metabolic activity.

In various embodiments, the present invention provides a method for formation of a silica-matrix encapsulated biomaterial. The method includes forming a silica-matrix encapsulated biomaterial. The silica-matrix encapsulated biomaterial includes the reaction product of a mixture. The mixture includes a reactive silicon compound. The mixture also includes a biomaterial including at least one cell including a non-cancerous mammalian cell or a cancerous mammalian cell. The at least one cell has a metabolic activity before it is encapsulated in the silica-matrix. After formation of the silica-matrix encapsulated biomaterial, the at least one cell at least partially retains its metabolic activity.

In various embodiments, the present invention provides a method of generating cancerous cells substantially free of non-cancerous cells. The method includes forming a silica-matrix encapsulated biomaterial. The silica-matrix encapsulated biomaterial includes the reaction product of a mixture. The mixture includes a reactive silicon compound. The mixture also includes a biomaterial including at least one living cancerous mammalian cell, and at least one living non-cancerous mammalian cell. After forming the silica-matrix encapsulated biomaterial, the at least one non-cancerous cell dies, and the at least one cancerous cell survives. The method also includes removing the at least one cancerous cell from the silica-matrix.

In various embodiments, the present invention provides a method of selectively purifying cancerous cells. The method includes forming a silica-matrix encapsulated biomaterial. The silica-matrix encapsulated biomaterial includes the reaction product of a mixture. The mixture includes a reactive silicon compound. The mixture also includes a biomaterial including at least one living cancerous mammalian cell, and at least one living non-cancerous mammalian cell. After forming the silica-matrix encapsulated biomaterial, the at least one non-cancerous cell dies, and the at least one cancerous cell survives. The method also includes removing the at least one cancerous cell from the silica-matrix.

In various embodiments, the present invention provides a method of selectively purifying cancerous cells. The method includes forming a silica-matrix encapsulated biomaterial. The silica-matrix encapsulated biomaterial includes the reaction product of a mixture. The mixture includes a reactive silicon compound. The mixture also includes a biomaterial including at least one first living cancerous mammalian cell and at least one second living cancerous mammalian cell. The first living cancerous mammalian cell and the second living cancerous mammalian cell have different phenotypes. After forming the silica-matrix encapsulated biomaterial, the at least one first cancerous cell dies, and the at least one second cancerous cell survives. The method also includes removing the at least one second cancerous cell from the silica-matrix.

Various embodiments of the present invention provide certain advantages over other compositions for formation of silica-matrix encapsulated biomaterials and methods of using the same. In some embodiments, the composition allows a higher rate of cell survival within the silica-matrix than other methods. For example, some embodiments have a higher rate of mammalian cell survival than other methods. In some embodiments, the composition allows isolation of cancerous cells more efficiently or more easily than other methods. For example, some embodiments allow isolation of cancerous cells in a more facile manner, or at lower cost, than other methods. In some embodiments, the encapsulated cells can be removed from the silica more easily than other methods, for example by using non-chemical methods such as mechanical removal of cells from a thixotropic gel. In some embodiments, wherein the biomaterial includes both cancerous cells and non-cancerous cells, the composition can allow formation of a silica-matrix wherein the non-cancerous cells have a significantly lower survival rate than the cancerous cells, as compared to other methods. In some embodiments, the method of separation of cancerous cells is not based on epithelial cell adhesion/activating molecule (EpCAM) expression on the surface of the cell, as with other methods, but rather is based on biological differences between cancerous cells and normal cells, such as the differences in transduction responses.

BRIEF DESCRIPTION OF THE FIGURES

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

The patent or application file contains at least one drawing executed in color. Copies of this patent or patent application publication with color drawing(s) will be provided by the Office upon request and payment of the necessary fee.

FIG. 12 illustrates fluorescence microscopy micrographs of encapsulated cells, in accordance with various embodiments.

FIG. 13 illustrates a thixotropic transition, in accordance with various embodiments.

FIG. 14 illustrates a rheometer set up for different type of measurements, in accordance with various embodiments.

FIGS. 15 (A) and (B) illustrate SEM images of gels (A) formed of sphere-like particle aggregates, (B) formed of heterogeneous particles, in accordance with various embodiments.

FIG. 19 (B) illustrates cells released from gel, in accordance with various embodiments.

FIG. 19 (C) illustrates membrane integrity of the extracted versus time points, in accordance with various embodiments.

FIGS. 19 (D), (E), and (F) illustrate fluorescence image of extracted cells, control cells, and negative control cells, respectively, in accordance with various embodiments.

FIGS. 23 (A), (B), (C), and (D) illustrate illustrates recovered OVCAR-5 cells after encapsulation of HFF: OVCAR-5 mixed cell population, in accordance with various embodiments.

FIG. 25(A) illustrates an encapsulation scheme that can be used with cells encapsulated in irreversible gels, in accordance with various embodiments.

FIG. 25(B) illustrates an encapsulation scheme that can be used with cells encapsulated in particulated irreversible gels.

FIG. 26 illustrates post-extraction viability of encapsulated cells, in accordance with various embodiments.

FIG. 37(B1) illustrates in-gel metabolic activity of encapsulated MEF cells, in accordance with various embodiments.

FIG. 37(B2) illustrates in-gel metabolic activity of encapsulated HUVEC cells, in accordance with various embodiments.

DETAILED DESCRIPTION OF THE INVENTION

Figure 1:
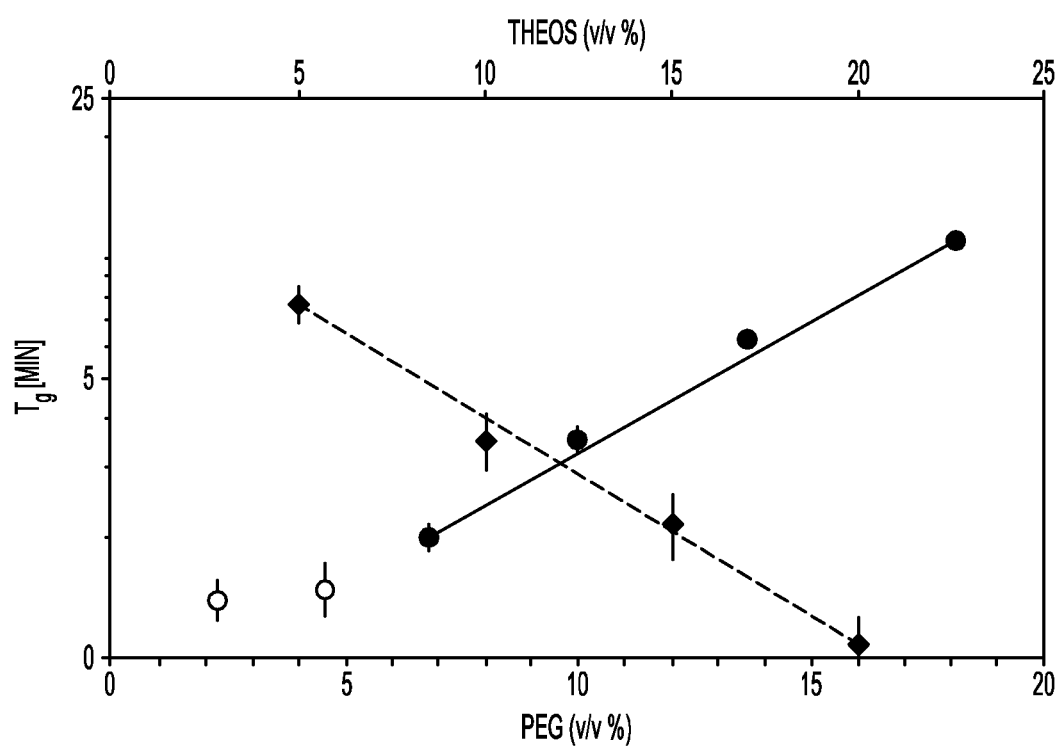
FIG. 1 illustrates gelation times ($T_g$) for gels made with THEOS (10% v/v) and PEG, in accordance with various embodiments.

Reference will now be made in detail to certain claims of the disclosed subject matter, examples of which are illustrated in the accompanying drawings. While the disclosed subject matter will be described in conjunction with the enumerated claims, it will be understood that they are not intended to limit the disclosed subject matter to those claims. On the contrary, the disclosed subject matter is intended to cover all alternatives, modifications, and equivalents, which can be included within the scope of the presently disclosed subject matter as defined by the claims.

References in the specification to "one embodiment," "an embodiment," "an example embodiment," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt % to about 5 wt %, but also the individual concentrations (e.g., 1%, 2%, 3%, and 4%) and the sub-ranges (e.g., 0.5%, 1.1%, 2.2%, 3.3%, and 4.4%) within the indicated range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

Definitions

The term "about" can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

The term "organic group" as used herein refers to but is not limited to any carbon-containing functional group. For example, an oxygen-containing group such as alkoxy groups, aryloxy groups, aralkyloxy groups, oxo(carbonyl) groups, carboxyl groups including carboxylic acids, carboxylates, and carboxylate esters; a sulfur-containing group such as alkyl and aryl sulfide groups; and other heteroatom-containing groups. Non-limiting examples of organic groups include OR', OC(O)N(R')$_2$, CN, CF$_3$, OCF$_3$, R', C(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON (R')$_2$, N(R')SO$_2$R', N(R')SO$_2$N(R')$_2$, N(R')C(O)OR', N(R')C (O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen (in examples that include other carbon atoms) or a carbon-based moiety, and wherein the carbon-based moiety can itself be further substituted; for example, wherein R' can be hydrogen (in examples that include other carbon atoms), alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl, or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J. Examples of organic groups include linear and/or branched groups such as alkyl groups, fully or partially halogen-substituted haloalkyl groups, alkenyl groups, alkynyl groups, aromatic groups, acrylate functional groups, and methacrylate functional groups; and other organic functional groups such as ether groups, cyanate ester groups, ester groups, carboxylate salt groups, and masked isocyano groups. Examples of organic groups include, but are not limited to, alkyl groups such as methyl, ethyl, propyl, isopropyl, n-butyl, s-butyl, and t-butyl groups, acrylate functional groups such as acryloyloxypropyl groups and methacryloyloxypropyl groups; alkenyl groups such as vinyl, allyl, and butenyl groups; alkynyl groups such as ethynyl and propynyl groups; aromatic groups such as phenyl, tolyl, and xylyl groups; cyanoalkyl groups such as cyanoethyl and cyanopropyl groups; halogenated hydrocarbon groups such as 3,3,3-trifluoropropyl, 3-chloropropyl, dichlorophenyl, and 6,6,6,5,5,4,4,3,3-nonafluorohexyl groups; alkenyloxypoly(oxyalkyene) groups such as allyloxy(polyoxyethylene), allyloxypoly(oxypropylene), and allyloxy-poly(oxypropylene)-co-poly(oxyethylene) groups; alkyloxypoly(oxyalkyene) groups such as propyloxy(polyoxyethylene), propyloxypoly(oxypropylene), and propyloxy-poly(oxypropylene)-co-poly(oxyethylene) groups; halogen substituted alkyloxypoly(oxyalkyene) groups such as perfluoropropyloxy(polyoxyethylene), perfluoropropyloxypoly(oxypropylene), and perfluoropropyloxy-poly(oxypropylene)-co-poly(oxyethylene) groups; alkoxy groups such as methoxy, ethoxy, n-propoxy, iso-propoxy, n-butoxy, and ethylhexyloxy groups; aminoalkyl groups such as 3-aminopropyl, 6-aminohexyl, 11-aminoundecyl, 3-(N-allylamino)propyl, N-(2-aminoethyl)-3-aminopropyl, N-(2-aminoethyl)-3-aminoisobutyl, p-aminophenyl, 2-ethylpyridine, and 3-propylpyrrole groups; epoxyalkyl groups such as 3-glycidoxypropyl, 2-(3,4,-epoxycyclohexyl)ethyl, and 5,6-epoxyhexyl groups; ester functional groups such as actetoxyethyl and benzoyloxypropyl groups; hydroxy functional groups such as 2-hydroxyethyl groups; masked isocyanate functional groups such as propyl-t-butylcarbamate, and propylethylcarbamate groups; aldehyde functional groups such as undecanal and butyraldehyde groups; anhydride functional groups such as 3-propyl succinic anhydride and 3-propyl maleic anhydride groups; and metal salts of carboxylic acids such as the zinc, sodium, or potassium salts of 3-carboxypropyl and 2-carboxyethyl.

The term "substituted" as used herein refers to an organic group as defined herein or molecule in which one or more bonds to a hydrogen atom contained therein are replaced by one or more bonds to a non-hydrogen atom. The term "functional group" or "substituent" as used herein refers to a group that can be or is substituted onto a molecule, or onto an organic group. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 or 12-40 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl group are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3$', wherein each R is independently selected, and protonated forms of each, except for —NR$_3$', which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

The terms "halo" or "halogen" or "halide", as used herein, by themselves or as part of another substituent mean, unless otherwise stated, a fluorine, chlorine, bromine, or iodine atom, preferably, fluorine, chlorine, or bromine.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "resin" as used herein refers to polysiloxane material of any viscosity that includes at least one siloxane monomer that is bonded via a Si—O—Si bond to three or four other siloxane monomers. In one example, the polysiloxane material includes T or Q groups, as defined herein.

The term "number-average molecular weight" as used herein refers to the ordinary arithmetic mean of the molecular weight of individual molecules in a sample. It is defined as the total weight of all molecules in a sample divided by the total number of molecules in the sample. Experimentally, the number average molecular weight ($M_n$) is determined by analyzing a sample divided into molecular weight fractions of species i having $n_i$ molecules of molecular weight $M_i$ through the formula $M_n=\Sigma M_i n_i/\mathrm{E} n_i$. The number average molecular weight can be measured by a variety of well-known methods including gel permeation chromatography, spectroscopic end group analysis and osmometry.

The term "oligomer" as used herein refers to a molecule having an intermediate relative molecular mass, the structure of which essentially includes a small plurality of units derived, actually or conceptually, from molecules of lower relative molecular mass. A molecule having an intermediate relative mass can be a molecule that has properties that vary with the removal of one or a few of the units. The variation in the properties that results from the removal of the one of more units can be a significant variation.

The term "radiation" as used herein refers to energetic particles travelling through a medium or space. Examples of radiation are visible light, infrared light, microwaves, radio waves, very low frequency waves, extremely low frequency waves, thermal radiation (heat), and black-body radiation.

The term "light" as used herein refers to electromagnetic radiation in and near wavelengths visible by the human eye, and includes ultra-violet (UV) light and infrared light, from about 10 nm to about 300,000 nm wavelength.

The term "UV light" as used herein refers to ultraviolet light, which is electromagnetic radiation with a wavelength of about 10 nm to about 400 nm.

The term "infrared light" as used herein refers to electromagnetic radiation with a wavelength between about 0.7 micrometers and about 300 micrometers.

The term "cure" as used herein refers to exposing to radiation in any form, heating, or allowing to undergo a physical or chemical reaction that results in hardening or an increase in viscosity.

The term "pore" as used herein refers to a depression, slit, or hole of any size or shape in a solid object. A pore can run all the way through an object or partially through the object. A pore can intersect other pores.

The term "solvent" as used herein refers to a liquid that can dissolve a solid, liquid, or gas. Nonlimiting examples of solvents are silicones, organic compounds, water, alcohols, ionic liquids, supercritical fluids, and cell incubation or growth media.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "silicate" as used herein refers to any silicon-containing compound wherein the silicon atom has four bonds to oxygen, wherein at least one of the oxygen atoms bound to the silicon atom is ionic, such as any salt of a silicic acid. The counterion to the oxygen ion can be any other suitable ion or ions. An oxygen atom can be substituted with other silicon atoms, allowing for a polymer structure. One or more oxygen atoms can be double-bonded to the silicon atom; therefore, a silicate molecule can include a silicon atom with 2, 3, or 4 oxygen atoms. Examples of silicates include aluminum silicate. Zeolites are one example of materials that can include aluminum silicate. A silicate can be in the form of a salt, ion, or a neutral compound.

The term "silica" as used herein can refer to silicon dioxide ($SiO_2$) of any particle size, shape, particle size distribution, shape distribution and surface functionality, including chemically treated silicas. It can also refer to a polysiloxane.

The term "silica gel" or "silica matrix" can refer to a substance that includes silica or a polysiloxane. The polysiloxane includes at least in part a silicon-oxygen-silicon (silicon atom bonded to oxygen atom bonded to silicon atom) chemical structure, wherein the compound can be a polymer of any length or degree of branching. The silica gel or matrix can include polysiloxanes in 30%, 50%, 80%, 90%, 95%, 99%, 99.5%, 99.9%, or in any suitable percent composition (wt %). A silica gel or silica matrix also can refer to a substance that includes at least in part a silicon-oxygen-carbon chain-oxygen-silicon chemical structure, wherein the compound can be a polymer of any length or degree of branching.

The term "room temperature" as used herein refers to ambient temperature, which can be, for example, between about 15° C. and about 28° C.

The term "surface" refers to a boundary or side of an object, wherein the boundary or side can have any perimeter shape and can have any three-dimensional shape, including flat, curved, or angular, wherein the boundary or side can be continuous or discontinuous. While the term surface generally refers to the outermost boundary of an object with no implied depth, when the term 'pores' is used in reference to a surface, it refers to both the surface opening and the depth to which the pores extend beneath the surface into the substrate.

The term "cancerous cell" refers to a cancer cell.

Description

In various embodiments, the present invention provides compositions for encapsulation of biomaterials in a silica-matrix. The present invention also provides methods of making silica-matrix encapsulated biomaterials, and to methods of using silica-matrix encapsulated biomaterials. In one embodiment, the present invention provides a method of encapsulating mammalian cells in a silica-matrix while maintaining metabolic activity. Maintaining metabolic activity can include maintaining viability. In another embodiment, the present invention provides a method of purifying cancer cells using a silica-matrix.

In embodiments of the present invention, a biomaterial such one or more cells (e.g. cancer cell, mammalian cell) can be derived from any suitable source, such as a tumor, a tissue sample, a blood sample, a urine sample, or any suitable sample taken from a biological organism.

Methods of Forming the Silica-Matrix Encapsulated Biomaterial

There are two primary methods to form silica the reactive silicon compound.

Hydrolysis Route. The route includes hydrolysis of alkoxide precursors under acidic or basic conditions in the presence of water. The water/alkoxide molar ratios may vary from 2 to 50. Hydrolysis of the alkoxide leads to the formation of silanol moieties (Si—OH) that are very reactive.

A hydrolysis reaction can be illustrated as follows: $\equiv$Si—OR+$H_2O$ $\leftrightarrow$ $\equiv$Si—OH+R—OH, wherein $\equiv$ represents three total bonds, and not necessarily a triple bond.

Alkali Metal Silicate Route. The route includes the acid treatment of silicate solutions. Typically, sodium silicate solutions with $SiO_2$ content between 27 to 30 wt % are used, or about 20-40%, or about 10-50%. A dilution in water of the metal silicate can be prepared first in order to reduce the amount of acid added. Acid treatment of silicates leads to the formation of silanol moieties (Si—OH) that are very reactive.

After formation of the reactive silicon compound, condensation reactions can occur to form the silica-matrix in a gelation process. Through condensation, these silanol moieties can react with one another to form —Si—O—Si— bonds (e.g., siloxanes). Additionally, silica nanoparticles of different sizes (e.g., Ludox or Nyacol) can also be added to the sodium silicate solution to increase the stiffness of the silica matrix. Through condensation of silanol with other silanols and/or siloxanes, an interconnected rigid network with pores of submicrometer dimensions and polymeric chains of $SiO_2$ is formed (gelation). There is very little or no heat adsorption or release at the gel point; only an increase in viscosity. The initial gel has a high viscosity but low elasticity. Following gelation, further crosslinking and chemical inclusion of isolated sol particles into the spanning cluster continues (aging), leading to an increase in the elasticity of the sample. In the bio-confinement process, the biomolecules or cells can be added after the hydrolysis step, confining the cells in a 3-D nanoporous network after the condensation reactions.

In one example, an alkoxysilane can condense with a silanol to give an $SiO_2$ bond with generation of an alcohol, illustrated as follows: ≡Si—OR+HO—Si≡↔≡Si—O—Si≡+R—OH, wherein ≡ represents three total bonds, and not necessarily a triple bond.

Similarly, a silanol can condense with any hydroxyl- or alkoxy-bearing group to give water or an alcohol, respectively.

In another example, a silanol can condense with another silanol, illustrated as follows: ≡Si—OH+HO—Si≡↔≡Si—O—Si≡+H$_2$O, wherein represents three total bonds, and not necessarily a triple bond.

Table A below shows a non-limiting list of preferred sources ("inorganic precursors") that can be used for the preparation of a reactive silicon compound using the hydrolysis or the alkali metal silicate route. In general, any alkoxide precursor that has hydrolysable groups can be used to form a reactive silicon compound via hydrolysis. In general, any metal silicate can be used to give a reactive silicon compound with treatment with acid. Examples of preferred metals include sodium and potassium.

2, 3, 4, or 5), which can maximize the rate of hydrolysis while limiting condensation. Next, evaporation of the alcohol can be achieved by any suitable means, for example rotoevaporation for 10 min. The mixture can be tested with chromic acid to ensure the absence of alcohol. Next, a biomaterial solution can be added and mixed, wherein the mixing can occur by any suitable means, for example by vortexing. Prior to addition, the biomaterial solutions can be prepared in a mammalian cell culture media, or in a potassium buffer or water at about neutral pH. The gelation process can take place within few minutes.

Another protocol includes the use of a colloidal silica. In this method silica gels can be prepared by mixing sodium silicate (e.g., 27 wt % SiO$_2$, 10 wt % NaOH) with colloidal silica nanoparticles (e.g., 12 nm diameter). Acid is added to the mixture to form the reactive silicon compounds, e.g., silanols. The solution can be at an approximately neutral pH for gelation. The mixture is homogenized by stirring by any

TABLE A

Inorganic Precursors

| Chemical Name | Acronym | Molecular Formula | Reactive Groups | Non-reactive group |
|---|---|---|---|---|
| Network Formers | | | | |
| Tetramethylorthosilicate | TMOS | Si(OCH$_3$)$_4$ | —OH | — |
| Tetramethylorthosilicate | TEOS | Si(OC$_2$H$_5$)$_4$ | —OH | — |
| Tetrakis(2-hydroxyethyl)orthosilicate | THEOS | Si(OCH$_2$CH$_2$OH)$_4$ | —OH | — |
| Methyldiethoxysilane | MDES | C$_5$H$_{14}$O$_2$Si | —OH | —CH3, —H |
| 3-(Glycidoxypropyl)triethoxysilane | GPMS | C$_9$H$_{20}$O$_5$Si | —OH, epoxy ring | — |
| 3-(Trimethoxysilyl)propylacrylate | TMSPA | H$_2$C=CHCO$_2$(CH$_2$)$_3$Si(OCH$_3$)$_3$ | —OH, acrylate group | — |
| N-(3-Triethoxysilylpropyl)pyrrole | TESPP | | —OH, pyrrole group | — |
| Vinyltriethoxysilane | VTES | H$_2$C=CHSi(OC$_2$H$_5$)$_3$ | —OH, vinyl group | — |
| Methacryloxypropyltriethoxysilane | TESPM | | —OH, methacryloxy group | — |
| Silica Nanoparticles (e.g. Ludox or Nyacol) | | SiO$_2$ | —OH | — |
| Sodium Silicate (e.g., 27% Silicic Acid 10% NaOH | Water glass | | —OH | — |
| Diglycerylsilane | DGS | | —OH | — |
| Structure Modifiers | | | | |
| Methyltriethoxysilane | MTMOS | CH$_3$Si(OCH$_3$)$_3$ | —OH | —CH3 |
| Trimethylmethoxysilane | TMMS | CH$_3$OSi(CH$_3$)$_3$ | —OH | —CH3 |
| Ethyltriethoxysilane | TEES | C$_2$H$_5$Si(OC$_2$H$_5$)$_3$ | —OH | —C2H5 |
| n-propyltriethoxysilane | TEPS | C$_2$H$_5$O)$_3$SiCH$_2$CH$_2$CH$_3$ | —OH | —C3H7 |
| n-butyltriethoxysilane | TEBS | C$_{10}$H$_{24}$O$_3$Si | —OH | —C4H9 |
| 3-aminopropyltriethoxysilane | APTS | H$_2$N(CH$_2$)$_3$Si(OC$_2$H$_5$)$_3$ | —OH, NH2 | |
| 3-(2,4-Dinitrophenylamino)propyl-triethoxysilane | | | —OH, Dinitropropylamino | |
| Mercaptopropyltriethoxysilane | TEPMS | HS(CH$_2$)$_3$Si(OCH$_2$CH$_3$)$_3$ | —OH, Thiol | |
| 3-(2-Aminoethylamino)propyl-triethoxysilane | | (CH$_3$O)$_3$Si(CH$_2$)$_3$NHCH$_2$CH$_2$NH$_2$ | —OH, NH2 | |
| Isocyanatopropyltriethoxysilane | | C$_{10}$H$_{21}$NO$_4$Si | —OH, Isocyanato | |
| Hydroxyl-terminated polydimethylsiloxane | PDMS | | —OH | —CH3 |
| triethoxysilyl-termonated polydimethylsiloxane | PDMS | | —OH | —CH3 |
| Methyltriethoxysilane | MTES | CH$_3$Si(OC$_2$H$_5$)$_3$ | —OH | —C2H5 |
| Triethoxysilyl-terminated poly(oxypropylene) | | | —OH | |

Generally, confinement of biomaterials can be carried out using variations of the hydrolysis and the alkali metal silicate methods of generating a reactive silicon compound. For the hydrolysis route, after the hydrolysis step of the alkoxide is completed, the method can include at least partial removal of the byproduct alcohol. In such a method, an alkoxide (TEOS or TMOS) can be hydrolyzed first in the presence of water and HCl. For example, a mixture of 1 mL of TEOS, 1 mL of water and 0.001M HCl can be sonicated for 10 to 15 min to ensure uniform mixture. The resultant product can be at low pH (e.g., less than 7, such as about 1, suitable means and mixed with a biomaterial suspension. Gelation can occur within about few minutes to a few hours at room temperature.

Encapsulation of Biomaterials

Traditional encapsulation techniques of biomaterials suffer problems and difficulties. For example, in some encapsulation techniques, the biomaterials do not survive. In some encapsulation techniques, the metabolic activity the biomaterial had prior to encapsulation is not preserved once the biomaterial is encapsulated.

In various embodiments, the present invention can avoid some problems encountered in other compositions or methods for encapsulation of cells. Various embodiments of the present invention can include hybrid silicon oxide materials from a combination of reactive silicon compounds (e.g., formed from a variety of precursors) and organic polymers that can produce a nanoporous or macroporous material for the immobilization of the cells. The protocol developed is biocompatible and the cells show good tolerance (cells have metabolic activity and enzymatic activity after encapsulation) to the byproducts produced during the gel synthesis.

In various embodiments, the present invention provides new and significant advantages. In some embodiments, these include incorporation of an osmolyte that partitions between the silica surface and in the water during the encapsulation process. Additionally, in some examples silica nanoparticles themselves can be used as an encapsulation agent, allowing the use of a completely biocompatible coalescence mechanism of gel formation. In some examples, the composition and method has substantial flexibility in terms of properties of the encapsulated biomaterial including the mechanical properties, surface chemistry, and porosity, and various embodiments of the present method can provide facile scale up.

Various embodiments of the present invention can include the use of silica nanoparticles at different concentrations. This can allow destabilization and gelation of the colloidal suspension of silica nanoparticles by changing the pH to a neutral or close to neutral value. Gelation can also be induced by dialyzing first the colloidal suspension against water for at least 24 h. In dialyzing, the colloidal suspension can be contacted to one side of a membrane and water can be contacted to the other, changing the pH of the colloidal suspension. Then, an organic precursor can be added. For example, trehalose in powder form can be dissolved in the colloidal suspension in concentrations of, in some examples, up to 0.5 M. After stirring for about 5 minutes, for example, in a vortex machine, or until the sample becomes a transparent and uniform mixture, the biomaterial solution can then be added and mixed. This mixing can be performed by any suitable means, for example in a vortex machine. Gelation can take place immediately and the samples can then be left to age, for example, for 24 hours. The preparation and analysis of samples prepared in this fashion are included the Example section.

Various embodiments of the present invention provide compositions and techniques that allow the incorporation of cells in mesoporous or macroporous hybrid silica matrices. In various embodiments, a source of reactive silicon compound (for example, the "inorganic precursors" given in Table A) can be provided that is hydrolyzed in an acid solution (e.g., acetic acid or HCl) to give a reactive silicon compound, e.g., silanols. Then the organic component (for example, see "organic precursors" given in Table B, below, which shows a nonlimiting list of examples of organic precursors) can be added and mixed until a homogeneous mixture is obtained. In one example, PEG 600 Da can be used for a nanoporous material and PEG 10 kDa can be used for a macroporous material. Finally cells can be added and gently mixed with mild stirring or pipetting. The gel can form in a period of time between minutes to hours depending on the composition initially chosen.

TABLE 2

Organic Precursors

| Chemical Name | Acronym | Type of Interaction with Silica | Origin |
| --- | --- | --- | --- |
| Polyethylene glycol | PEG | HB | Synthetic |
| Polyvinyl alcohol | PVA | HB | Synthetic |
| Polyacrylicacid | HPAA | Electrostatic | Synthetic |
| Polymethyl methacrylate | PMMA | HB | Synthetic |
| PHEMA | PHEMA | HB | Synthetic |
| Pluronic F127, P123 | PEO-PE-PEO | HB | Synthetic |
| Aminoacids | A, G, Y, ... | HB, electrostatic | Synthetic |
| Peptide sequences | — | HB, electrostatic | Synthetic |
| Mono peptide sequences | — | HB, electrostatic | Synthetic |
| Alginate | — | HB, electrostatic | Natural |
| Gelatin | — | HB, electrostatic | Natural |
| Chitosan | — | HB, electrostatic | Natural |
| Sucrose | — | HB | Natural |
| Trehalose | — | HB | Natural |
| Dextran | — | HB | Natural |
| Casein | — | HB, electrostatic | Natural |
| Bovine serum | — | HB, electrostatic | Natural |
| Collagen | — | HB, electrostatic | Natural |

Nanoporous and Macroporous Silica-Matrix Synthesis

The compositions and methods of the present invention for forming a nanoporous or macroporous silica-matrix can be chosen to maximize the viability and metabolic activity of cells encapsulated by the matrix. Viable and active cells after encapsulation can allow using the cells as metabolic factories for cell-based biochemistry processes such as: biosensing, biocatalysis, bioreactive coatings, and the like.

Compositions and methods for forming nanoporous silica-matrixes include all compositions and methods for forming silica-matrix encapsulated biomaterials described herein, as well as the specific procedure described here. Embodiments encompass silica-matricies that are nanoporous, macroporous, or a combination thereof. For formation of nanoporous silica-matrixes, a step can include treating a silicate-containing solution with acid to create a reactive silicon compound (e.g., silanols). As described herein, acidification of silicate-containing colloidal suspensions of silica nanoparticles (e.g., between about 10 to 50 wt %) can form silanols. After formation of reactive silicon compounds via acidification of silicates, a highly reactive (e.g., silanol-containing) hydrolyzed silane solution can be added to facilitate crosslinking or to allow surface chemistry modification (see Table A for list of silane precursors, "inorganic precursors"). The ratios of colloidal nanoparticles and silane crosslinking agents can be chosen according to the mechanical, chemical, or optical properties desired. The next step can include the addition of an organic precursor, such as those shown in Table B. The organic precursor can be a synthetic polymer, natural polymer or monomer, or amino acid. The concentrations of incorporation can be in mass or volume ratios with respect to the silica content and may vary from 1% up to 50% in mass or volume. By incorporating the organic component, the following are examples of the effects can occur: (1) reduction of interactions of reactive moieties on the silica surface (e.g., SiOH) with cell membranes, which interactions can be detrimental to the preservation of valuable activity of the biomaterial for long-term encapsulation, (2) post-gelation surface modification can occur with organic or inorganic chemistry conjugation techniques (e.g., modification or addition of the functional groups at the surface), (3) reduction of shrinkage during aging of the gel, and (4) increased mesoporosity of the gel. Before or after incorporation of the organic component, the biomaterial can be incorporated into the mixture. Cells can be suspended in their own media, salt solutions or in water. The cell solution of choice can be dictated by the cell type. After addition of the organic component, the pH can be checked and in some cases may be adjusted with a base (e.g., sodium hydroxide). Gelation can take place in few minutes to hours depending on the compositions and precursors chosen.

Compositions and methods for forming macroporous silica-matrixes include all compositions and methods for forming silica-matrix encapsulated biomaterials described herein, as well as the specific procedure described here. For formation of macroporous silica-matrixes, the method can include inducing a controlled phase separation along with the sol-gel transition of the solution components. In general, a hydrophilic organic polymer can be mixed in water under acidic conditions (e.g., polyethylene glycol, polyvinyl alcohol, polyacrylic acid). The acid concentration can be chosen from about $10^{-3}$ M to about 1M (e.g., 0.01M, e.g., acetic acid, HCl, HNO$_3$) to favor the hydrolysis or condensation process when the silica precursor is added. After a clear transparent mixture is obtained the remaining part of the process can be carried out at any suitable temperature, for example about 0° C. The silica precursor can be added after the removal of the byproduct of hydrolysis when required (e.g., for TMOS or TEOS a rotating evaporator can be used; otherwise; the silica precursor can be added to the acidic polymeric solution (e.g., THEOS, sodium silicate, silica nanoparticles). At this step the pH can be raised to a suitable value, for example a pH of 6. Then, the cells can be added. In the final step, the working solution can be deposited on the desired molds and cast at various temperatures, for example, room temperature or a lower temperature, about 30° C., 37° C., 40° C., about 45° C., or a higher temperature. The temperature used can depend on the type of structure desired and also can depend on the type of biomaterial used. The gelling and aging times for the material can be any suitable time, for example, about 4, 6, 12, 18, or about 24 hours. Aging can be conducted while the material is wet or dry, e.g., hydrated or dehydrated. After the aging step the gels can be rehydrated and stored at any temperature, including, for example, 4° C., or room temperature.

Modification of the Properties of the Silica-Matrix Encapsulated Biomaterial

In various embodiments, the use of hybrid materials (silicon oxide plus organic polymers or monomers) can cause a synergistic interaction of the organic and inorganic groups of the component materials that can provide a diverse set of materials with novel and advantageous properties. Mechanical, optical, and chemical properties of the resulting silica-matrix encapsulated biomaterials can be tailored. Porosity, mechanical, optical, and surface chemistry properties can be modified in a versatile and facile manner that allow the creation of functional biohybrid materials.

For example, in applications where high rates of diffusion through the material are required (e.g., biocatalysis, bioremediation) a suitable porosity of the silica gel matrix can help ensure high rates of biochemical conversion or purification. In the nanoporous gel, when an organic polymer or monomer is included during synthesis, the mesoporosity of the material can be increased. In addition, added organic polymers or monomers can interact with the surface silanol or siloxane silica groups, which can reduce the possibilities of damaging the structure and functionality of the biomaterials. The incorporation of these groups can occur after an alkoxysilane hydrolysis step, which can provide a uniform mixture of the organic compound through the silica material. Polyethylene glycol or disaccharides can be used to increase the mesoporosity, as shown in the Examples.

Encapsulation of Cancer Cells

In various embodiments, the present invention provides a silica-matrix encapsulated biomaterial, including a reaction product of a mixture. The mixture includes a reactive silicon compound. The mixture also includes a biomaterial including at least one living cancerous cell and at least one living non-cancerous cell. The at least one living cancerous cell can be a mammalian cell. The at least one living non-cancerous cell can be a mammalian cell. After formation of the silica-matrix encapsulated biomaterial, the at least one cancer cell lives and the at least one non-cancerous cell dies.

In various embodiments, the present invention provides a method of generating cancer cells substantially free of non-cancerous cells, or a method of selectively purifying cancerous cells. The method includes forming a silica-matrix encapsulated biomaterial. The silica-matrix encapsulated biomaterial includes the reaction product of a mixture. The mixture includes a reactive silicon compound. The mixture also includes a biomaterial including at least one living cancer cell, and at least one living non-cancerous cell. After forming the silica-matrix encapsulated biomaterial, the at least one non-cancerous cell dies, and the at least one cancer cell survives. The method also includes removing the at least one cancer cell from the silica-matrix.

In some embodiments, the silica-matrix encapsulated biomaterial can be a thixotropic silica gel.

In some embodiments, the biomaterial includes a plurality of cancer cells, and a plurality of non-cancerous cells. In some examples, after encapsulation of the biomaterial with the silica-matrix, the non-cancerous cells die faster than the cancer cells. In some examples, the non-cancerous cells die at a rate of about 1.1 times faster than the rate of death of the cancer cells, or about 1.2, 1.3, 1.4, 1.5, 1.6, 1.7, 1.8, 1.9, 2.0, 2, 2.5, 3, 4, or about 5 times faster than the rate of death of the cancer cells. In some embodiments, after encapsulation of the biomaterial with the silica-matrix, some of the cancer cells remain living after substantially all of the non-cancerous cells have died. In some embodiments, at about 2 h, 4, 6, 8, 10, 12 h, 24 h, 2 d, 3 d, 4 d, or 5 d after encapsulation, greater than about 10% of the non-cancerous cells have died, or about 20, 30, 40, 50, 60, 70, 80, 90, or greater than about 95% of non-cancerous cells have died, and less than about 10% of the cancer cells have died, or about 20, 30, 40, 50, 60, 70, 80, or less than about 90% of the cancer cells have died. In some embodiments, at about 12 hours after encapsulation of the biomaterial with the silica-matrix, less than 40% of the non-cancerous cells have died, and greater than about 60% of the cancer cells have died. In some embodiments, at about 24 hours after encapsulation of the biomaterial with the silica-matrix, less than 40% of the non-cancerous cells have died, and greater than about 60% of the cancer cells have died.

In various embodiments, the present invention provides a method of generating second cancer cells substantially free of first cancer cells, or a method of selectively purifying second cancer cells, the second cancer cells having a different phenotype than the first cancer cells. The method includes forming a silica-matrix encapsulated biomaterial. The silica-matrix encapsulated biomaterial includes the reaction product of a mixture. The mixture includes a reactive silicon compound. The mixture also includes a biomaterial including at least one living first cancerous mammalian cell and at least one living second cancerous mammalian cell, the first living cancerous mammalian cell and the second living cancerous mammalian cell having different phenotypes, wherein after formation of the silica-matrix encapsulated biomaterial, the at least one first cancerous cell dies, and the at least one second cancerous cell survives. As used herein, cells having different phenotypes can differ by at least one of genotype, propensity for metastasis, morphology, development, biochemical or physiological properties, and combinations thereof.

In various embodiments, the present invention provides a method of selectively purifying cancer cells. The method includes forming a silica-matrix encapsulated biomaterial. The silica-matrix encapsulated biomaterial includes a reaction product of a mixture including a reactive silicon compound. The silica-matrix encapsulated biomaterial also includes a biomaterial including at least one first living cancerous mammalian cell and at least one second living cancerous mammalian cell, the first living cancerous mammalian cell and the second living cancerous mammalian cell having different phenotypes. After forming the silica-matrix encapsulated biomaterial, the at least one first cancerous cell dies, and the at least one second cancerous cell survives. The method also includes removing the at least one second cancerous cell from the silica-matrix. Advantageously, this method can allow isolation of metastatic sub-populations of cancerous cells, and can allow isolation of metastatic sub-populations of cells from samples including both noncancerous and cancerous cells.

In some embodiments, the biomaterial includes a plurality of first cancer cells, and a plurality of second cancerous cells, the first and second cancerous cells having different phenotypes. In some examples, after encapsulation of the biomaterial with the silica-matrix, the first cancer cells die faster than the second cancerous cells. In some examples, the first cancer cells die at a rate of about 1.1 times faster than the rate of death of the second cancer cells, or about 1.2, 1.3, 1.4, 1.5, 1.6, 1.7, 1.8, 1.9, 2.0, 2, 2.5, 3, 4, or about 5 times faster than the rate of death of the second cancer cells. In some embodiments, after encapsulation of the biomaterial with the silica-matrix, some of the second cancer cells remain living after substantially all of the first cancer cells have died. In some embodiments, at about 2 h, 4, 6, 8, 10, 12 h, 24 h, 2 d, 3 d, 4 d, or 5 d after encapsulation, greater than about 10% of the first cancer cells have died, or about 20, 30, 40, 50, 60, 70, 80, 90, or greater than about 95% of first cancer cells have died, and less than about 10% of the second cancer cells have died, or about 20, 30, 40, 50, 60, 70, 80, or less than about 90% of the second cancer cells have died. In some embodiments, at about 12 hours after encapsulation of the biomaterial with the silica-matrix, less than 40% of the second cancer cells have died, and greater than about 60% of the first cancer cells have died. In some embodiments, at about 24 hours after encapsulation of the biomaterial with the silica-matrix, less than 40% of the second cancer cells have died, and greater than about 60% of the first cancer cells have died.

EXAMPLES

The present invention can be better understood by reference to the following examples which are offered by way of illustration. The present invention is not limited to the examples given herein.

1.0. Encapsulation of Mammalian Cells in Silica Nanoporous Gels: Interactions at the Biointerface 1.1) Introduction Silica gel encapsulation of mammalian cells is a challenging task since all the previous strategies reported in the literature have failed in maintaining the membrane integrity and metabolic activity (MA) of the encapsulated cells for long periods of time. To successfully encapsulate mammalian cells, issues associated with sol-gel processing and encapsulation can be addressed, including the specific surface interactions, toxicity induced by the by-products of hydrolysis and condensation reactions, gelation kinetics, and aging of the gel, which introduce mechanical stresses.

The effects of silica gelation by-products on the membrane integrity and MA of mammalian cells have been reported. On the other hand, the effects of silica gel aging have not been fully explored. The gel aging phase is most likely the stage at which surface interactions form and mature at the biointerface (silica-lipid membrane interface). Aditionally, compressive stresses also arise due to silica matrix syneresis, negatively effecting the membrane integrity and MA of the encapsulated mammalian cells.

In this study, membrane integrity and MA of encapsulated mammalian cells (e.g., human foreskin fibroblast, HFF; irradiated human foreskin fibroblasts, HFFIR, mouse embryonic fibroblasts, MEF; and irradiated mouse embryonic fibroblast, MEFIR) during aging of the silica matrix they were encapsulated in was investigated. Silica gels made from water soluble alkoxides, tetrakis (2-hydroxyethyl) orthosilicate (THEOS) and tetramethyl orthosilicate (TMOS) were used. The nanoporous silica matrix was synthesized in the presence of culture media. The by-product of the hydrolysis process, ethylene glycol (EG) for THEOS, showed no effect on the membrane integrity and MA when the mammalian cells were incubated in EG and compared with the mammalian cells incubated in culture media. On the other hand, methanol, the by-product produced during the hydrolysis of TMOS, was removed by evaporation prior to cell encapsulation.

The results showed that encapsulated cells experience significant conformational changes in their lipid membranes during the gelation and aging of the nanoporous silica matrix. Measurements of the MA and viability of the encapsulated cells showed that majority of the cells tolerate the initial change in their lipid organization right after encapsulation. However, aging of the silica matrix beyond 6 h induced additional changes which was accompanied by a significant drop in MA of the encapsulated cells and also leakage of intracellular lactate dehydrogenase (LDH) from the encapsulated cells. These were signs that the death of the encapsulated cells were accelerated during aging.

It was hypothesized that reducing the interactions at the biointerface during aging would be beneficial for the enhancement of the MA and viability of the encapsulated cells. The biointerface interactions were reduced during matrix aging by incorporating polyethylene glycol (PEG) at different molecular weights into the matrix. The hydrophilic part of PEG forms hydrogen bonds with silica surfaces and can prevent surface interactions. The immediate effect of PEG was the reduction of the time dependent decrease in MA of the encapsulated cells and the reduced LDH leakage. PEG stopped the specific chemical reactions at the biointerface, but it did not change the buildup of mechanical compressive stresses (due to matrix shrinkage and the reproductive stress within the cells). Therefore, it was further envisioned that arresting the cellular division of HFF and MEF cells by irradiation would further increase the time constant of MA decrease in encapsulated cells.

1.2) Materials and Methods

Tetrakis (2-hydroxyethyl) orthosilicate (THEOS) was purchased from Gelest (Morrisville, Pa.), Tetramethyl orthosilicate (TMOS) was obtained from Sigma. Colloidal silica nanoparticles (SNPs) were obtained from NYACOL Nano Technologies Inc. (Ashland, Mass.). SNPs were purified using dialysis through 3.5 kDa Spectra/Pore membranes purchased from Spectrum Laboratories Inc. (Rancho Dominguez, Calif.). Linear PEG (at molecular weights ($M_w$) of 0.4, and 0.6 kDa) was purchased from Sigma, and 4-arm PEG ($M_w$=2 kDa) was purchased from Creative PEGWorks (Winston Salem, N.C.). PEG was used to increase the porosity of the gels and to modify the surface of the silica gels. All chemicals were used without further purification.

1.2.1) Cell Culture

Human foreskin fibroblasts (HFF), and mouse embryonic fibroblasts (MEF) were obtained from the American Type Cell Collection (Manasas, Va.). HFF and MEF cells were cultured in DMEM basal media supplemented with 15% fetal bovine serum (FBS), and 1% penicillin/streptomycin. Cells were incubated in a 5% $CO_2$ atmosphere at 37° C. until they reached 80-90% confluence. Cells were then washed with phosphate buffer saline (PBS) and trypsinized with 0.25% Trypsin-EDTA for 5 min at 37° C. For cytotoxicity measurements and encapsulation experiments, cells were centrifuged at 800 rpm for 5 min. The supernatant was removed and the pelleted cells were suspended in their own growth media at a concentration of about 500,000 cells/ml.

1.2.2) Cell Irradiation

HFF and MEF cells were irradiated with an X-ray machine at a dose of 6,000, and 10,000 rads for HFF and MEF cells, respectively. Irradiated HFF (HFFIR) and irradiated MEF (MEFIR) cells stopped replicating after irradiation. Encapsulation of the irradiated cells was conducted in a similar fashion to that used for non-irradiated cells as detailed previously.

1.2.3) Silica Gel Synthesis and Characterization

Silica gels were synthesized by direct hydrolysis of 10% (v/v) THEOS in cell culture media without using any acid catalyst. The culture media was prepared with 0.01M of 85 nm diameter SNPs. SNPs were used as nucleation seeds for the development of the silica network. The mixture was stirred vigorously for 60 s, accompanied by a change in the pH of the mixture (about pH 5) showing that THEOS was hydrolysed. Then, the reaction continued as a condensation polymerization forming the nanoporous network. The neutral pH (about 7) was recovered naturally after the sol-gel transition of the hydrolysed alkoxide was completed. Silica gels of the alkoxide TMOS were prepared in a similar fashion.

Some of the silica gels were produced using PEG (termed SPEG gels). Gels produced with linear PEG ($M_w$=0.4, 0.6 kDa) were termed SPEG-1 and gels produced with 4 arm PEG ($M_w$=2 kDa) were termed SPEG-4-arm. In a typical preparation, PEG was dissolved in cell culture media and the solution was mixed with hydrolysed THEOS solution. The final volume ratio of PEG in the mixture was 2.3, 4.5, or 10% (v/v). PEG interacted with the silica matrix in two different ways: (a) by hydrogen bonding with the silanol groups that formed after the hydrolysis of the alkoxide (with the ether oxygen of PEG); and (b) by covalently linking to the silica surface through transesterification reactions between the hydroxyl groups of PEG and the hydrolysed alkoxide.

The prepared gels were characterized using FTIR spectroscopy, UV-vis spectroscopy and scanning electron microscopy (SEM). FTIR analysis of pure silica and SPEG gels was conducted to determine the changes in the chemical structures of the gels with incorporation of PEG. UV-vis spectroscopy was performed on aged samples prepared in 96-well plates to determine whether phase separation occurred in the gel. Scanning electron microscopy (SEM) analysis was performed with a Hitachi S-900 FESEM (Hitachi Co., Lawrenceville, Ga.). For SEM analysis, silica gels were dehydrated in ethanol and then transferred to a $CO_2$ critical point drier (Samdri-780A, Tousimis, Rockville, Md.). Prior to imaging, dried samples were sputtered with Tungsten at a rate of 1 Å/min for 15 min. SEM images of the different gels prepared were analyzed in order to determine porosity (the percentage void space using the ImageJ software), and to explore the ultrastructure.

1.2.4) Cell Encapsulation

For encapsulation in silica gels, 20 µl of 0.01M SNPs in culture media was mixed with 4 µl of THEOS. The mixture was vigorously vortexed for 1 min and was placed on ice to avoid condensation. After the pH recovered to 7, 20 µl of cell solution (500,000 cell/ml) was added, mixed by pipetting and transferred to a 96 well plate. In parallel experiments, cells were encapsulated in silica gels prepared with TMOS. In these gels the alkoxide was hydrolyzed in water and catalyzed with 0.01M HCl at 1/1/0.01 (v/v/v). After hydrolysis the mixture was heated to 65° C. to remove the alcohol by-product. Then, 20 µl of 0.01M SNPs in culture media was mixed with 4 µl of hydrolyzed TMOS. This step neutralized the solution. Cells suspended in media (500,000 cell/ml) were added to this solution. Gelation of the silica gels was completed within 5 min, and 90 µl of media was added on top of the gels to avoid drying. The encapsulated cells were incubated at 5% $CO_2$ atmosphere and 37° C. for up to 60 h.

For encapsulation in SPEG gels, linear or 4-arm PEG was added at a concentration of 2.3%, 4.5%, 10% (v/v) to 20 µl of 0.01M SNPs in culture media. The rest of the procedure was identical to that followed for making the gels that did not contain PEG.

1.2.5) Fluorescence Microscopy

Membrane integrity of the encapsulated cells in silica and SPEG gels was measured using a live-dead fluorescence assay containing Hoechst (H) and Propidium Iodide (PI) fluorescent dyes. A Nikon Eclipse T200 microscope (Nikon Instruments Inc., Melville, N.Y.) equipped with 10x, and 20x objectives were used to collect the bright field and fluorescent images.

1.2.6) Membrane Analysis of the Encapsulated Cells

Conformation of the cell membrane lipids was determined using FTIR spectroscopy. Spectral analysis was performed using Omnic software provided by the manufacturer. The change in the lipid conformation change was monitored by measuring the peak location of the v-$CH_2$ (symmetric stretching) band located at 2850 $cm^{-1}$ for cells in solution (and at 2843 $cm^{-1}$ for the encapsulated cells). Due to overlapping of the PEG and ethylene glycol (EG) $CH_2$ bands in the 2900-2700 $cm^{-1}$ region, FTIR analysis of encapsulated cells was only carried out in silica gels prepared without PEG.

1.2.7) Metabolic Activity and Lactate Dehydrogenase (LDH) Leakage Measurements

MA of the encapsulated cells was measured with alamar blue (AB) fluorescence. For fluorescence measurements a SpectraMAX Gemini microplate reader (Molecular Devices Inc, Sunnyvale, Calif.) was used. The samples were excited at 540 nm and their emission was measured at 590 nm. LDH assay was performed 24 h after encapsulation of the cells. The assay was performed using a commercially available kit (Roche Applied Science, Indianapolis, Ind.). The levels of extracellular LDH activity were determined using a UV-vis SpectraMAX microplate reader (Molecular Devices, Sunnyvale, Calif.) by absorbance at 492 nm. The readings were calibrated using blank wells, wells that only contain media, cells in media, and gels that do not contain any cells.

1.31 Results 1.3.1) Characterization of the Silica and SPEG Gels

In pure silica gels, when THEOS or hydrolyzed TMOS were mixed with the solution containing the cells, phase separation was not detected. The gelation time ($T_g$) of the pure silica gels decreased with an increase in the alkoxide concentration. FIG. 1 shows that the there is a logarithmic correlation between $T_g$ and volume ratio of THEOS. Gels prepared with TMOS had the same trend (data not shown). The presence of the cells did not affect the gelation time for the different concentrations of the alkoxides.

For SPEG-4-arm gels prepared with 2.3% or 4.5% PEG, the onset of the gelation was concurrent with phase separation, as indicated in FIG. 1. Therefore, it was not possible to determine the exact time of onset of gelation. In SPEG-4-arm gels prepared with concentrations of PEG higher than 4.5% PEG, phase separation was drastically reduced. A logarithmic correlation between $T_g$ and 4-arm PEG concentration was observed (FIG. 1). FIG. 1 illustrates gelation times ($T_g$) for gels made with THEOS and PEG. In these experiments, a constant concentration of 10% (v/v) THEOS was used.

Figure 2A:
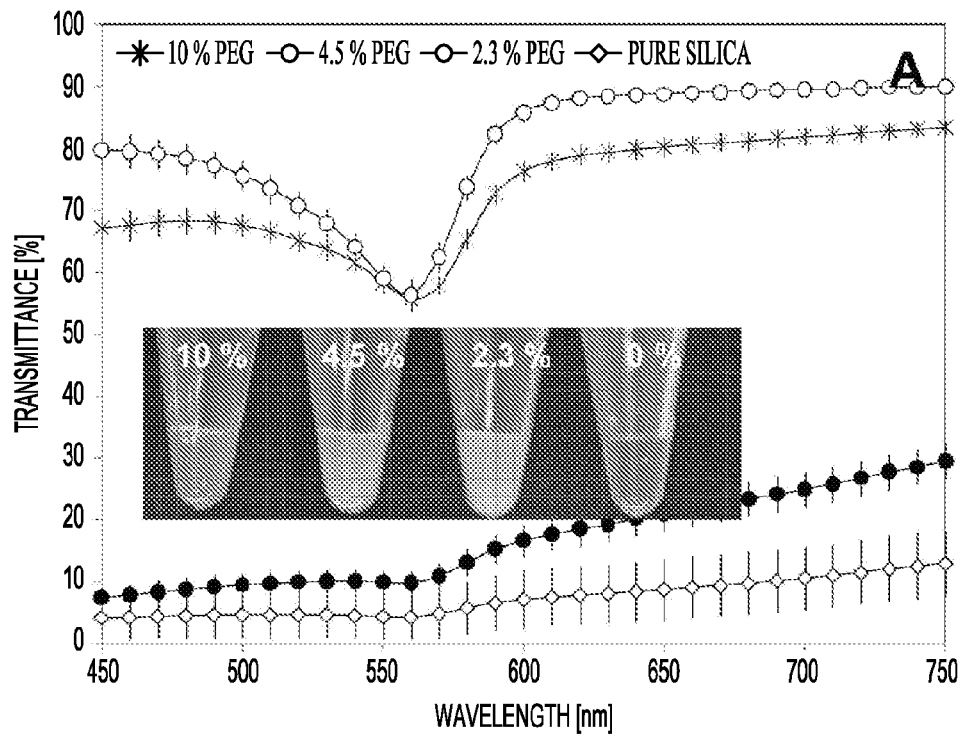
FIGS. 2 (A), (B), and (C) illustrate optical properties of silica and SPEG gels prepared with 10% (v/v) THEOS, in accordance with various embodiments.
Figure 2B:
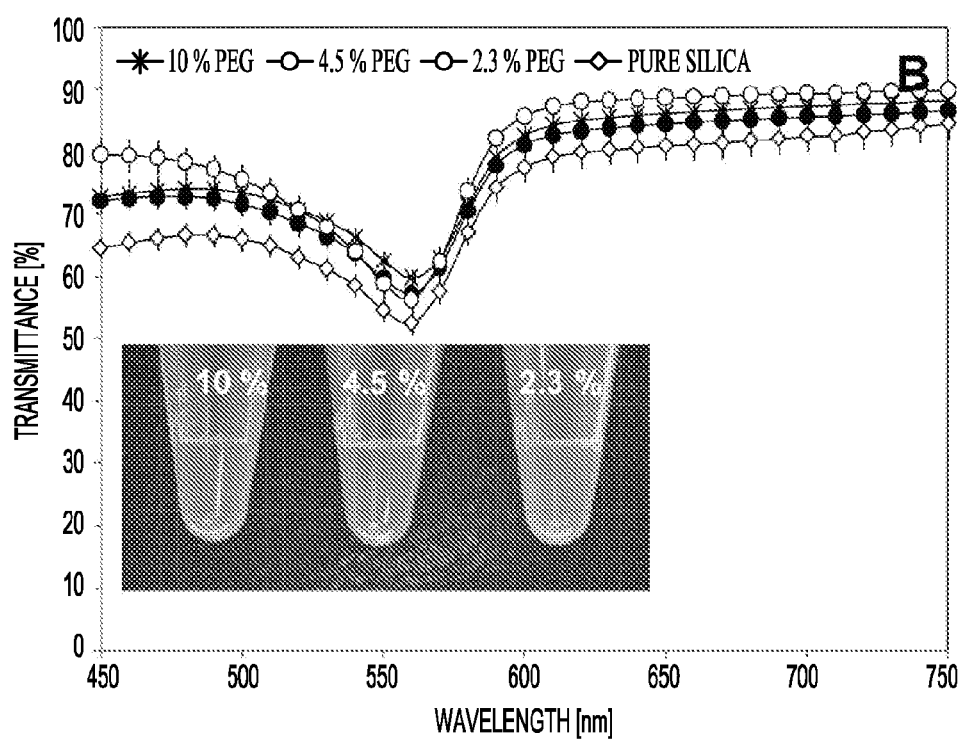
Figure 2C:
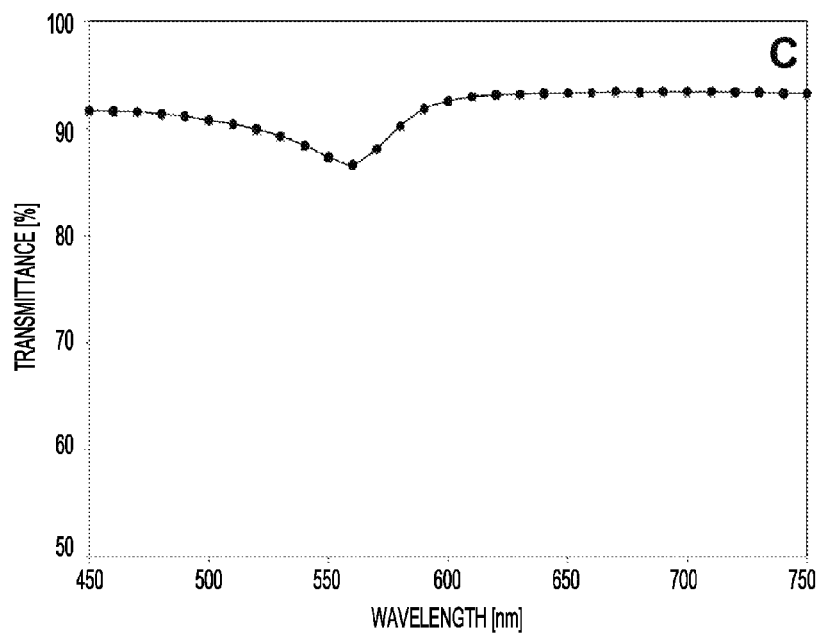

Phase separation causes increased adsorption of light and therefore UV-vis spectroscopy can be used to detect phase separation (FIG. 2(A)). Interestingly, in some gels it was observed that even though phase separation was present, a gel structure was formed. In SPEG-4-arm gels prepared with 10% PEG, phase separation was drastically reduced as indicated by high optical transmittance. The transmittance values of SPEG-1 gels did not show significant phase separation at low or high concentrations of PEG (FIG. 2(B)). A drop in transmittance was observed in all gels at around 560 nm. This corresponded to absorbance by the cell culture media that was used as a solvent in all gels (FIG. 2(C)). FIG. 2 (A)-(C) illustrates optical properties of silica and SPEG gels prepared with 10% (v/v) THEOS, different $M_w$ and concentrations of PEG, with (A) SPEG-4-arm, (B) SPEG-1 ($M_w$=0.6 kDa), and (C) Transmittance of cell culture media. The drop in the transmittance at 560 nm is due to absorbance of albumin at that wavelength.

Figures 3A, 3B, 3C, 3D:
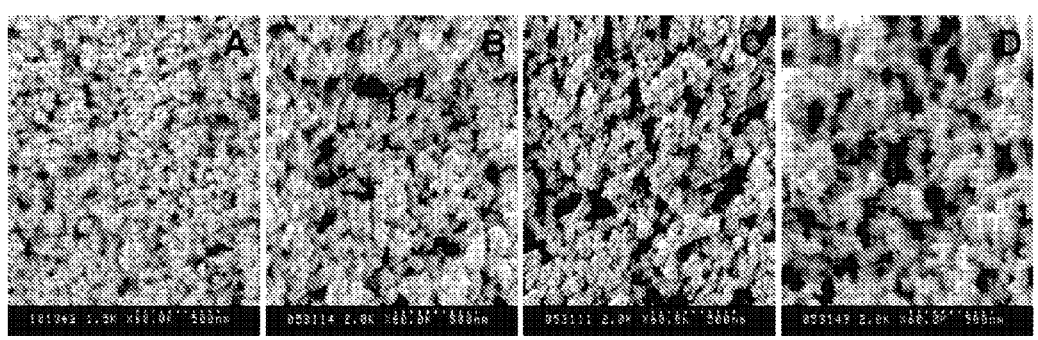
FIGS. 3 (A), (B), (C), and (D) illustrate electron microscopy micrographs of SPEG gels, in accordance with various embodiments.
Figure 4:
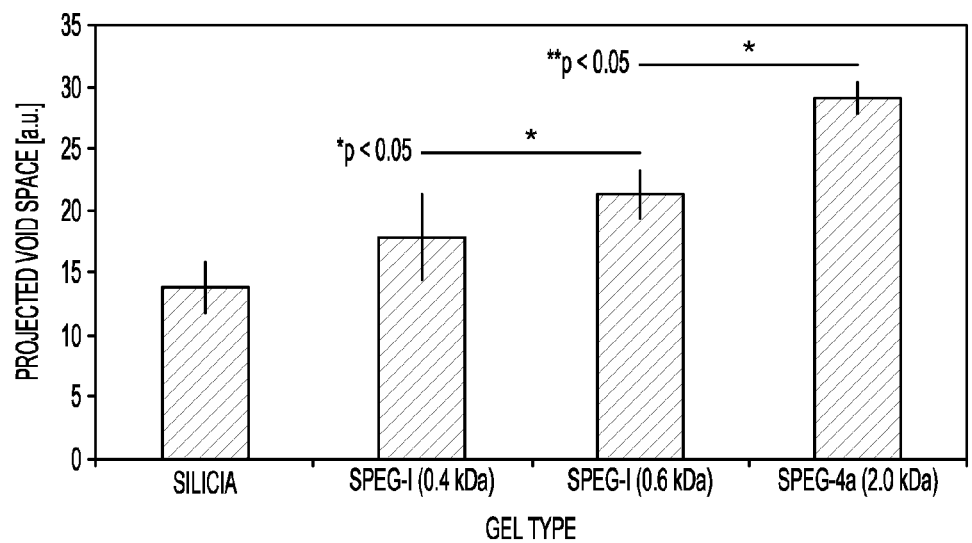
FIG. 4 illustrates projected void space versus gel type, in accordance with various embodiments.

FIG. 3 shows the SEM micrographs of (A) pure silica gel, (B) SPEG-1 gel (0.4 kDa), (C) SPEG-1 (0.6 kDa), and (D) SPEG-4-arm. All gels were formed by the aggregation of SNPs in the form of a three dimensional network. Pure silica gels exhibited a more compact agglomeration of SNPs with less void space (or volume fraction) when compared to the SPEG gels, showing the role of PEG as a porogen. Increasing PEG size (by increasing the $M_w$) increased the void space fraction in the gels such that 13.77%±2%, 18.45%±1.3%, 21.42%±1.9%, and 29.1%±1.1% of void space was obtained in pure silica, SPEG-1 (0.4 kDa), SPEG-1 (0.6 kDa), and SPEG-4-arm gels, respectively (FIG. 4). FIG. 4 illustrates electron microscopy micrographs of the nanostructure of the SPEG gels with 10% (v/v) THEOS: (A) Pure silica gel, (B) 10% SPEG-1 (0.4 kDa), (C) 10% SPEG-1 (0.6 kDa), (D) 10% SPEG-4-arm (2 kDa).

Figure 5:
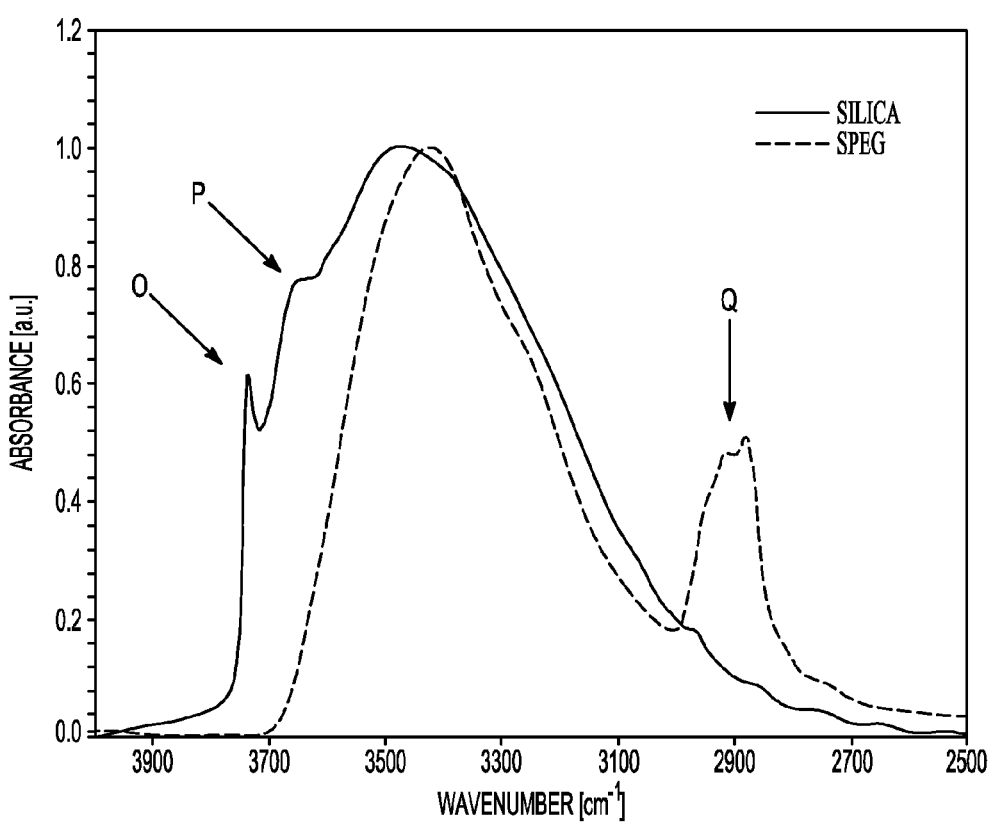
FIG. 5 illustrates an IR spectrum of pure silica gel and a superimposed IR spectrum of 10% SPEG-4-arm ($M_w$=2 kDa) gel, in accordance with various embodiments.

PEG was added to the gels to modify the silica surface. Modification of the silica surface can include hydrogen bonding interactions with PEG, or covalent bonding between hydroxyl groups. This interaction of the silica surface with PEG was confirmed by IR analysis in the region 3900-2500 $cm^{-1}$ (FIG. 5). In silica gels, at 3737 $cm^{-1}$ the IR spectrum showed a sharp peak (point O in FIG. 5), which corresponded to the stretching vibrations of the unbound silanol groups located on the silica surface (—SiOH). Moreover, at 3662 $cm^{-1}$ a shoulder in the IR spectrum was observed (point P in FIG. 5). This shoulder originated from the stretching vibrations of the vicinal silanol groups. In the IR spectra of the SPEG gels, the stretching vibrations of the surface silanols were not detected showing that PEG interacted with the silica surface binding with the silanol (—SiOH) groups. Similar interaction of organic polymers and sugars with silica through silanol groups was previously reported in colloidal silica. In SPEG gels, the asymmetric stretching vibrations of PEG (—$CH_2$) are located in the region 2900 $cm^{-1}$ to 2750 $cm^{-1}$ (point Q in FIG. 5).

FIG. 4 illustrates a comparison of the projected void space (a measure of porosity) obtained in different gels (n=5). Statistical analysis was conducted using ANOVA. FIG. 5 illustrates IR spectra of pure silica gel and 10% SPEG-4-arm ($M_w$=2 kDa) gels showing the differences in their surface chemistry.

1.3.2) Cytotoxicity of the Gel Components

Figure 6A:
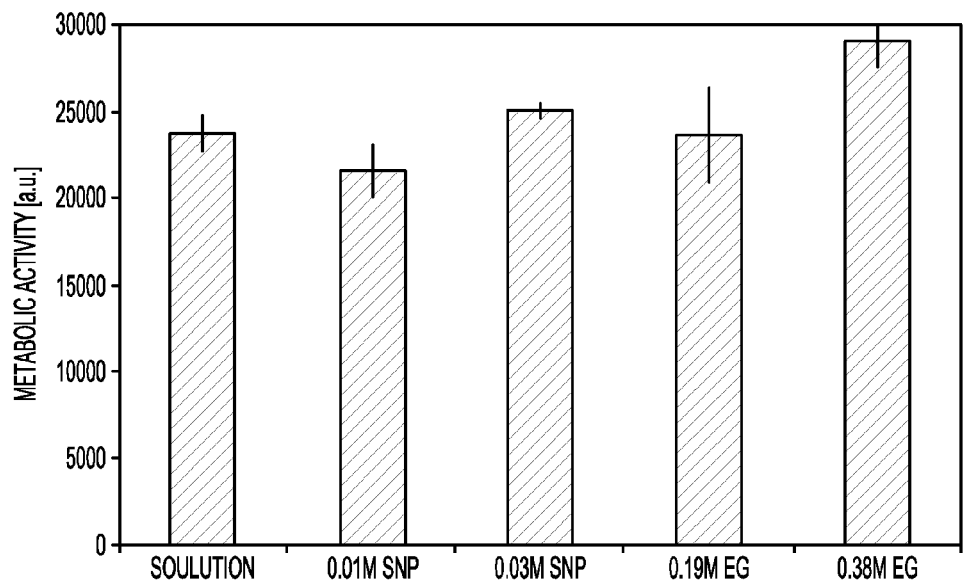
FIGS. 6 (A) and (B) illustrate cytotoxicity of SNPs and EG on (A) HFF, and (B) MEF, in accordance with various embodiments.
Figure 6B:
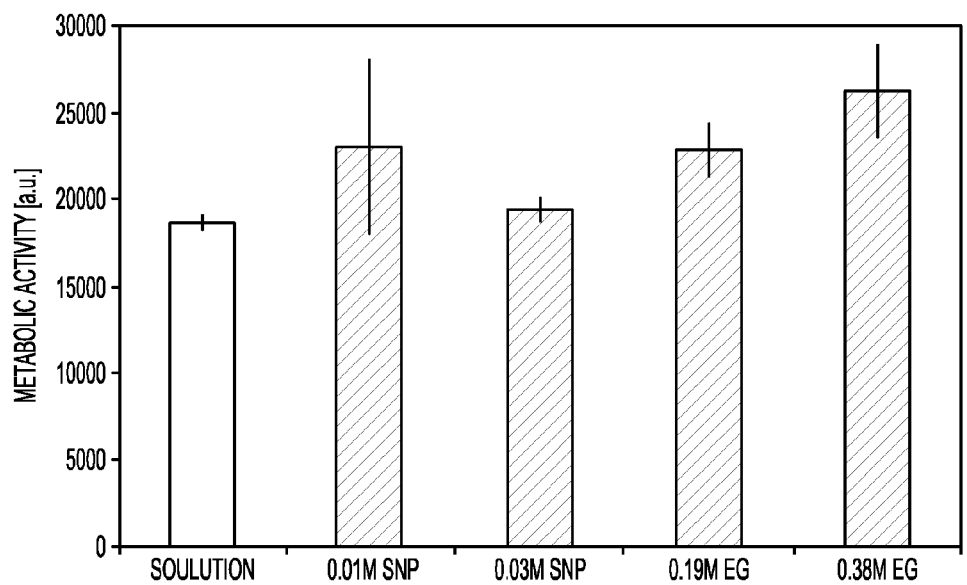

During the encapsulation process, mammalian cells were exposed to individual and aggregated SNPs in the surrounding solutions as gel formation proceeds. SNPs can be mildly cytotoxic. The toxicity of the encapsulation process was analyzed by incubating mammalian cells in 0.01 and 0.03 M SNP solutions. These were the concentrations used in the gels. After 24 h of incubation in the presence of SNPs, the cell membrane integrity and MA was measured. The results showed that exposure to SNPs did not cause membrane damage in HFFs and MEFs. Moreover, cells exposed to SNPs had comparable MA to control cells (FIG. 6).

Another factor for cytotoxicity is the formation of cytotoxic by-products such as EG during the hydrolysis reaction. HFF and MEF cells were incubated with 0.19 and 0.38 M EG to test for cytotoxicity. The concentrations of EG used in these experiments were based on the stoichiometric reaction of 10% (v/v) THEOS assuming a complete reaction. Incubation of HFF and MEF cells in EG for 48 h did not cause any cell membrane damage nor had any effects on the MA of the cells (FIG. 6). FIG. 6 illustrates cytotoxicity of SNPs and EG on: (A) HFF, (B) MEF.

1.3.3) Encapsulation of Mammalian Cells in Pure THEOS Silica Gels

Figure 7:
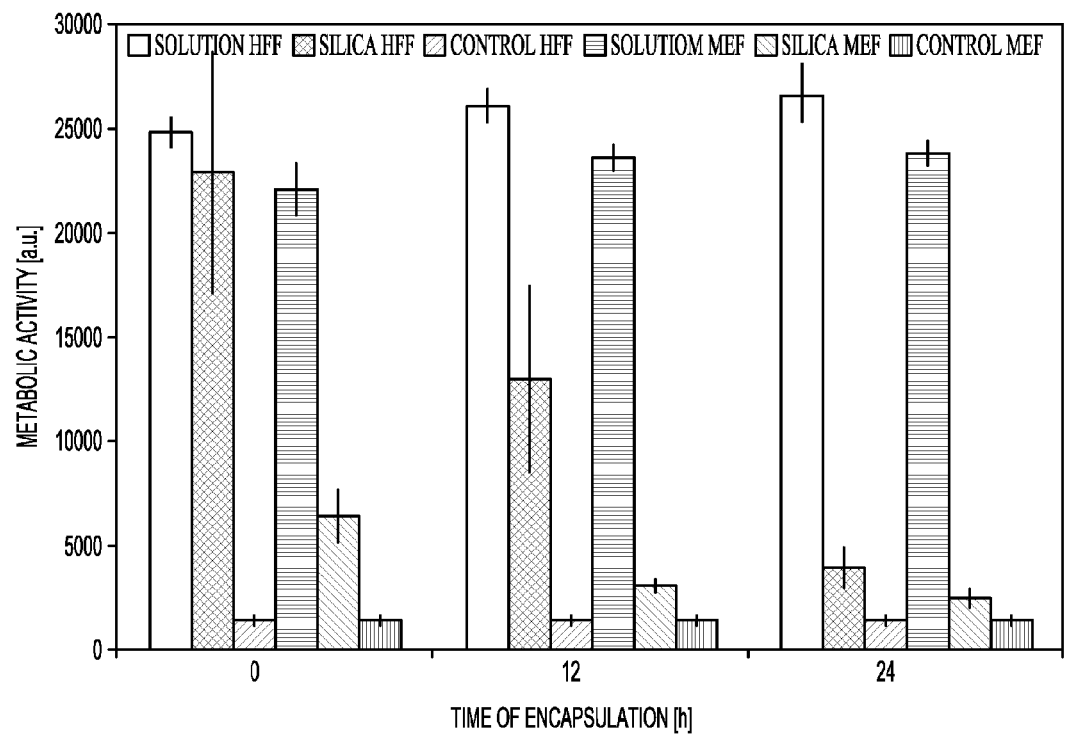
FIG. 7 illustrates metabolic activity of encapsulated HFF and MEF cells, in accordance with various embodiments.

Immediately after encapsulation in pure THEOS gels, the encapsulated HFF cells exhibited about 96.7% of the solution MA, and encapsulated MEF cells exhibited 30% of the solution MA (FIG. 7). The decrease in the MA of the encapsulated cells was statistically significant when compared to the cells in solution (ANOVA, p<0.05). After 12 h of encapsulation, HFFs exhibited only 46.3% of the solution MA. After 24 h of encapsulation, MA of MEF and HFF cells had dropped to practically zero value. The drastic drop of MA of MEFs after encapsulation showed adverse interactions at the biointerface. Cells encapsulated in TMOS gels followed a similar trend.

FIG. 7 illustrates metabolic activity of encapsulated HFF and MEF cells. Negative Controls (blue and green) were prepared by encapsulating dead HFF and MEF cells. Dead cells were prepared by incubation in 70% ethanol for 10 min. Compromised membrane integrity of the dead cells was verified before encapsulation.

The changes in the cell membrane lipid conformation of the encapsulated cells was quantified by monitoring the change in the peak location of the lipid acyl chain stretching peak (v-$CH_2$) at about 2850 $cm^{-1}$. Immediately before the onset of the gel transition, the v-$CH_2$ peak wavenumbers of the cells in the silica sol and the cells in media were almost identical. When the experiments were repeated 30 min after gelation, the encapsulated cells had significantly lower $v\text{-}CH_2$ values than the cells in media (Table 1.1). The decrease in the $v\text{-}CH_2$ wavenumber upon encapsulation shows increased packing of the membrane lipids potentially, due to stiffening of the gel, interactions with the gel surface, buildup of compressive stresses, and partial dehydration of the cells. The change in the cell membrane fluidity with encapsulation was evidenced by the small change in $v\text{-}CH_2$ peak values with changing temperature (Table 1.1). $\Delta v\text{-}CH_2$ between 23° C. and 0° C. was 0.7 cm$^{-1}$ and 0.8 cm$^{-1}$ for HFF and MEF cells, respectively, when they were in solution. When encapsulated, $\Delta v\text{-}CH_2$ decreased 0.5 cm$^{-1}$ for the same change in temperature.

TABLE 1.1

Structural changes in the cellular membranes with encapsulation.

$v\text{-}CH_2$ Peak Location [cm$^{-1}$]

| | 0° C. | | 23° C. | | |
| --- | --- | --- | --- | --- | --- |
| Cell Type | In media | Encapsulated for 1 h | In media | Encapsulated for 1 h | Encapsulated for 6 h |
| HFF | 2851.8 ± 0.01 | 2843.8 ± 0.02 | 2852.3 ± 0.05 | 2844.5 ± 0.14 | 2845.6 ± 0.3 |
| MEF | 2851.5 ± 0.12 | 2843.1 ± 0.17 | 2852.3 ± 0.06 | 2843.6 ± 0.06 | 2844.9 ± 0.5 |
| LNCaP | 2851.8 ± 0.01 | 2843.4 ± 0.00 | 2852.3 ± 0.05 | 2843.9 ± 0.17 | — |
| MCF-7 | 2852.0 ± 0.17 | 2843.1 ± 0.24 | 2852.6 ± 0.02 | 2843.7 ± 0.23 | — |

Increased packing of the cellular membranes with gelation did not have significant short-term effects on membrane integrity. Membrane integrity of encapsulated cells immediately after encapsulation was measured as 98.3±4.2% and 97.2±3.5% for HFFs, and MEFs, respectively. Even though the membrane integrity assay using fluorescence microscopy indicated no membrane damage immediately after encapsulation, significant amounts of cytoplasmic material has leaked from the encapsulated cells. This was observed by LDH release from the encapsulated HFF and MEF cells. After 24 h of encapsulation, there was 78%±1.3% and 80.1%±1.3% LDH release from encapsulated HFFs and MEFs with respect to their lysed controls. Moreover, FTIR analysis of the encapsulated cells conducted after 6 h showed that the $v\text{-}CH_2$ peak positions shifted towards higher wavenumbers (Table 5.1) which was an indication of loosening in membrane packing and therefore membrane damage.

Figure 8:
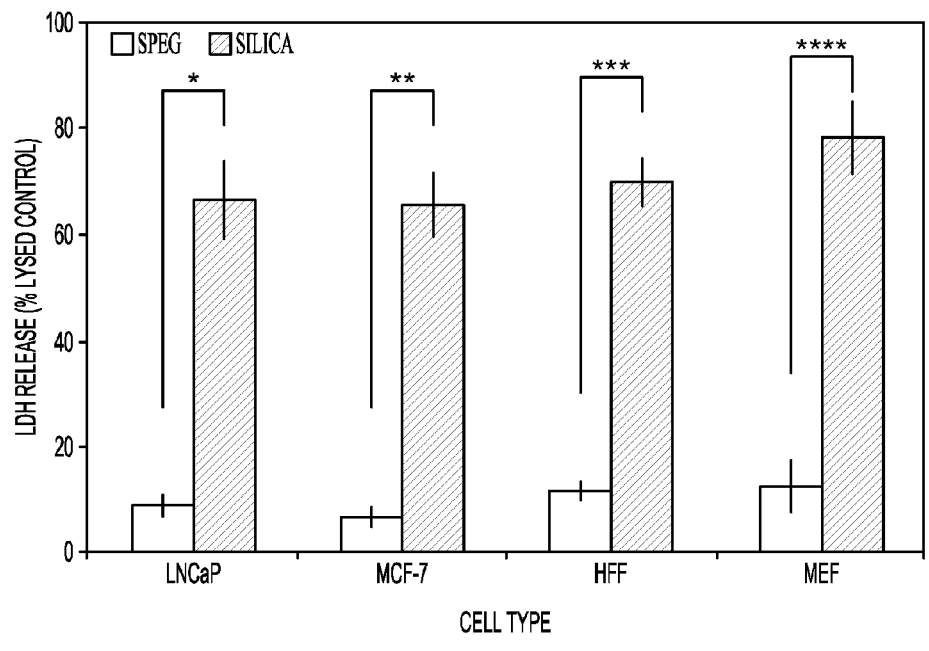
FIG. 8 illustrates LDH release from encapsulated cells after 24 h of encapsulation, in accordance with various embodiments.

FIG. 8 illustrates LDH release from encapsulated cells after 24 h of encapsulation. Statistical analysis was conducted using ANOVA, p<0.05 (n=3). In these experiments, SPEG-4-arm (10%, Mw=2 kDa) was used. Two additional cell lines, LNCaP and MCF-7 cells, were used for comparison.

1.3.4) Encapsulation of Mammalian Cells in SPEG Gels

Figure 9A:
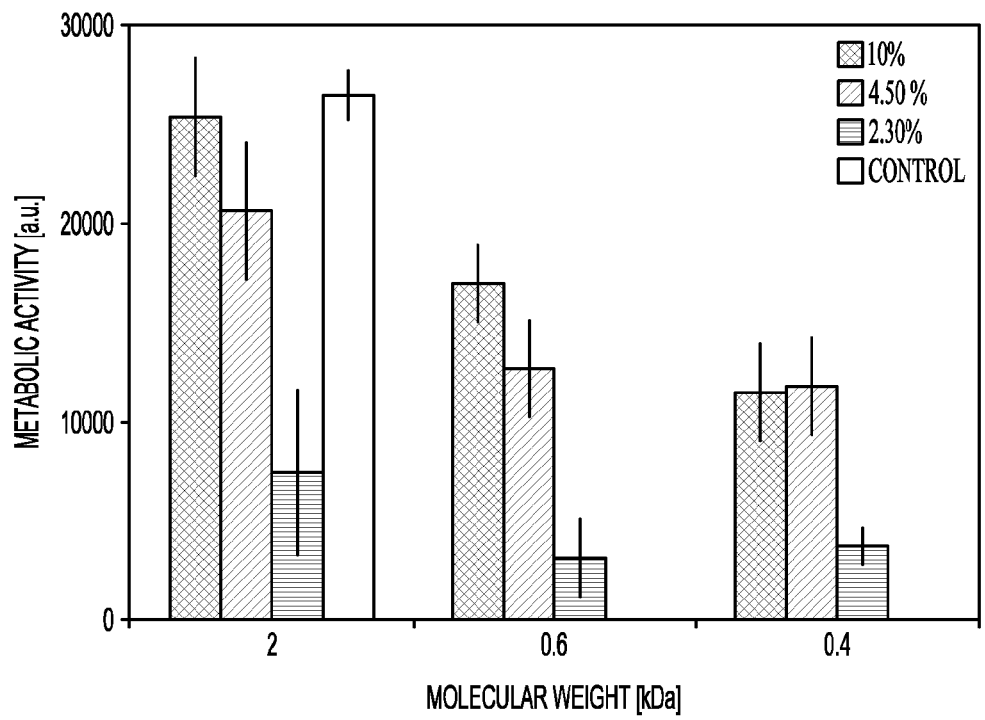
FIGS. 9 (A) and (B) illustrate the metabolic activity of encapsulated cells (A) HFF, (B) MEF, in accordance with various embodiments.
Figure 9B:
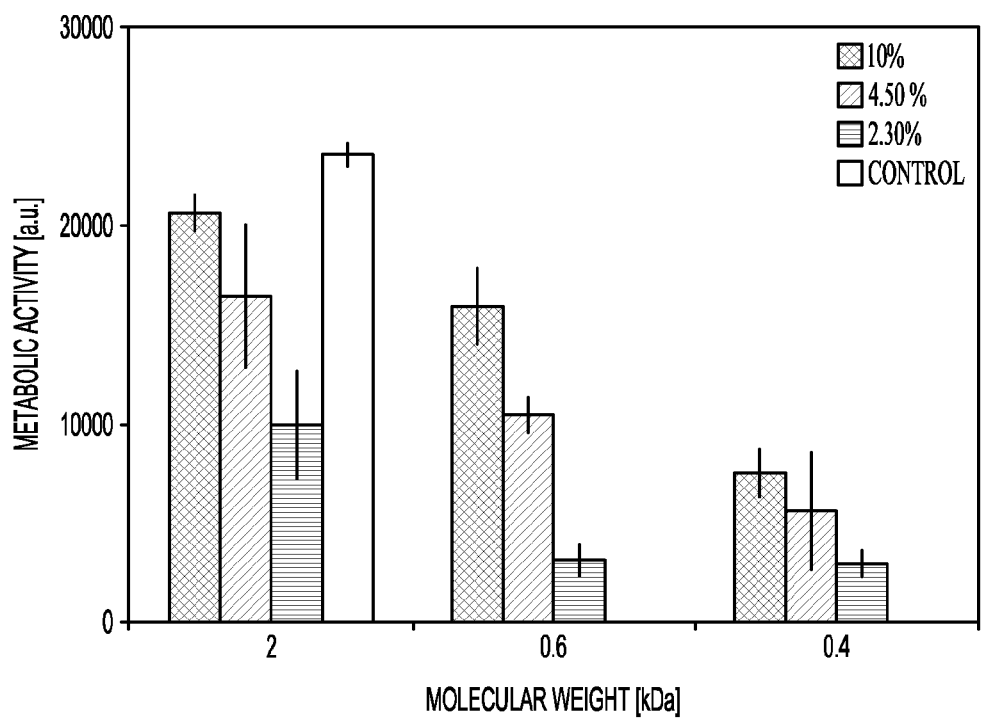

The effect of the incorporation of PEG in the silica matrix (SPEG) was evaluated by monitoring the MA of the encapsulated cells after 24 h of encapsulation. MA of the encapsulated cells depended on the size and concentration of the PEG used in the gel synthesis (FIGS. 9(A) and (B)). Cells encapsulated in 2.3, 4.5, and 10% SPEG-1 gels (0.4 kDa) had the largest drop in MA within 24 h, with reductions of 56.43% and 67.83% for HFF and MEF, respectively. The effectiveness of 0.6 kDa PEG and the 2 kDa PEG in preserving MA of the encapsulated cells depended on their concentration (FIG. 9). However, the drop in MA was always greater in the linear PEGs. This result suggested that PEG was effective in preventing the detrimental interactions of the silanol groups on the lipid membranes. Note that one reason for decreased MA in SPEG-4-arm gel with concentration could be attributed to increased phase separation in the gels. Therefore, in the rest of the experiments 10% SPEG-4-arm gels were used.

FIG. 9 illustrates effect of PEG concentration and size on the metabolic activity of encapsulated cells: (A) HFF, (B) MEF. Cells were incubated at 37° C. and 5% $CO_2$. Cells incubated were used as the control in media.

Figure 10A:
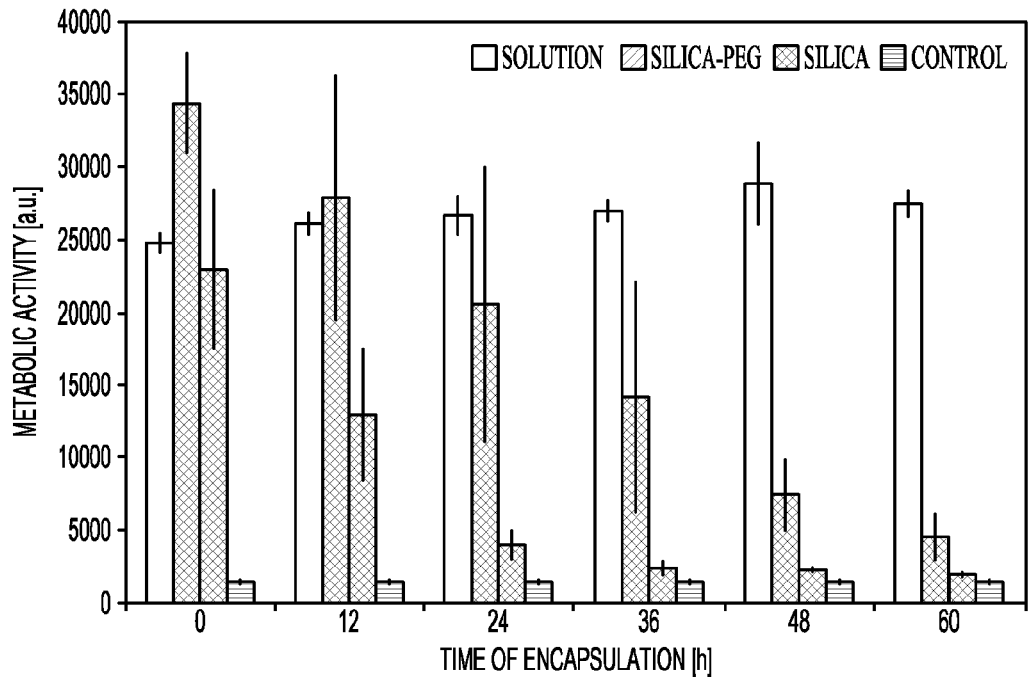
FIGS. 10 (A) and (B) illustrate metabolic activity of encapsulated cells (A) HFF and (B) MEF, in accordance with various embodiments.

The effect of long time encapsulation on MA was significant (FIGS. 10(A) and (B)) even in SPEG gels. However, incorporation of PEG into the silica matrix had a positive effect on the MA of encapsulated cells. This result confirmed that one mechanism of damage to encapsulated cells may be the specific interactions between the silica surface (—SiOH) and the cellular membranes, which could be minimized by incorporating PEG into the gels. The hydrophilic part of PEG forms hydrogen bonds with surface silanol groups. With PEG the time dependent decrease in MA over time slows down, but does not completely stop. This shows that there are other inherent biological factors such as cell growth that are also involved in the decrease of MA.

LDH release from the SPEG-4-arm encapsulated cells after 24 h (FIG. 8) was measured. The amount of LDH released into the extracellular medium is proportional to the number of cells damaged or lysed. Contrary to the results obtained in pure silica gels, encapsulated HFFs and MEFs in SPEG-4-arm gels only had a LDH release of 11.2% and 13.5%, respectively. LDH test results confirmed that the detrimental effect that bare silica surfaces had on encapsulated cells could be inhibited by functionalizing the silica surface with PEG.

Figure 10B:
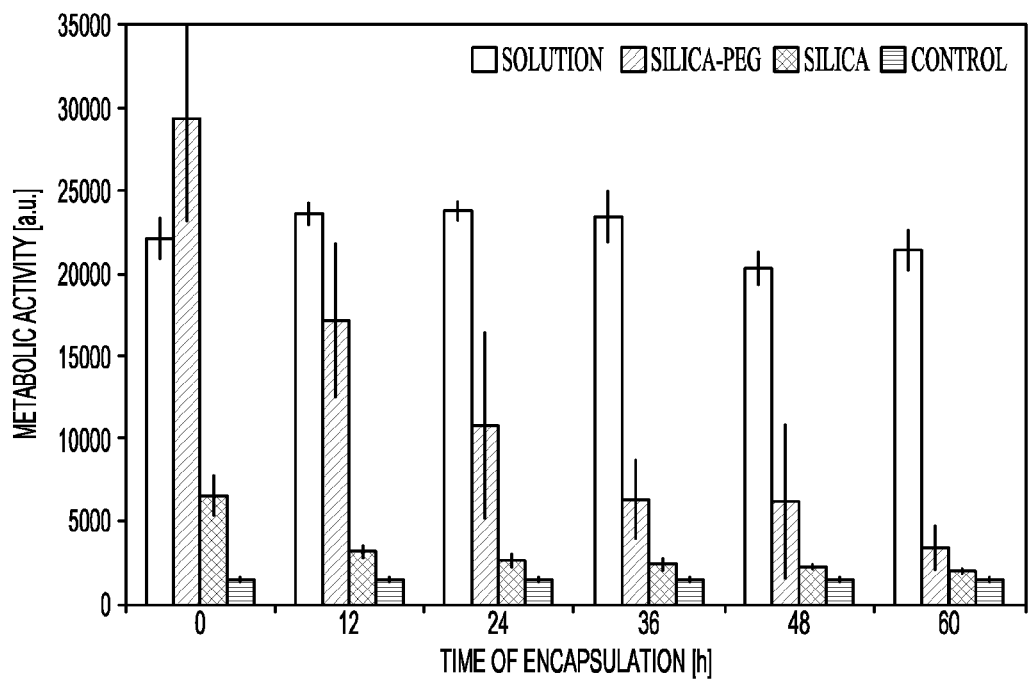

FIG. 10 illustrates metabolic activity of encapsulated: (A) HFF and (B) MEF. Negative controls (blue) were prepared by encapsulating dead HFF and MEF cells. Dead cells were prepared by exposure to in 70% ethanol for 10 min. Compromised membrane integrity of the "dead" cells was verified before encapsulation. Cells incubated at 37° C. and 5% $CO_2$ were used as the positive control.

Figure 11A:
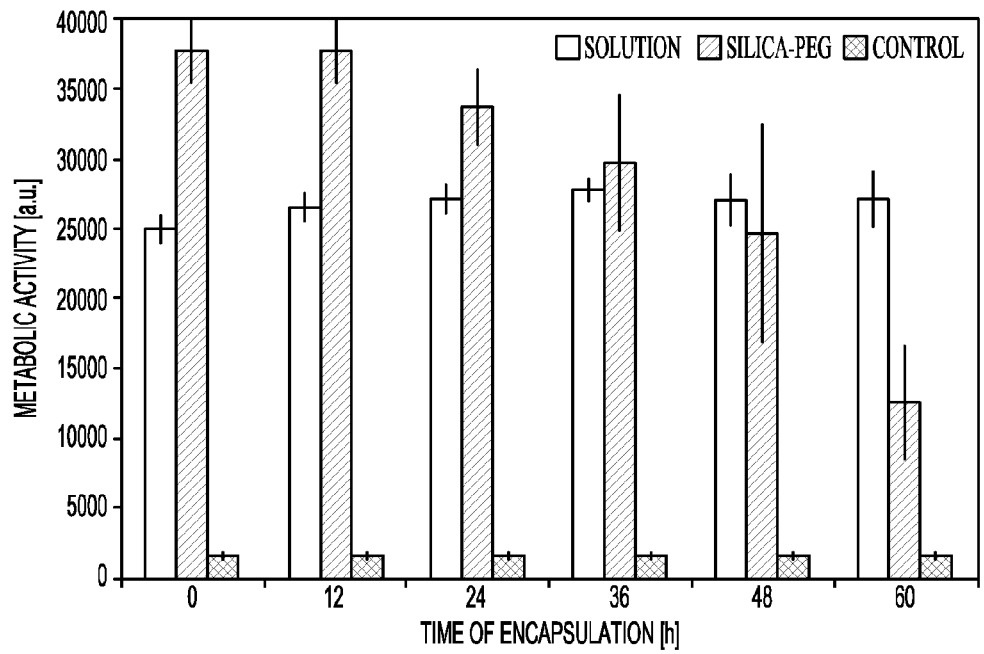
FIGS. 11 (A) and (B) illustrate metabolic activity of encapsulated irradiated cells (A) HFF and (B) MEF, in accordance with various embodiments.
Figure 11B:
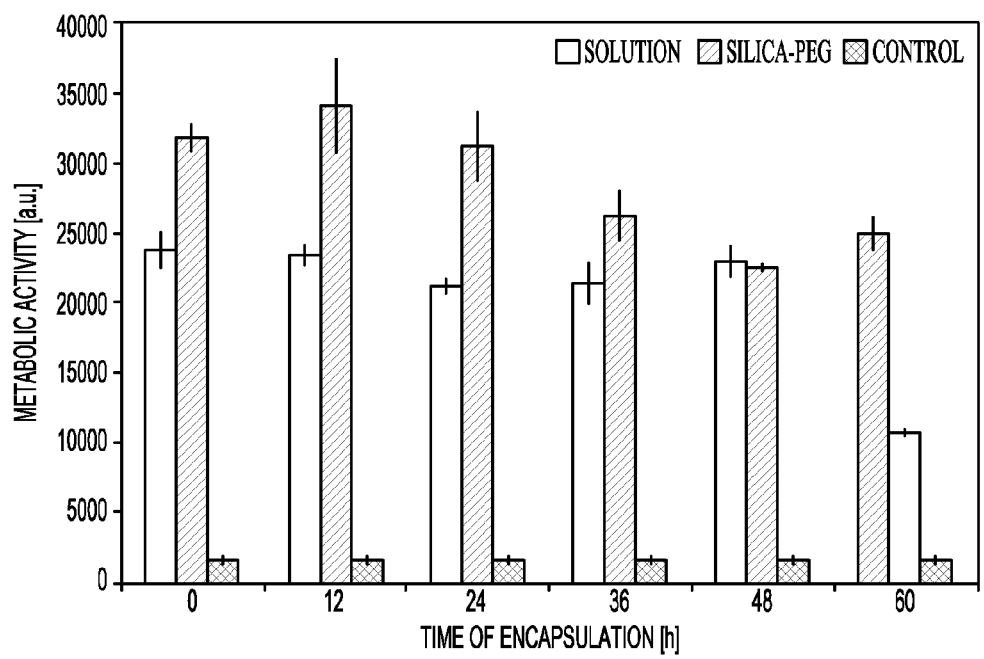

The effect of arrested cellular division in the MA of the SPEG encapsulated cells was also explored. Similar to what was observed with the unirradiated HFFs and MEFs encapsulated in SPEG gels. The encapsulated HFFIR and MEFIR cells were metabolically more active when encapsulated (than in solution) as shown in FIG. 11(A)-(B). When HFFIR cells were encapsulated in SPEG gels there was no decrease in the MA during the first 12 h of encapsulation, and MA decreased by only 11.1% within the first 24 h of encapsulation (p<0.05). 48 h after encapsulation MA of HFFIR was 65%. However, the MA started to drop drastically after 48 h of encapsulation. Similarly, MEFIR cells encapsulated in SPEG gels maintained their MA for 24 h in encapsulation. MA started to drop after 36 h of encapsulation, to 70.9% and 32.4%, after 48 h and 60 h of encapsulation, respectively.

The irradiated cells (HFFIR, and MEFIR) lost over 97% of their MA after 84 h of encapsulation (data not shown).

1.4) Discussion

Even though THEOS is compatible with organic polymers forming hydrogels, SPEG gels exhibited phase separation at certain PEG sizes and concentrations (FIG. 2). The phase separation tendency is determined mainly by the PEG/silica ratio. For SPEG-4-arm gels synthesized with of 2.3% and 4.5% PEG, widespread macroscopic phase separation occurred. It is suggested that phase separation takes place by the adsorption of PEG on silica through hydrogen bonding of the ether oxygens in PEG and the surface silanols such that the surface of the gelling phase becomes hydrophobic and less soluble in the solvent.

In contrast, an increase in concentration above 4.5% in PEG led to a delayed onset of the sol-gel transition, albeit without a noticeable phase separation (FIG. 2(A)), and a uniform structure was obtained. Moreover, in SPEG-1 gels ($M_w$=0.6 kDa or 0.4 kDa) no phase separation was observed (FIG. 2(B)). It is suggested that bridging flocculation between the organic (PEG) and the inorganic silica ($SiO_2$), which causes phase separation, depends on the molecular weight and the concentration of the organic polymer. Therefore, at concentrations above 4.5% for SPEG-4-arm and at all the concentrations of SPEG-1, it is possible that bridging flocculation does not take place since the amount of PEG is enough to sterically stabilize the silica and cover its entire surface. This is supported by the studies conducted using X-ray scattering, where extremum concentrations of PEG (in silica PEG systems) produced stable reactions with no phase separation. However, at intermediate PEG concentrations, the organic polymer absorbs on the silica causing bridging flocculation.

THEOS gels were synthesized using cell culture media as the solvent. SEM characterization showed that the gels were formed by three dimensional aggregation of nanometer size particles with a random distribution of porosity (FIG. 3(A)). These results suggested that the soluble organic components present in the media acted as a catalyst for gelation and served as a template for silica condensation. It was previously shown that albumin, gelatin and casein could form a variety of hybrid nanostructures (e.g., fibrillar, spherical) when combined with THEOS at different pH values. THEOS gels prepared with a cationic agent was also formed by the aggregation of particles of about 10-20 nm in diameter. When PEG was incorporated, an increase in the porosity of the gel was observed. The porosity remained randomly distributed.

FIG. 11 illustrates metabolic activity of encapsulated irradiated cells: (A)

HFF and (B) MEF. Negative controls (blue) were prepared by encapsulating dead HFF and MEF cells, dead cells were prepared by incubation in 70% ethanol for 10 min, and then their membrane integrity was verified with fluorescence microscopy. Cells seeded and incubated at 37° C. and 5% $CO_2$ were used as the positive control (Solution).

In the studies with cells, generally, compositions that did not cause phase separation were used. FTIR analysis of the 3740 $cm^{-1}$ region of pure silica and SPEG gels indicated strong interactions of silanol groups of the silica surface with PEG though hydrogen bonding between the ether oxygens of PEG and the silica surface. This reduced the interactions at the biointerface between the encapsulated cells and the silica gel surface that is shown to be detrimental (FIG. 7). Moreover, transesterification reactions between hydrolyzed alkoxides and PEG may also occur during gelation, therefore, covalent bonding between PEG and silica can also be expected. NMR spectroscopy and Differential Scanning calorimetry (DSC) based studies showed these interactions. However, direct evidence of covalent bonding between the silica and PEG through FTIR analysis was not obtained. Not intending to be limited by any theory of operation, the following two equations show examples, in some embodiments, of covalent interactions that can occur.

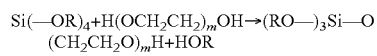

1.4.1) Encapsulation of Mammalian Cells in Pure Silica Gels

It is known that the morphology and surface of silica nanoparticles can affect cell membrane integrity by oxidative stress, cell membrane damage and by inducing possible cell apoptosis/necrosis. Therefore, it is possible that after the silica gel forms, encapsulated cells experience a combination of these detrimental stresses and their MA decreased. Viability of mammalian cells encapsulated in silica gels has not been extensively explored; most of the published studies have focused on measuring the viability of the encapsulated cells immediately after encapsulation.

Using IR spectroscopy the structural changes in cellular membranes after encapsulation were determined by analyzing the peak position of the $v$-$CH_2$ band (~2850 $cm^{-1}$). For cells in solution, the cellular membranes are in the liquid-crystalline phase, characterized by increased lipid head group spacing, increasing disorder in acyl chains and a decreased bilayer thickness. When the silica precursors gel, there is an abrupt change in its viscosity. This is reflected on the $v$-$CH_2$ peak position as it shifts towards lower wavenumbers (~2844 $cm^{-1}$). The decrease in the $v$-$CH_2$ wavenumber reflects an increased packing of the membrane lipids, indicating a transition of the encapsulated cell membranes into a gel phase. The gel phase of the lipid membrane is characterized by a decrease in lipid head group spacing and decreased membrane permeability. In the short term, increased packing of the encapsulated cell membranes did not have a significant effect on membrane integrity as indicated by fluorescent measurements (FIG. 12).

FIG. 12 illustrates fluorescence microscopy micrographs of encapsulated cells. Images were collected after encapsulation. Gels were prepared with 10% (v/v) THEOS. (A) and (C) HFF and MEF cells in pure silica gel, respectively. (B) and (D) HFF and MEF cells in 10% SPEG-4-arm gel, respectively.

The stress of encapsulation in silica gels can result in change in membrane permeability. For mammalian cells, it was found that even though there was a change in the fluidity of the cellular membranes (i.e., drop of $v$-$CH_2$ peak position), cells stayed metabolically active after encapsulation (FIG. 7). Therefore, it is possible that encapsulation induced further changes in the already altered cellular membranes. It has been hypothesized that hydrogen bonding interactions between silanol surface sites (—SiOH) and the negatively charged lipid head groups (e.g., —$PO_4^-$) or the negatively charged membrane proteins result in conformational changes in the lipid membranes, leading to their disruption. There were two important findings in the results that supported this hypothesis: (1) there was a shift in $v$-$CH_2$ peak position by 1.1 and 1.3 $cm^{-1}$ for encapsulated HFF and MEF cells, respectively after encapsulation, and (2) LDH released into the surrounding media indicates excessive increase in permeability of the membranes.

Rigidity of the silica matrix mechanically constrains the encapsulated cells, and as a result, cellular division and growth are inhibited. It has been shown that only certain types of bacterial and plant cells are able to perform cellular division after silica encapsulation. The observations of encapsulated cells over time showed that cells wanted to increase their size towards the rigid matrix in their intention to complete cellular division. Thus, a damaged cellular membrane of the encapsulated cells was not only caused by the silica surface interactions but also by the intrinsic cellular behavior. This hypothesis was further corroborated in experiments with encapsulated cells where cellular division was arrested by irradiation. Within the first 12 h the irradiated cells showed increased MA when compared to the normal cells (FIG. 7). These results show the presence of multiple factors that affect long term viability for encapsulated cells.

1.4.2) Encapsulation of Mammalian Cells in SPEG Gels

There is a significant improvement in viability and MA of encapsulated prokaryotic and eukaryotic cells when a biocompatible-polymer interface between the cells and the silica surface is constructed. Recently, encapsulation of mammalian cells in SNP's surface functionalized with lysine groups at their surfaces has been reported. Moreover, the encapsulation of clusters of cells in hydrolyzed alkoxides has been shown. However, these studies did not measure the viability and MA of the encapsulated cells over time. In this study, the non-specific interactions between the cellular membranes and the silica surface were mediated by the incorporation of PEG (SPEG gels), and the effect in the membrane structure and MA of encapsulated cells were monitored.

1.5) Conclusion

The use of tetrakis (2-hydroxyethyl) orthosilicate (THEOS), a water soluble alkoxide, for the encapsulation of mammalian cells, is reported. This precursor allowed polymerization of silica at pH 7.4 using the cell culture media as a solvent. Silica monoliths for alkoxide concentrations as low as 10% (v/v) were obtained. The cytotoxicity of EG was tested using membrane integrity and MA assays, which indicated that the majority of the cells survive the encapsulation process. Cells were also encapsulated in silica gels synthesized from TMOS to show that the detrimental effects in the viability and MA were independent of the silica precursor used.

After encapsulation in silica gels, a conformational change in the membrane of cells occurred, in which the cellular membranes underwent a change to a more compact lipid structure. The results indicated that at the new conformational state of the cellular membranes, cells still remained MA. However, there was a drastic drop in the MA of cells over time, which was attributed to two factors: (1) non-specific surface interactions between the cellular membranes and surface silanol groups, and (2) the intrinsic cellular behavior that tried to undergo cellular division in a confined environment.

The influence of factors (1) and (2) in the MA of encapsulated cells was further investigated. For factor (1), the surface chemistry of the silica matrix ($\equiv$SiOH) was changed with the incorporation of a biocompatible polymer (PEG). For factor (2), cellular division of cells was arrested prior to the process of encapsulation by an irradiation protocol. The MA activity of the irradiated cells in SPEG gels showed to be the highest MA over time for all the conditions tested. Therefore, factors (1) and (2) played a role in maintaining viable cells.

2.0. Development of Thixotropic Silica Gels for Reversible Encapsulation of Cancer Cells 2.1) Summary In Section 1, silica precursors (e.g., silica alkoxides, silica nanoparticles), organic macromolecules and polymers were described for the production of a porous gel. These porous gels were at first considered irreversible since after gelation, they formed a stiff and sturdy monolith structure encapsulating cells or macromolecules. One of the objectives of Section 2.0 was to investigate induction of thixotropic behavior in silica gels. Thixotropy is the property of certain gels that are viscous under normal conditions, but become less viscous over time when shaken, agitated, or stressed. It was possible to achieve thixotropic behavior of silica gels by modifying certain steps of gel synthesis and by using different organic polymer components.

A thixotropic gel (reversible gel) structurally includes micrometer-size particles rich in hydrogen bonding sites thanks to silanol and hydroxyl groups on their surface (FIG. 13). An advantage of thixotropic silica gels includes that they allow the recovery of the encapsulated cells on demand. The experiments demonstrated that novel applications for three dimensional cell culture, reversible cell encapsulation, drug delivery systems, and preservation of cells could be developed.

In Section 2.0, the encapsulation of cancer cells and normal cell lines in SPEG-4-arm and reversible silica gels was investigated. The results showed a differential response in the metabolic activity (MA) of encapsulated cancer and normal cell lines. While normal cells maintained MA for up to 3 days, cancer cell lines were able to maintain MA for up to 1 week. This surprising result spurred an investigation of using SPEG-4-arm and reversible gels for the development of a screening cancer cell tool from tumors.

2.2) Materials and Methods

Tetraethyl orthosilicate (TEOS), sodium silicate (27 wt % $SiO_2$, 10 wt % NaOH), and silica nanoparticles in powder (Cab-O-Sil, grade M5) were purchased from Sigma (St. Louis, Mo.). Nanoparticles were used to increase hydrogen bonding between the microparticles of the gel (e.g., gel microparticle—nanoparticle—gel microparticle hydrogen bonding, for example). Different precursors were used to form hybrid composites with tunable characteristics: Multi-arm PEG ($M_w$=2 kDa), linear PEG ($M_w$=10 or 20 kDa), dextran ($M_w$=40 or 100 kDa), and trehalose (Mw=378.33 Da).

FIG. 13 shows a schematic representation of a thixotropic transition. PEG can be replaced with any polymer capable of forming hydrogen bonds with $SiO_2$.

2.2.1) Thixotropic Gel Synthesis

To make thixotropic gels, the alkoxide precursor (e.g., TEOS) was hydrolyzed at a volume ratio of 1:9, 1:7, and 1:4.5 alkoxide:water in the presence of an acid (e.g., acetic acid) as a catalyst for the alkoxide hydrolysis. Separately, 4-arm PEG ($M_w$=2 kDa) was mixed with silica nanoparticles (e.g., 0, 5, 10, or 15% w/w). Later, the pre-hydrolyzed alkoxide and the PEG solutions were mixed by vortexing for 5 min. The volume ratios of alkoxide:PEG can be kept at 1 or below to help avoid precipitation or phase separation of the material. The final pH of the solution was adjusted to 7. The material was left to gel for 48 h at ambient temperature until a solid monolith was formed. Water was then added on the monolith and the material was gently grinded with pipeting to form micrometer size particles. The particle suspension was then centrifuged at 1500 RPM for about 5 min in order to remove the excess water added during the grinding step. The precipitate present was aggregates of micrometer size that form the thixotropic gel. In other formulations, trehalose was used instead of PEG (Table 2.1).

When sodium silicate was used as the silica precursor, 1.2 g of dextran ($M_w$=40 or 100 kDa) was first mixed with 3.7 ml of 2 M acetic acid and 3.7 ml of water. Later, 500 mg of silica nanoparticles were added to the solution. The solution was stirred for 30 min. A solution of sodium silicate (e.g., 1.5, 2, 2.5, 3, or 3.5 M) was added dropwise while stirring. The mixture was then transferred into a convection oven at 37° C. for 24 h. Grinding was not used on the resultant material since it did not form a monolith; rather, an opaque slurry solution was formed. The resultant mixture was centrifuged at 1500 RPM for 5 min to remove the excess water. In certain formulations, dextran was replaced with PEG ($M_w$=10 or 20 kDa) (Table 2.2).

2.2.2) Characterization of the Thixotropic Gels

Selected gels shown in Tables 2.1 and 2.2 were characterized using Scanning Electron Microscopy (SEM) and rheometry. Sample preparation for SEM analysis is as described herein. Sweep strain tests were conducted to determine the linear viscoelastic regime of the gels. Also, sweep stress tests were conducted to determine the apparent yield point stress (transition from the gel to the liquid state). Moreover, the values of the storage modulus were used for comparison of the stiffness of the different reversible gels produced. The measurements were done with an Ares AG2 Rheometer from TA Instruments (North Castle, Del.). The tests were performed using a conical plate of 40 mm of diameter 2° steel cone at a truncation gap distance of 49 μm, as indicated in FIG. 14. All the measurements were conducted at 25° C.

FIG. 14 illustrates a schematic representation of the rheometer set up for different type of measurements.

2.2.3) Cell Culture and Encapsulation

Cell culture protocols used for human (HFF) and mouse embryonic fibroblasts (MEF) are described as follows: DMEM growth medium was supplemented with 10% FBS; cells were incubated at 37 C in a 5% $CO_2$ incubator until they reached 70-80% confluence. Human umbilical vein endothelial cells (HUVEC), were obtained from ATCC. HUVEC were cultured in F-12K growth medium containing 10% FBS and supplemented with 0.1 g/ml of heparin and 0.05 mg/ml of endothelial cell growth supplement (ECGS).

The cancer cell lines were cultured as follows: Ovarian cancer cells (OVAR-5) were obtained from Dr. Amy Skubitz from the Laboratory Medicine and Pathology Department at the University of Minnesota. OVCAR-5 cells were cultured in RPMI-1640 growth medium supplemented with 10% fetal bovine serum (FBS). Breast adenocarcinoma cells (MCF-7) were obtained from ATCC (Manasas, Va.). MCF-7 cells were cultured in minimum Eagle's medium (MEM) supplemented with 10% FBS, and 0.01 g/ml bovine insulin. The cell culture protocol for LNCaP cells is described herein. All growth medium for the different cell lines were supplemented with 1% Penicillin/Streptomycin.

For reversible cell encapsulation, HFFs or MEFs were suspended in their own growth media at a concentration of 4500 cells/μl. The thixotropic gel was vortexed to transition into a liquid state, and then the cell suspension was added (for gel compositions used see Table 6.1). In a typical experiment 200 μl of the gel was liquefied ("sol") by vortexing for 60 s. To the liquid "sol" 40 μl of the cell suspension was added. The cells were gently distributed in the reforming gel by pipeting in the sol. Gelation (or regelation) was complete within minutes. After gelation, culture media was added on the gel. To extract the cells from the gel, excess volume of culture media was added to the gel (the volume ratio was 1:5 gel:media). Immediately, the suspension of the cells and the particles was filtered through a cell strainer. Most of the cells were captured in a petri-dish with cell culture media, while the particles remained in the cell strainer. One dye was Hoescht which stained the nucleus of all cells (alive and dead). The other dye was propidium iodide which only stained dead cells (cells that have a compromised cellular membrane). The different cancer cell lines were encapsulated in the SPEG gels (encapsulation procedure described in Section 1), and in the reversible gels (see Table 2.3).

TABLE 2.1

Reversible gels produced using 4-arm, 2 kDa PEG and trehalose, using 0.15M acetic acid as catalyst.

| Gel Name | Hydrolysis Ratio (v:v) | Alkoxide:PEG Ratio (v:v) | % SNP (w/w) |
|---|---|---|---|
| A1 | 1:9 | 0.60 | 0 |
| A2 | 1:9 | 0.60 | 5 |
| A3 | 1:9 | 0.60 | 10 |
| A4 | 1:9 | 0.60 | 15 |
| A5 | 1:7 | 0.60 | 0 |
| A6 | 1:7 | 0.60 | 5 |
| A7 | 1:7 | 0.60 | 10 |
| A8 | 1:7 | 0.60 | 15 |
| A9 | 1:4.5 | 0.60 | 0 |
| A10 | 1:4.5 | 0.60 | 5 |
| A11 | 1:4.5 | 0.60 | 10 |
| A12 | 1:4.5 | 0.60 | 15 |

| Gel Name | Hydrolysis Ratio (v:v) | Alkoxide:Trehalose (v:v) | % SNP (w/w) |
|---|---|---|---|
| B1 | 1:9 | 0.60 | 2.5 |
| B2 | 1:10 | 0.60 | 3 |
| B3 | 1:11 | 0.60 | 5 |

TABLE 2.2

Reversible gels produced using linear organic polymers, using acetic acid as catalyst

| | Organic Precursor | | | | Inorganic Precursor | | | | Additive | |
|---|---|---|---|---|---|---|---|---|---|---|
| | Polymer | Size [kDa] | % Weight | Volume [ml] | Concentration [M] | Precursor | Volume [ml] | Concentration [M] | Solvent [ml] | Type | % Weight |
| D1 | Dextran | 35-45 | 7.7 | 3.7 | 2 | Sodium silicate | 1.85 | 1.5 | 8.85 | SNP | 3.1 |
| D2 | Dextran | 35-45 | 7.7 | 3.7 | 2 | Sodium silicate | 1.85 | 2 | 8.85 | SNP | 3.1 |
| D3 | Dextran | 35-45 | 7.7 | 3.7 | 2 | Sodium silicate | 1.85 | 2.5 | 8.85 | SNP | 3.1 |
| D4 | Dextran | 35-45 | 7.7 | 3.7 | 2 | Sodium silicate | 1.85 | 3 | 8.85 | SNP | 3.1 |
| D5 | Dextran | 35-45 | 7.7 | 3.7 | 2 | Sodium silicate | 1.85 | 3.5 | 8.85 | SNP | 3.1 |
| D6 | Dextran | 35-45 | 7.7 | 3.7 | 2 | Sodium silicate | 1.85 | 4.5 | 8.85 | SNP | 3.1 |
| D7 | Dextran | 100 | 7.7 | 3.7 | 2 | Sodium silicate | 1.85 | 1.5 | 8.85 | SNP | 3.1 |

TABLE 2.2-continued

Reversible gels produced using linear organic polymers, using acetic acid as catalyst

| | Organic Precursor | | | | | Inorganic Precursor | | | | Additive | |
|---|---|---|---|---|---|---|---|---|---|---|---|
| | Polymer | Size [kDa] | % Weight | Volume [ml] | Concentration [M] | Precursor | Volume [ml] | Concentration [M] | Solvent [ml] | Type | % Weight |
| D8  | Dextran | 100 | 7.7 | 3.7 | 2    | Sodium silicate | 1.85 | 2    | 8.85 | SNP | 3.1 |
| D9  | Dextran | 100 | 7.7 | 3.7 | 2    | Sodium silicate | 1.85 | 2.5  | 8.85 | SNP | 3.1 |
| D10 | Dextran | 100 | 7.7 | 3.7 | 2    | Sodium silicate | 1.85 | 3    | 8.85 | SNP | 3.1 |
| D11 | Dextran | 100 | 7.7 | 3.7 | 2    | Sodium silicate | 1.85 | 3.5  | 8.85 | SNP | 3.1 |
| D12 | Dextran | 100 | 7.7 | 3.7 | 2    | Sodium silicate | 1.85 | 4.5  | 8.85 | SNP | 3.1 |
| P1  | PEG     | 20  | 7.7 | 3.7 | 2    | Sodium silicate | 1.85 | 5.73 | 8.85 | SNP | 2.5 |
| P2  | PEG     | 20  | 7.7 | 3.7 | 2    | Sodium silicate | 1.85 | 5.73 | 8.85 | SNP | 4.9 |
| P3  | PEG     | 10  | 5.1 | 2.5 | 0.01 | TMOS            | 1.25 | —    | —    | SNP | 0.0 |
| P4  | PEG     | 10  | 5.1 | 2.5 | 0.01 | TMOS            | 1.25 | —    | —    | SNP | 0.5 |
| P5  | PEG     | 10  | 5.1 | 2.5 | 0.01 | TMOS            | 1.25 | —    | —    | SNP | 1.5 |
| P6  | PEG     | 10  | 5.1 | 2.5 | 0.01 | TMOS            | 1.25 | —    | —    | SNP | 2.5 |

2.3) Results and Discussion

The thixotropic gel mainly consisted of a silica precursor and an organic polymer. The gelation process was due to the aggregation of micrometer sized particles, or spheres by inter-particle hydrogen bonding (FIG. 13). When sodium silicate was used as a silica precursor along with linear PEG ($M_w$=10 or 20 kDa), the particulate material that formed consisted of aggregation of sphere-like clusters of particles as indicated in FIG. 15(A). This gel required minimal grinding. On the other hand, when an alkoxide precursor such as TEOS along with 4-arm PEG or sodium silicate with dextran was used, a one piece monolith was obtained. The monolith required extensive grinding to form small particles. FIG. 15(B) shows the heterogeneous sizes and shapes of the particles produced from these gels. All the gels formed from sphere-like aggregates exhibited limited thixotropicity when compared to the gels formed with heterogeneous aggregates.

FIG. 15 illustrates SEM images of gels: (A) Formed of sphere-like particle aggregates (A1), (B) Formed by heterogeneous particles (D1).

2.3.1) Rheology of the Thixotropic Gels

Figure 16:
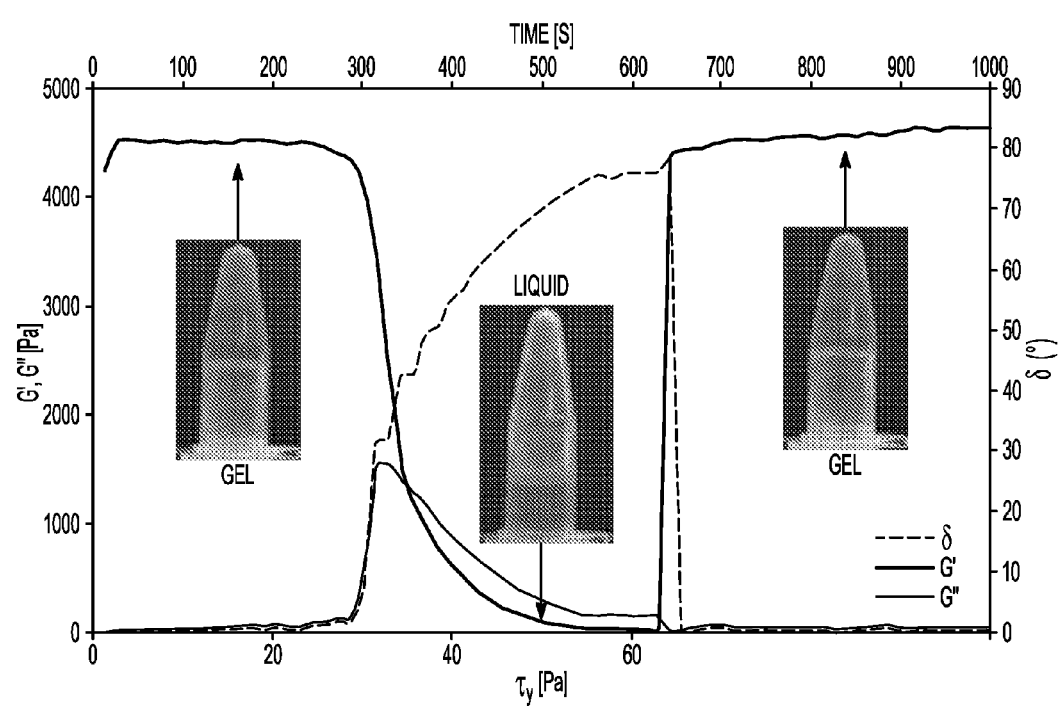
FIG. 16 illustrates G', G", and δ versus time and $\tau_y$, in accordance with various embodiments.

Viscoelastic characteristics of the thixotropic gel depended strongly on the type and concentration of the precursors. FIG. 16 shows the typical response of a thixotropic silica-dextran gel when an oscillatory shear stress is applied. The gel shown is D2 from Table 2.2.

FIG. 16 shows the transition of the storage modulus G' (elastic component), the loss modulus G" (viscous component) and δ (phase angle between G' and G"). An increase in G' is an indicator that a three dimensional network is formed by the aggregation of the colloidal particles and their hydrogen bonding. The reduction in G' reflects a decrease in the hydrogen bonding interactions between particles that form the gel network structure. FIG. 15 also shows the time evolution of G', G", and δ when a shear stress was applied. The apparent yield point stress was obtained by stress sweep experiments. In the gel state, G' was larger than G" and δ was lower than 45°. The gel starts to be liquefied when G'=G". In the liquid state, G' is less than G" while δ is larger than 45°. The stress value at which the gel transitions into a liquid is known as the yield point stress.

Figure 17:
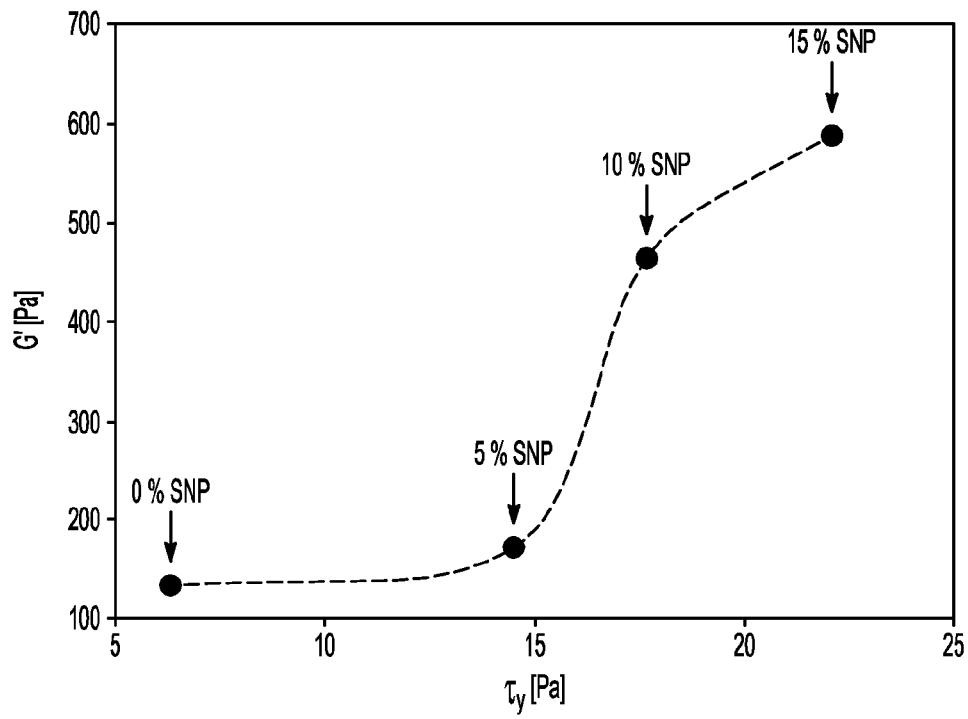
FIG. 17 illustrates G' versus $\tau_y$, in accordance with various embodiments.
Figure 18:
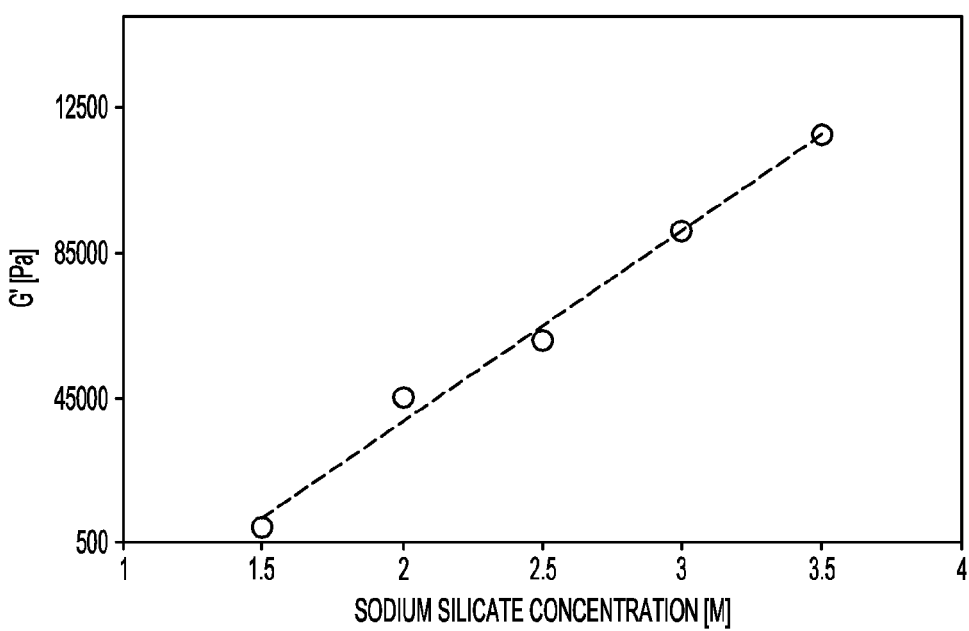
FIG. 18 illustrates G' versus sodium silicate concentration, in accordance with various embodiments.

The incorporation of cells into the reversible gels reduced their strength. Some gels were weakened to such an extent that they were not able to maintain their integrity after the addition of cell culture media. Therefore, Cab-O-Sil, a thickening and thixotropic agent, was added to the formula. Incorporation of different weight ratios of Cab-O-Sil increased the plateau value of the G' and shifted the apparent yield point stress to higher values (FIG. 17). For gels that contained dextran or PEG ($M_w$=10 or 20 kDa) changing Cab-O-Sil concentrations produced precipitation of the sodium silicate. Therefore, a maximum amount of 800 mg of Cab-O-sil was used. In these gels, the concentration of the silica precursor was varied to change the plateau value of G' (FIG. 18). In general thixotropic gels made with dextran gels were stiffer than the gels made with 4-arm PEG. Dextran gels allowed the incorporation of up to 50% of water respect to gel volume, while 4-arm PEG only allowed up to 20%. However, stiffness of the gels was not the only consideration. Even though the dextran gels were stiffer, they were not used for the encapsulation of mammalian cells since presence of excess $Na^+$ induced osmotic stress on the cells, damaging and killing them.

FIG. 17 illustrates an effect of Cab-O-Sil concentration on the plateau value of G'. Gels A1 to A4 from Table 2.1 were used. FIG. 18 illustrates an effect of sodium silicate concentration on the plateau value of G'. Gels D1 to D5 from Table 2.2 were used.

2.3.2) Reversible Encapsulation of Mammalian Cells

Figure 19A:
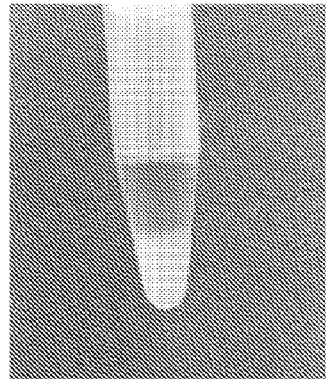
FIG. 19 (A) illustrates encapsulated cells in gel with culture media on top, in accordance with various embodiments.
Figure 19B:
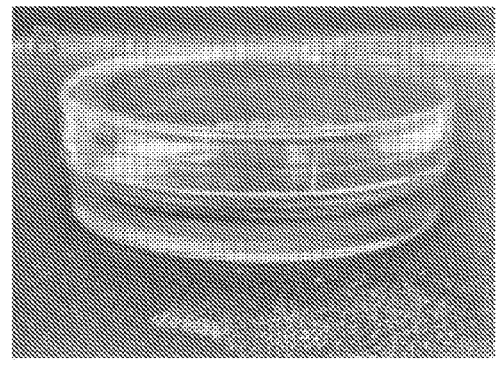
Figure 19C:
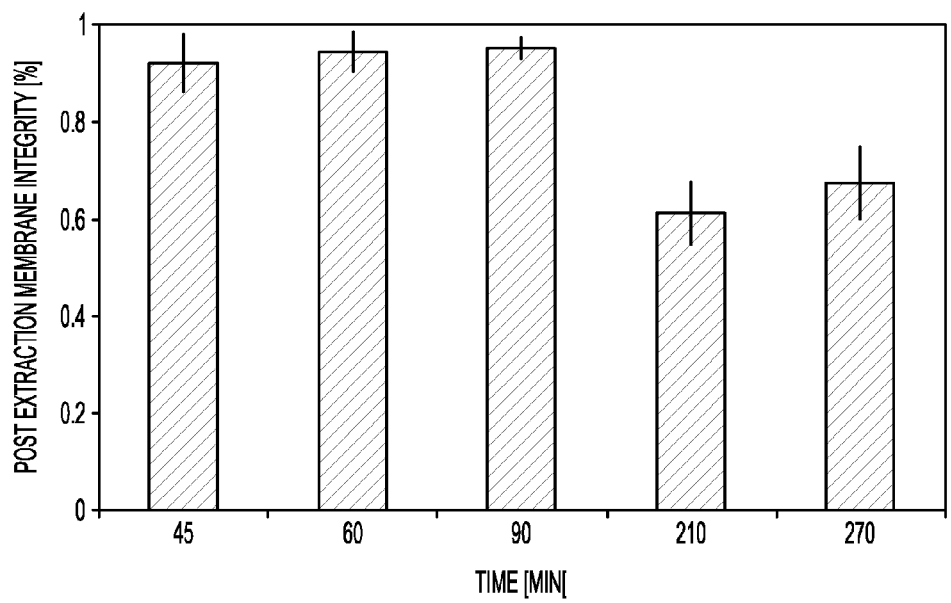
Figure 19D:
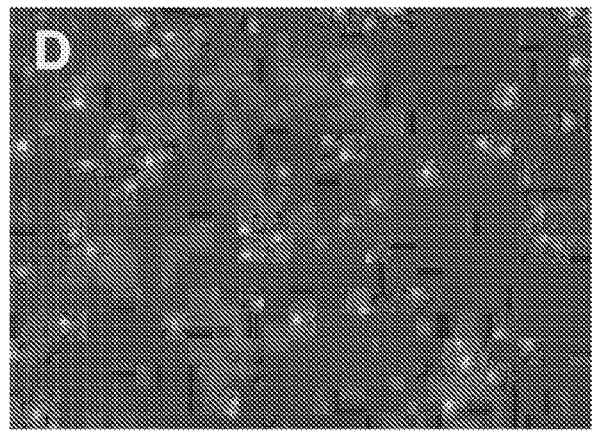
Figure 19E:
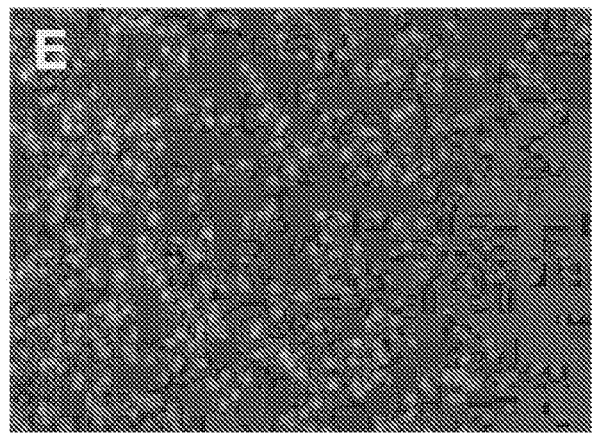
Figure 19F:
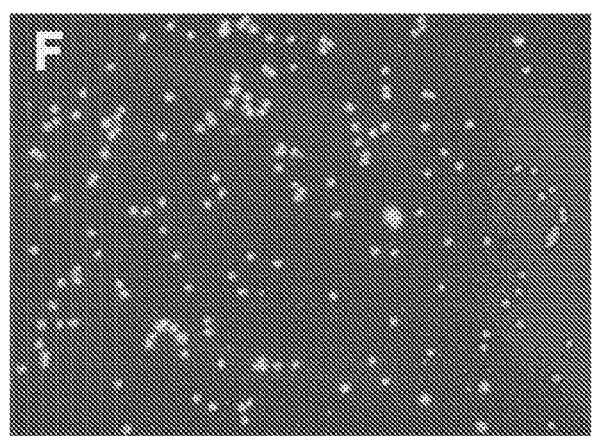

HFF cells were encapsulated in an A3 gel following the procedures described in section 2.2.3 above. After gelation, 150 µl of media was added on top of the encapsulated cells (FIG. 19(A)). The thickness of the gel in the test tube was approximately 10 mm. The gels were stable in cell culture media. Encapsulated cells were incubated at 37° C. and 5% $CO_2$. The cells were extracted at different time points following the procedure described in the previous section. The gel was gently pipetted to disassemble the gel and to release the cells. A cell strainer was used to filter the cells out of the solution that contained the gel particles. The strained cells were collected in a petri dish in the presence of excess media (FIG. 19(B)). Post extraction membrane integrity of the cells was assayed with fluorescence microscopy (see Section 1 for details). The results indicated that during the first 90 min the membrane integrity remained within 93±2% of the control value measured with cells in suspension (FIG. 19(C)). However, within 210-270 min of encapsulation the membrane integrity dropped to approximately 60±3.5%.

2.3.3) Encapsulation of Cancer Cells in Silica-PEG (SPEG) Gels

Different types of cancer cell lines were encapsulated in SPEG-4-arm gels ($M_w$=2 k Da). It was discovered that there was a differential response in the metabolic activity (MA) of cancer cells with respect to normal cells when they were encapsulated in these gels. The results indicate that mechanical inhibition of proliferation can be utilized to selectively enhance the survival of cancer cells in a tissue-like environment.

The results show that anchorage-dependent cancer cell lines adapted better to the conditions imposed by encapsulation, where cellular division was inhibited. LNCaP cells, MCF-7 cells, and OVCAR-5 cells stayed metabolically active for up to 2 weeks after encapsulation.

Figure 20A:
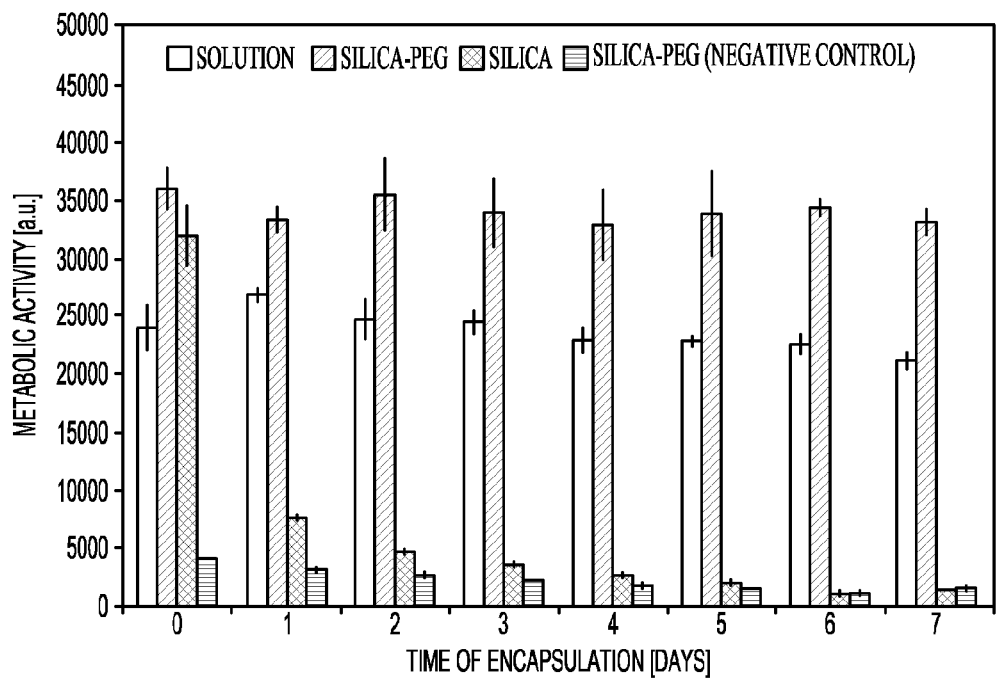
FIGS. 20 (A), (B), and (C) illustrate metabolic activity versus time for cancer cell lines encapsulated in gels, in accordance with various embodiments.
Figure 20B:
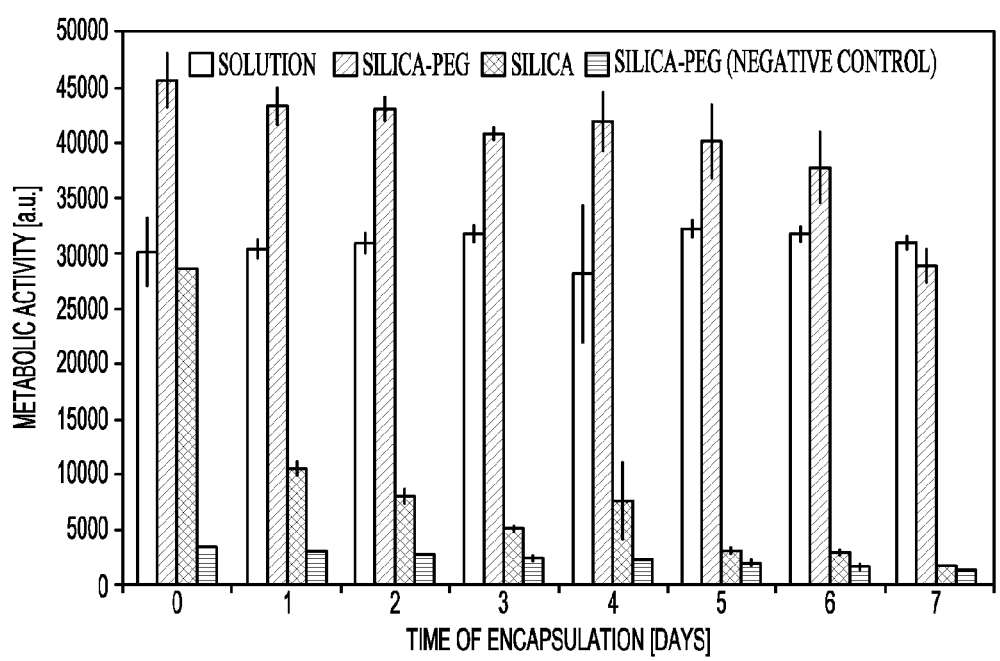
Figure 20C:
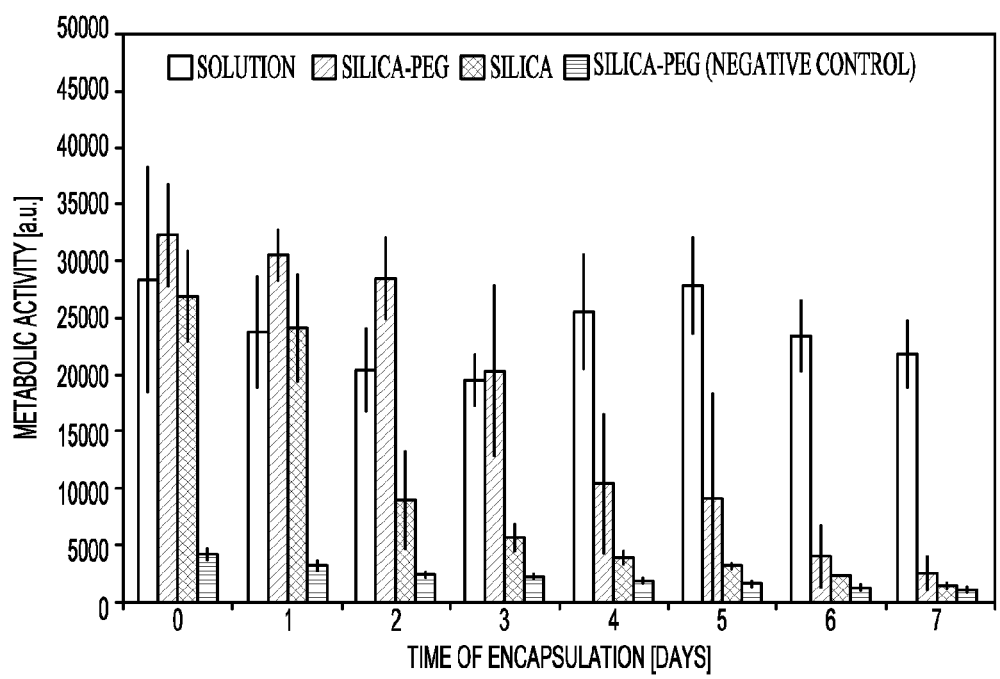
Figure 21A:
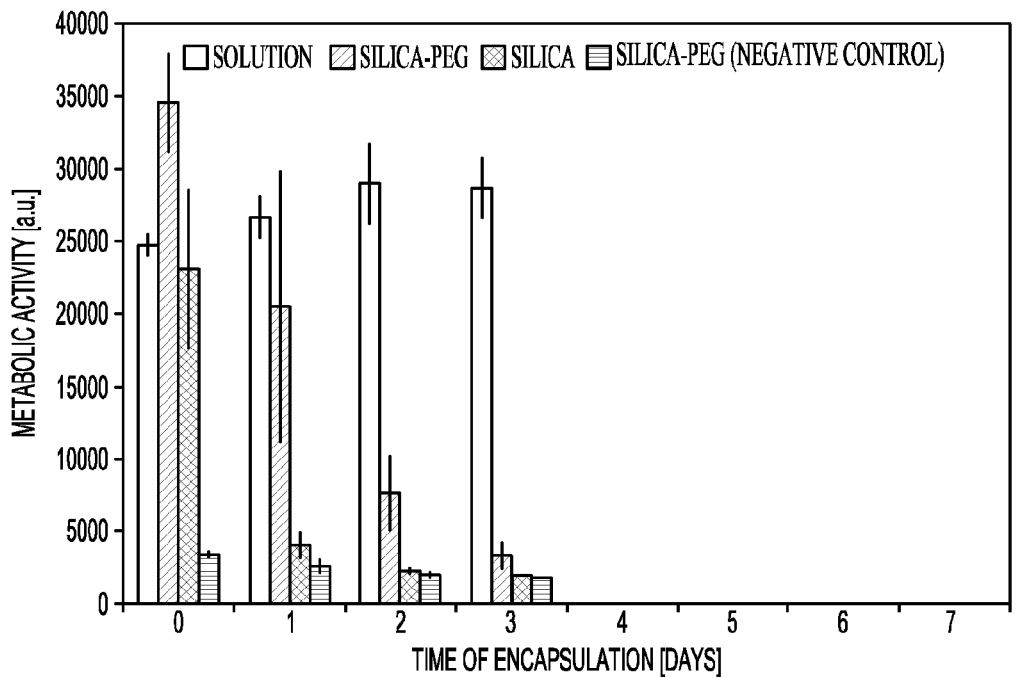
FIGS. 21 (A), (B), and (C) illustrate metabolic activity versus time for normal cell lines encapsulated in gels, in accordance with various embodiments.
Figure 21B:
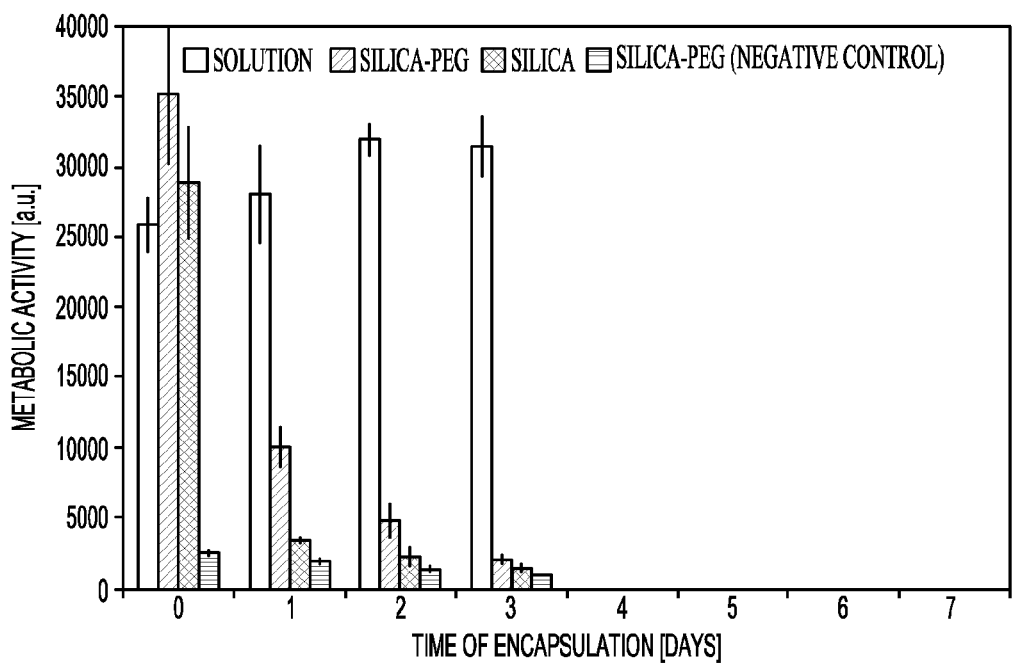
Figure 21C:
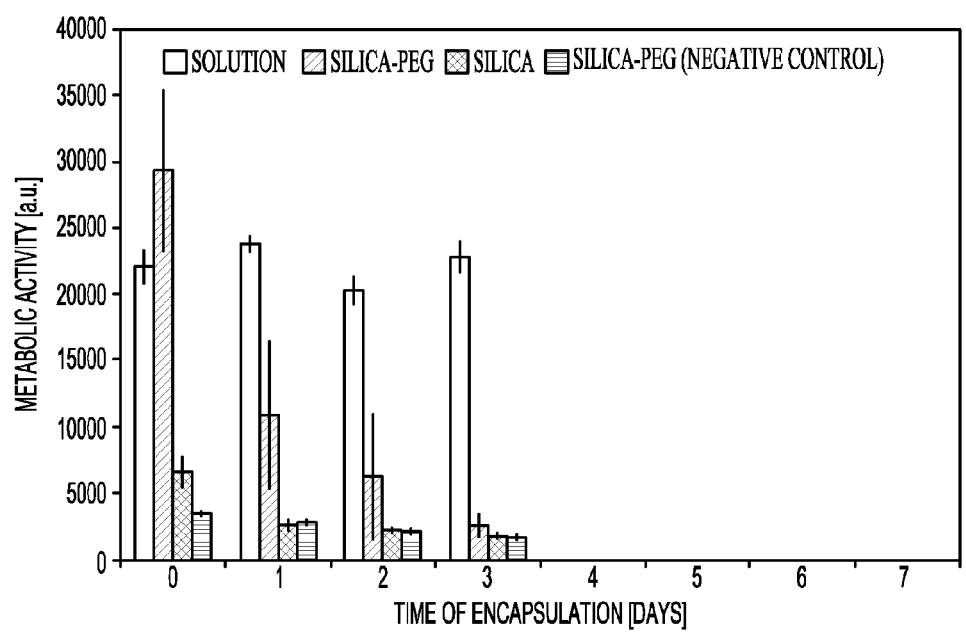

FIG. 20(A)-(C) shows the MA of different encapsulated cancer cell lines. For encapsulated LNCaP cells, there was not a significant change in MA over a week. Encapsulated MCF-7 showed a drop of 12% in MA with respect to first day of encapsulation. On the other hand, encapsulated OVCAR-5 maintained their MA for over 3 days, experiencing a significant drop at the 4 day. Normal cell lines (HFFs, HUVEC, and MEFs) remained metabolically active for no more than 3 days (FIG. 21(A)-(C)). To the best of our knowledge, the differences in MA of encapsulated cancer versus normal cell lines have not been reported.

Figure 22A:
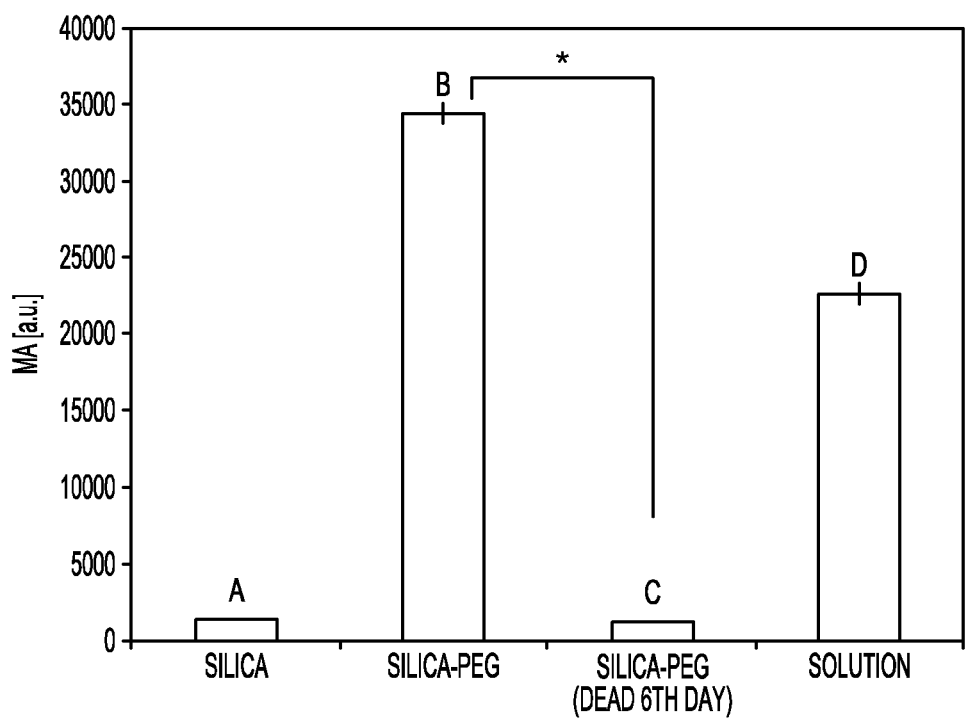
FIGS. 22 (A) and (B) illustrate MA of encapsulated LNCaP cells after six days of encapsulation, in accordance with various embodiments.
Figure 22B:
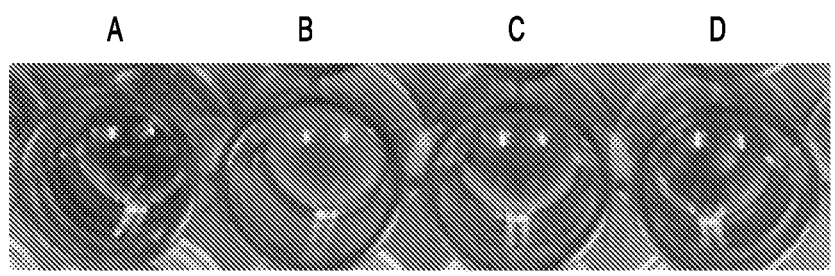
Figure 24A:
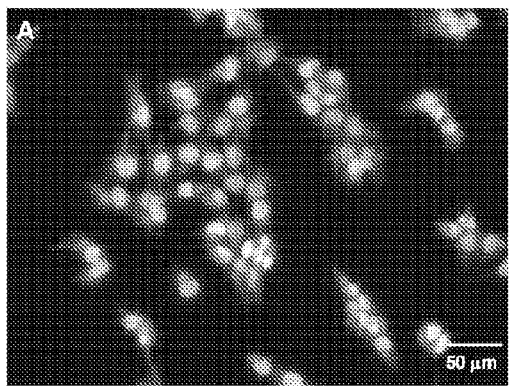
FIGS. 24 (A), (B), (C), and (D) illustrate recovered LNCaP cells after encapsulation a HFF:LNCaP mixed cell population, in accordance with various embodiments.
Figure 24B:
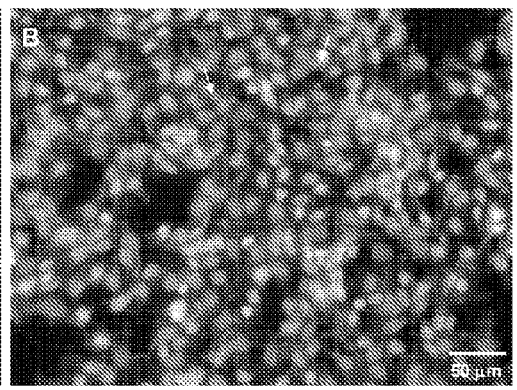
Figure 24C:
Figure 24D:
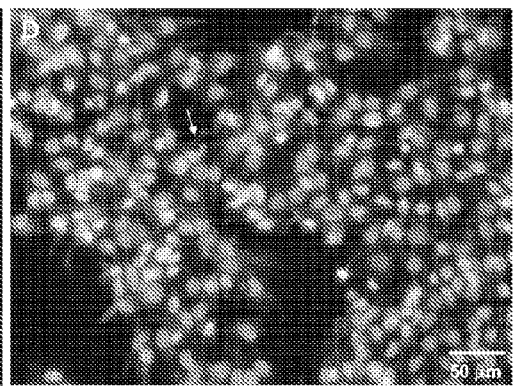

Further controls were also imposed on the experiments. For example, cells were killed after six days of encapsulation using a 70% ethanol solution and their MA was compared to live encapsulated cells, and the results indicated a significant difference in MA measured in the live encapsulated and dead encapsulated cells proving the measurement/experimental technique ($p<0.05$) as shown in FIGS. 22 (A) and (B).

2.3.4) Development of a Cancer Cell Isolation Platform

Viable cancer cells from tumors can be used for functional and cytotoxicity studies with new cancer drugs. Moreover pure population of cancer cells can be used for genomic, proteomic, and metabolomics studies. New cell lines can be established from isolated cancer cells. This is a high priority especially for the types of cancers for which only a handful of cell lines are currently available (e.g., prostate cancer). Therefore, the possibility of encapsulating a combination of cancer cells and normal cells in order to determine the potential of using SPEG gels as a screening tool for cancer cells in tumors was explored FIG. 20 illustrates cancer cell lines encapsulated in SPEG-4-arm ($M_w$=2 kDa) gels, (A) LNCaP, (B) MCF-7, (C) OVCAR-5. Solution indicates cells incubated in culture media, and the negative control is encapsulated dead cells. These cells were exposed to 70% ethanol prior to encapsulation (n=3).

FIG. 21 illustrates normal cell lines encapsulated in SPEG-4-arm ($M_w$=2 kDa) gel, (A) HFF, (B) HUVEC, (C) MEF. Solution indicates cells in culture media, and the negative control is encapsulated dead cells. These cells were exposed to 70% ethanol prior to encapsulation (n=3).

FIGS. 22 (A) and (B) illustrate MA of encapsulated LNCaP cells after six days of encapsulation. The test well was prepared with the addition of 40 μl of ethanol and incubated for 12 h prior to the addition of alamar blue (n=3).

Table 2.3 Encapsulation of mixed cell populations. (i) Extraction from SPEG gel, (p) extraction from reversible gels. Time refers to extraction time after encapsulation.

| Cell mixed population | Encapsulated cell densities in millions [cells/ml] | Gel type | Time [h] |
|---|---|---|---|
| HFF (F) and OVCAR-5 (O) | 18.3 (F):15.23 (O) 2.3 (F):2.4 (O) | SPEG (i), (p) | 24, 48 |
| HFF (F) and LNCaP (L) | 22.8 (F):45.8 (L) 4.4 (F):4.8 (L) | SPEG (i), (p) | 24, 48 |

Different cell densities of cancer and normal cells were mixed at 1/1 (v/v) ratio (Table 2.3). The mixed cell population was then encapsulated in the SPEG-4-arm gels described in Section 1. Cells were extracted from the gels 24 and 48 h after encapsulation. The extracted cells were incubated in 6-well plates at 37° C. and 5% $CO_2$ for different periods of time to measure proliferation activity. In order to verify that the gels could be used to select for the cancer cells, a specific cancer cell antibody (EPCAM/TROP1 antibody) than binds the epithelial cell adhesion molecule (EpCAM or CD326) present in the surface of the cells was used. EpCAM is a transmembrane glycoprotein that is identified as a marker for carcinoma, attributed to its high expression on rapidly proliferating tumors of epithelial origin. Normal epithelia express EpCAM at a variable but generally lower level than carcinomas. Cells recovered from the gels were stained with EPCAM/TROP1 antibody as a primary antibody. For detecting, a secondary antibody (Immunoglobulin G, IgG) conjugated with a fluorescence reporter was used for fluorescence microscopy visualization.

The standard immunohistochemistry protocol was as follows:

1) First, cells were seeded or incubated on a cover slip or 6-well plate until the desired cell density was obtained.
2) All the media was removed from the culture cells and wash twice with PBS.
3) 300-400 μl of 2-4% of formaldehyde fixative solution was added to each well, followed by incubation for 20 min.
4) The cells were washed twice with PBS and cover with 400 μl of wash buffer. The samples were stored at 2-8° C. for up to 3 months or stained immediately. Wash buffer was prepared with 0.1% BSA in 1×PBS.
5) The cells were washed twice with 400 μl of wash buffer.
6) Non-specific staining was blocked by adding 400 μl of blocking buffer followed by incubating for 45 min at room temperature.
7) Blocking buffer was removed.
8) The primary antibody (EpCAM/TROP1) was diluted in 1×PBS at a concentration of 25 μg/ml.
9) 1 ml of the diluted antibody was added to the cells followed by incubation at room temperature for 1 h. In some examples, the cells were incubated overnight at 2-8° C.
10) 400 μl of wash buffer was used to wash two times.
11) The secondary antibody was diluted in 1×PBS at a volume ratio of 1/200.
12) 400 μl of the secondary antibody was added to the cells followed by incubation for 1 h at room temperature in the dark.
13) 400 μl of wash buffer was used to rinse two times.
14) 300 μl of diluted DAPI solution was added to each sample, followed by incubation for 2-5 min at room temperature. In some examples, DAPI is a nuclear dye that can stain the cells.
15) PBS was used to wash once and water was used to wash once.
16) Using a fluorescence microscope, visualization was performed with the appropriate filters. Fluorescence filters for DAPI dye, and fluorescence filters for FTIC dye were used.

From HFF:OVCAR-5 and HFF:LNCaP mixed cell populations, only OVCAR-5 and LNCaP cells were recovered after encapsulation since the incubated cells stained positive for EpCAM as indicated in FIG. 23 and FIG. 24. However, very few fibroblasts were observed in some mixed populations extracted at 24 h, which was in agreement with the results of HFF encapsulation in SPEG-4-arm gels. FIGS.

23(A), (C) and FIGS. 23(B), (D) show OVCAR-5 cells stained after 26 and 22 days after extraction, respectively. Moreover, FIGS. 24(A), (C) and FIGS. 24 (B), (D) show LNCaP cells stained after 7 and 6 days after extraction, respectively. It was observed that the rate of attachment and growth for the recovered cells was slower than the non-encapsulated OVCAR-5 or LNCaP cells. However the morphology of the cells was very similar under the optical microscope.

Even though the majority of the SPEG-gel particles were removed during the cell extraction process (e.g., filtering with a cell strainer), small particles remained within the cell surface as can be observed from the fluorescence micrographs as very bright red dots (yellow arrow in FIG. 23 and FIG. 24). It is possible that these particles might have interfered with the cell growth rate. The results show the selectivity of the SPEG or reversible gels for screening of cancer cells.

FIG. 23 illustrates recovered OVCAR-5 cells after encapsulation of HFF:OVCAR-5 mixed cell population. Fibroblasts were not detected after 48 h post extraction. (A) Cells extracted from SPEG-4-arm gel after 24 h of encapsulation, (B) cells extracted from SPEG-4-arm gel after 48 h of encapsulation, (C) cells extracted from reversible gel after 24 h of encapsulation, and (D) cells extracted from reversible gel after 48 h of encapsulation.

FIG. 24 illustrates recovered LNCaP cells after encapsulation a HFF:LNCaP mixed cell population. Fibroblasts were not detected at 48 h. (A) Cells extracted from SPEG-4-arm gel after 24 h of encapsulation, (B) cells extracted from SPEG-4-arm gel after 48 h of encapsulation, (C) cells extracted from SPEG-4-arm particulated gel after 24 h of encapsulation, and (D) cells extracted from SPEG-4-arm particulated gel after 48 h of encapsulation.

2.5) Conclusions

A facile methodology was described for the formation of thixotropic silica gels or hybrid gels. Since an organic polymer was used as an additive, the resultant gel was formed by the aggregation of micrometer size particles that interacted to each other by hydrogen bonding. This unique characteristic of the gel allowed the formation of "reversible" biomaterials. Encapsulation of cells for cell culture, and even a methodology for preservation of cells were described with the new materials developed.

In the second part of Section 2.0, the benefits of encapsulated cancer cells in the SPEG-4-arm gels for the development of a screening biomaterial from tumor cells was described. The selectivity of the biomaterial was demonstrated by the analysis of the recovered cells.

3.0. Development of Thixotropic Silica Gels for Reversible Encapsulation of Cancer Cells 3.11 Methods
3.1.1) Making of the THEOS "Irreversible" Silica Sol-Gel Matrices These gels are called "irreversible" since initially it seemed that cells could not be extracted from these gels. However, further research showed that these gels could also be reversed and the cells extracted. Thus, as used in this application, "reversible" and "irreversible" are merely labels and are not intended to mean that cells can or cannot be extracted from a particular gel.

A 1.5 mL microcentrifuge tube containing 1 mL of cell growth media was mixed with 20 µL of 85 nm colloidal silica particles that had been washed with ultra pure water three times. 4 µL of Tetrakis(2-hydroxyethyl) orthosilicate (THEOS) were aliquoted out into microcentrifuge tubes, one for each well of a 96 well plate being filled. The following steps were conducted in quick succession, to avoid polymerization of the gel before being transferred into a well. 20 µL of silica-media solution were added to an aliquot of THEOS and vortexed quickly. 20 µL of media were added. Then all 44 µL of solution were transferred into a well of a 96 well plate.

3.1.2) Making of the THEOS-PEG "Irreversible" Silica Sol-Gel Matrices

In this gel, PEG was introduced to the solution. A microcentrifuge tube containing 1 mL of cell growth media was mixed with 20 mL of 85 nm washed colloidal silica particles. 900 µL of this solution were taken out and placed in a new tube containing 100 µmL of 4-arm 2 kDa PEG. THEOS (4 µL) was aliquoted out into tubes, one for each well being filled. 20 µL of silica-media-PEG solution were added to an aliquot of THEOS and vortexed quickly. 20 µL of media were added. Then all 44 µL of solution were transferred into a well of a 96 well plate.

3.1.3) Making of the THEOS-PEG "Particulated" Silica Sol-Gel Matrices

Particulated silica sol-gel matrices are made in a similar fashion to the irreversible silica sol-gel matrices, but with a few major distinctions. These gels are made in bulk initially. 220 µL of silica-media solution was added to a 43.5 µL aliquot of THEOS. This was pipetted to mix. 220 µL of cell growth media was quickly added to the solution and vortexed thoroughly. The solution was left to sit for about 15 minutes to gel. Four microcentrifuge tubes of this gel were created. After sitting, 500 µL of cell growth media were added to the gel and pipetted to mix. The gel and media were transferred to a 50 mL capped tube. The microcentrifuge tube was rinsed with another 500 µL of cell growth media and added to the rest. All of the four tubes of gel were diluted in media and transferred to the same 50 mL capped tube. This 50 mL capped tube with gel was placed on the sonicator, and the gel was sonicated for 5 minutes at 30% power. This sonication was done in order to particulate the gel in a consistent manner. After sonication, the gel was transferred to a 15 mL capped tube, vortexed for about 10 seconds, and centrifuged at 1500 RPM for 5 minutes. The vortexing was used to ensure effective pelleting of the gel in the centrifuge. The supernatant was removed, and the gel was ready to use.

3.1.4) Making of the Particulated Silica Sol-Gel Matrix with 4.5% PEG

When PEG was added to the gel this was done in the initial gelation step. 220 µL of silica-media-PEG solution was used instead of the silica-media solution. This solution containing PEG was added to the 43.6 µL of THEOS aliquoted and pipetted to mix. 220 µL of cell growth media was also added and the solution was vortexed. The solution was then left to gel for about 15 minutes. The particulation method was identical to the gels described before.

3.1.5) Encapsulation of Cells in Irreversible Matrices

For irreversible encapsulation, cells were added to the gel prior to gelation. The gels were made with the following adjustment: instead of adding 20 µL of media to the gel solution prior to transferring into a 96 well plate, 20 µL of cells in media at a density of 500,000 cells/mL were added instead. All 44 µL of cells and gel solution were transferred together into the 96 well plate and left to solidify. Once the gel was formed (around 5 minutes) 50 µL of media were added to the top of the gel. This followed the encapsulation scheme seen in FIG. 1-A.

3.1.6) Encapsulation of Cells in Particulated Matrices

Encapsulation in particulated matrices was significantly different in comparison with the Irreversible matrices. Because cells were encapsulated in a matrix composed of particles loosely associated, the bottom of each well in a 96 well plate that would house the encapsulated cells was coated. The coating was consisted of an irreversible gel made in the manner previously seen but in a ratio that allowed for a total of 20 µL in each well. No cells were encapsulated in this irreversible gel coating. This was to insure that the cells did not settle out of the gel and attach to the bottom of the well. Gels for encapsulation were made according to the directions given before. Once the gels were centrifuged and the supernatant was removed, gel was aliquoted out into microcentrifuge tubes. In the tubes, 55 µL of gel were added and 40 µL of cells were gently pipetted in. Of this cells and gel mixture, 40 µL were transferred to each well of the 96 well plate that was coated previously. The well was capped with 50 µL of media. The encapsulation scheme followed FIG. 25-B. FIG. 25 illustrates two different schemes used for encapsulation. FIG. (A) illustrates the encapsulation scheme used with cells encapsulated in irreversible gels. FIG. (B) illustrates the encapsulation scheme used with cells encapsulated in particulated Irreversible gels.

3.1.7) Measurement of the Metabolic Activity of Encapsulated Cells

Cells were encapsulated in 96 well plate for the metabolic activity experiment. The samples chosen were particulated irreversible gels with 0% PEG and 4.5% PEG, irreversible gels with 0% PEG and 4.5% PEG, and un-encapsulated controls. The encapsulation methods were previously described. Both the particulated irreversible gels and the un-encapsulated controls had two columns with live cells and two columns for dead cells, respectively. The Irreversible gels just had two columns for live cells. Dead cells were prepared by soaking the cells in a 70% ethanol solution for at least 30 minutes. A Hoechst and propidium iodide stain were used to check that the dead cell control was in fact dead. All cells were encapsulated with a density of 500,000 cells/mL.

Alamar blue, a cell health indicator, was used on MCF 7 and MCF 10A cells encapsulated in a particulated irreversible and irreversible gels as well as un-encapsulated controls. Alamar Blue measures metabolic activity in cells and contains the Resazurin molecule. This is a non-fluorescent dye that can easily enter living cells without any toxic effects. Healthy cells naturally metabolize this molecule into resorufin, a fluorescent molecule. The amount of fluorescence is proportional to the amount of metabolic activity occurring, which represents the amount of viable cells in a sample. Alamar blue was added to the first well in each test group on the first day of encapsulation. Each subsequent day another well in each test group had Alamar blue added to it. The metabolic activity was measured using a Gemini Microplate Fluorimeter.

3.1.8) Extracting and Recovering Encapsulated Cells

Cells were encapsulation for the most part at a density of around 2.3 million cells/mL. Different samples with different techniques were used to determine the best method for analyzing cell recovery post encapsulation.

MCF 10A Sample 1: Cells were encapsulated in a Particulated Irreversible gel with 4.5% PEG. Around 100 µL of media were added to the top of each well and were pipetted up and down to mix. The solution was transferred into a culture dish and diluted with 10 mL of media. The cells remained seeded for 24 hours before they were rinsed with DPBS (2x) and trypsinized for 15 minutes. The solution was transferred to a 15 mL capped tube and centrifuged at 800 RPM for 5 minutes. The supernatant was removed and 20 µL of media were added to the tube. A cell count was taken.

MCF 10A Sample 2: Cells were encapsulated in a Particulated Irreversible gel with 4.5% PEG. While encapsulated, 100 µL of trypsin were added to each well and gently shaken for 10 minutes. The sample was then treated in a similar manner as MCF 10A Sample 1.

MCF 10A Sample 3: Cells were encapsulated in a Particulated Irreversible gel with 4.5% PEG. The cells were treated in a similar manner as MCF 10A Sample 2 until the cells were trypsinized for a second time after 24 hours of being seeded. The cells and trypsin were transferred to a 15 mL capped tube, and the culture dish was rinsed with 5 mL of DPBS and added to the 15 mL tube. This extra rinse step was designed to help collect cells that were left behind. The tube was centrifuged and a cell count was taken as usual.

MCF 10A Sample 4: Cells were encapsulated in a Particulated Irreversible gel with 4.5% PEG. While encapsulated, the cells were soaked in 100 µL of trypsin and were gently shaken for 10 minutes. Instead of pipetting up and down to break up the gel to release cells, the contents of the well were just picked up with a pipette with the tip cut off and transferred immediately to a culture dish. The remaining treatment was comparable to that of MCF 10A Sample 3.

MCF 10A Sample 5: Cells were encapsulated in a Particulated Irreversible gel with 0% PEG. The treatment was the same as seen with MCF 10A Sample 2.

MCF 10A Sample 6: Cells were encapsulated in a Particulated Irreversible gel with 0% PEG. These cells were processed in the same way as MCF 10A Sample 4.

MCF 7 Sample 1: Cells were encapsulated in a Particulated Irreversible gel with 4.5% PEG. Cells were treated in a manner similar to MCF 10A Sample 2.

MCF 7 Sample 2: Cells were encapsulated in a Particulated Irreversible gel with 0% PEG and were processed like MCF 10A Sample 2.

The number of cells recovered was normalized over the number of cells that were initially encapsulated. Also, MCF 10A Samples 4 and 6 were imaged with an inverted microscope prior to being trypsinized and counted.

Materials and methods for making of the main gel types are given here but these are not all of the gels used. The lists of other gels are given in Appendix A.

3.2. Results:

In preliminary experiments, encapsulation of tumor cells in high porosity silica gels was found to disrupt the normal interactions between the cells and their microenvironment, potentially generating conditions for transition into a dormant state. These gels are of high porosity, therefore enabling circulation of nutrients but they can be made mechanically stiff enough to completely inhibit cell proliferation. Furthermore, the gels developed are mechanically reversible (thixotropic), enabling on-demand extraction of the cells from the gel.

TABLE 3

Summary of Preliminary Experiments: In-gel metabolic activity of encapsulated cells.

| Cell Line | Disease/Description | Time to 50% MA* | Time to 0% MA* |
|---|---|---|---|
| Human Foreskin Fibroblasts (HFF) | Normal Fibroblasts | 1.5 days | 3.5 days |
| Mouse Embryonic Fibroblasts (MEF) | Normal Fibroblasts | 1.0 day | 3.0 days |
| Human Umbilical Vascular Endothelial Cells (HUVEC) | Normal Endothelial Cells | 1.0 day | 3.0 days |
| Human Mammary Gland Epithelial Cell (MCF-10A) | Non-tumorigenic Epithelial Cells | 1.5 days | 3.0 days |
| Human Ovarian Epithelial Cells (OVCar-5) | Adenocarcinoma | 4 days | 7 days |
| Human Prostate Epithelial Cells (LNCaP) | Carcinoma | >7 days | >21 days |
| Human Mammary Gland Epithelial Cell (MCF-7) | Adenocarcinoma | >7 days | >21 days |
| Human Mammary Gland Epithelial Cell (MCF10DCIS.COM) | Pre-malignant Ductal Carcinoma | >7 days | >21 days |
| Human Mammary Gland Epithelial Cell (MPA MB-468)* | Very Invasive Adenocarcinoma | <1 day | 1 day |

*Time it takes for the in-gel metabolic activity (MA) of the encapsulated cells to drop down to 50% of its initial (day 0) value
*Time it takes for the in-gel metabolic activity (MA) of the encapsulated cells to drop down to zero
*MDA-MB-468 is a very aggressive cancer cell line that is known to not transition to dormancy It has been shown for the first time that the cancer cell lines: LNCaP (human prostate adenocarcinoma), MCF-7 & MCF10DCIS.COM (breast adenocarcinoma), OVCAR, (ovarian adenocarcinoma) cells stayed metabolically active when encapsulated in silica-PEG gels at levels higher than that observed in solution for up to 3 weeks (Table 3). In contrast, normal cell lines; HFF (human foreskin fibroblasts), HUVECs (Human umbilical vein endothelial cells), as well as primary cells such as MEF (mouse embryonic fibroblasts) lost metabolic activity completely and perished within 1-3 days when encapsulated in the same irreversible gels. Non-tumorigenic epithelial cells (MCF-10A), which are known not to induce tumors completely perished within 3 days. MCF10DCIS.COM cells, which are a model for pre-invasive cancer and do not metastasize very rapidly survived encapsulation in excess of three weeks. On the other hand, MDA-MB-468 cells, which are very aggressive and known to not transition to dormancy died as quickly as the normal cells (Table 3). All of these results were obtained with the THEOS-Silica-PEG gels (initially called "irreversible gels" since it was believed that they could not be reversed; however, further research showed that these gels can be liquefied and the contents extracted). The metabolic activities of the encapsulated cells were measured with Alamar Blue assay, as shown in FIGS. 37(A)-(H), and summarized in Table 3.

Experiments have been conducted to test whether live cells can be extracted from these gels. Measuring the in-gel metabolic activity shows that the cells are metabolically active when they are encapsulated however, it does not necessarily imply that the cells can be successfully extracted from the gels. Extraction may impose harsh mechanical stresses on already stressed gels and may cause them to lose viability. FIG. 26 illustrates the viability of the encapsulated cells immediately after extraction from 4.5% PEG containing THEOS gels.

The viability of the cells was measured using Invitrogen LIVE/DEAD viability kit with the viable cells fluoresce green and the dead cells fluoresce red. The x-axis shows the amount of time the cells stayed encapsulated. The results show that the viability of the cells decrease with the time they spend encapsulated. This contradicts the results from the in-gel metabolic activity results, which showed no change in metabolic activity during that time. This may be interpreted as an increased sensitivity of the encapsulated cells to the current extraction processes applied.

Figure 27:
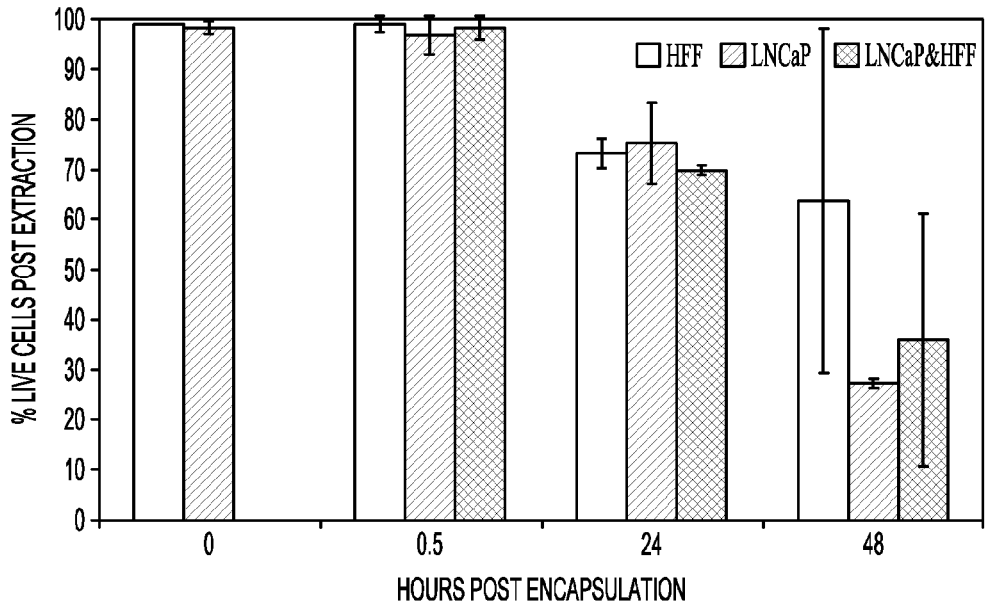
FIG. 27 illustrates the post-extraction viability of encapsulated cells, in accordance with various embodiments.

Some cells were encapsulated in 4.5% THEOS-PEG gels following a different protocol. After the gels were made, they were particulated manually and the allowed to form a gel around the cells. The rationale was that if the gels were broken up ahead of time, it would be easier to extract the cells afterwards. This resulted in a slightly better post-extraction viability as shown in FIG. 27 below. FIG. 27 illustrates post-extraction viability of the encapsulated cells from the 4.5% THEOS-PEG "irreversible gels" modified by particulation before encapsulation.

Figure 28:
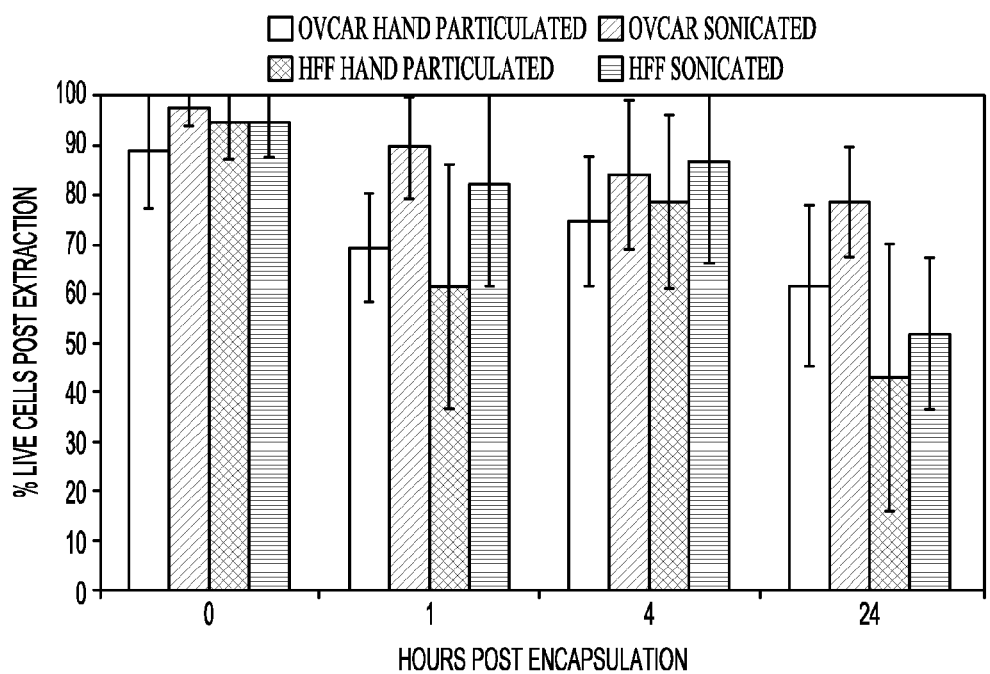
FIG. 28 illustrates the post-extraction viability of encapsulated cells, in accordance with various embodiments.

Similar experiments were also conducted with TEOS-PEG (1:9 THEOS to PEG ratio) thioxotropic reversible gels, with similar findings. FIG. 28 illustrates post-extraction viability of the encapsulated cells from the 1:9 TEOS:PEG ratio "reversible gels." FIG. 28 shows the post-extraction viability of HFF and OVCAR cell lines from gels made with two different particulation methods (hand particulation with grinding in a mortar and pestle vs. sonication). The cell viability post-extraction decreased with encapsulation time. There was not much of a difference between the TEOS-PEG (FIG. 28) and THEOS-PEG (FIG. 26) gels in terms of post-extraction viabilities since after 24 hours of encapsulation 40-80% of the cells could be extracted viable.

Figure 29:
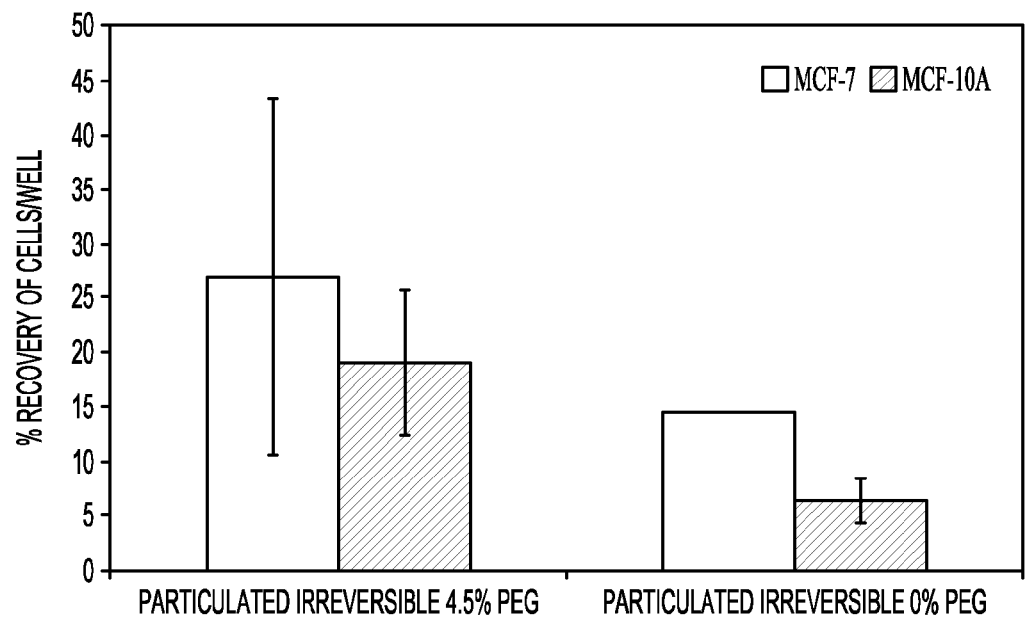
FIG. 29 illustrates the efficiency of recovery from irreversible gels, in accordance with various embodiments.

Even though the viability of the cells post-extraction was determined there were still questions about whether all of the cells initially encapsulated in the gels could be recovered or whether some of the cells were damaged/lost during the extraction process. Initial experiments conducted with MCF-7 and MSF-10A cell lines in particulated irreversible gels containing 0% or 4.5% PEG showed that only 5-30% of the encapsulated cells could be recovered from the gels (FIG. 29). FIG. 29 illustrates the efficiency of recovery from "irreversible" gels (% of the initially encapsulated cells that could be recovered from the gel), for MCF-7 and MCF-10A cell lines.

Figure 30:
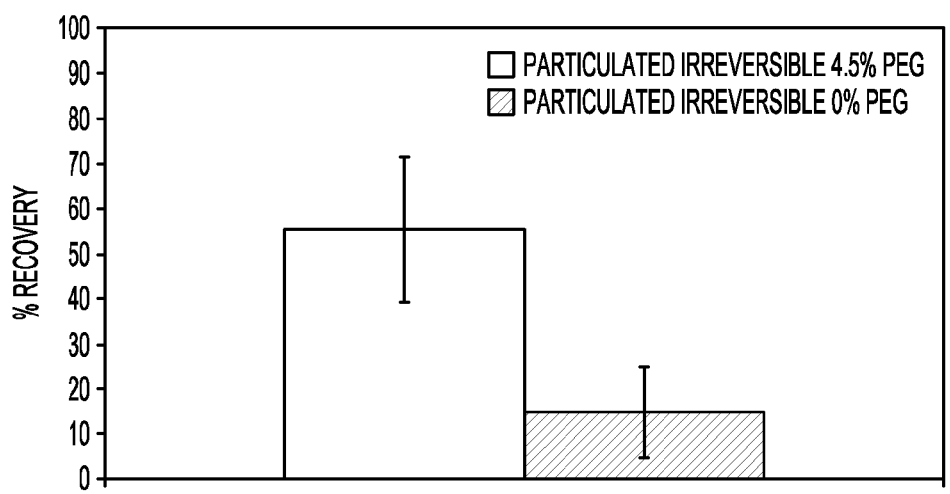
FIG. 30 illustrates the efficiency of recovery from irreversible gels, in accordance with various embodiments.

Using HFFs in encapsulated "irreversible" gels, recovery values in the 40-75% range were achieved with an average recovery of 55% (FIG. 30). FIG. 30 illustrates the efficiency of recovery from "irreversible" gels (% of the initially encapsulated cells that could be recovered from the gel), using HFF cells. By switching to "reversible" thioxotropic gels, recovery efficiency could be increased significantly.

Figure 31:
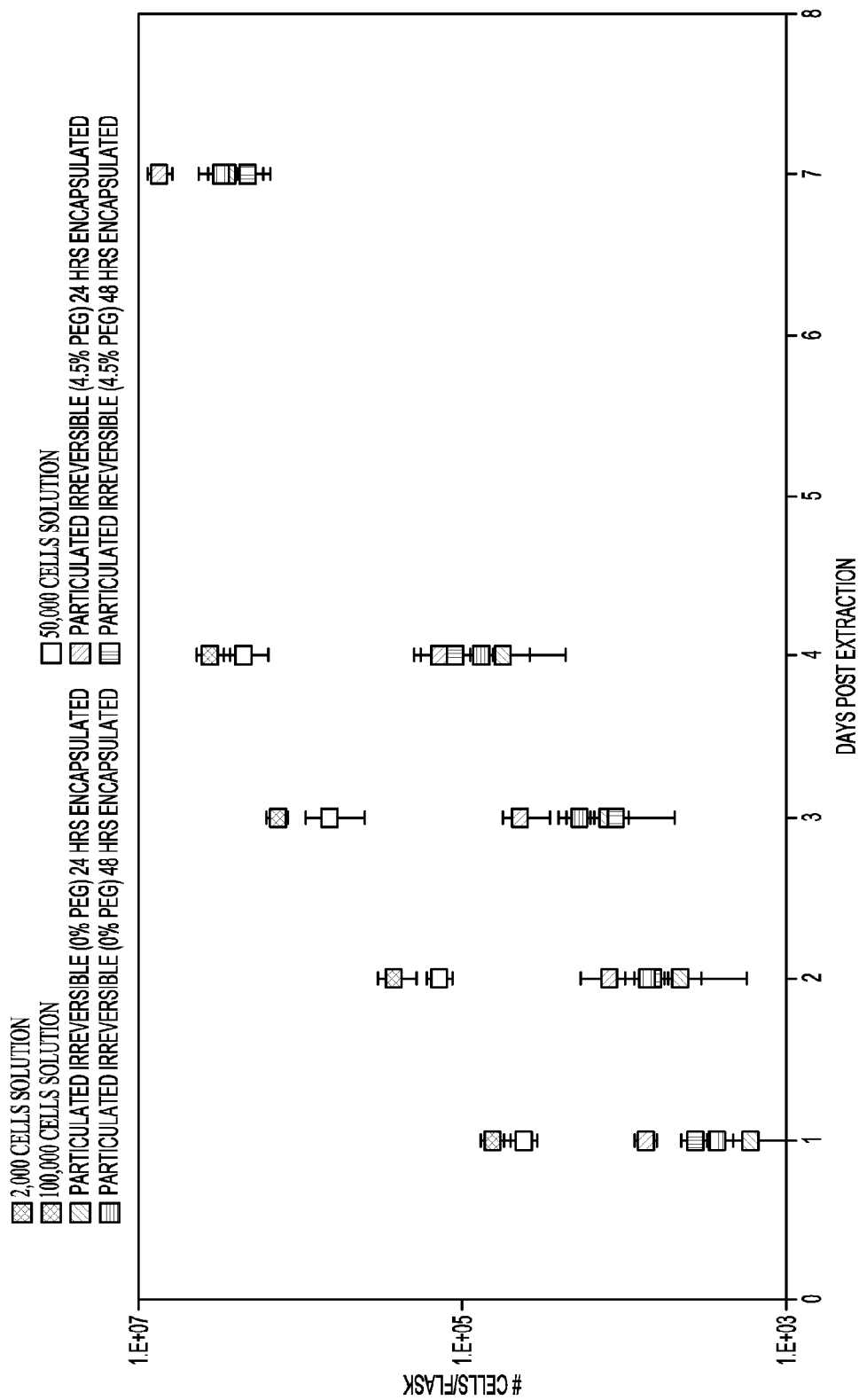
FIG. 31 illustrates the post-extraction proliferation of encapsulated MCF10A cells, in accordance with various embodiments.
Figure 32A:
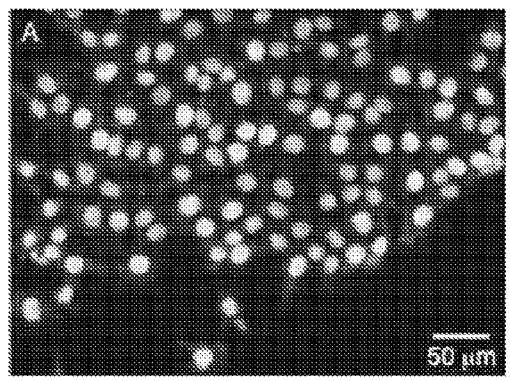
FIGS. 32(A), (B), (C), and (D) illustrate OVCAR cells growing in culture after encapsulation and recovery, in accordance with various embodiments.
Figure 32B:
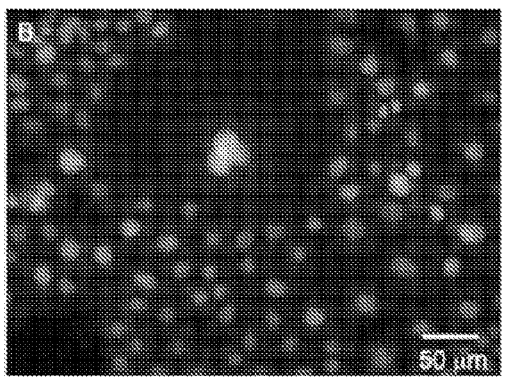
Figure 32C:
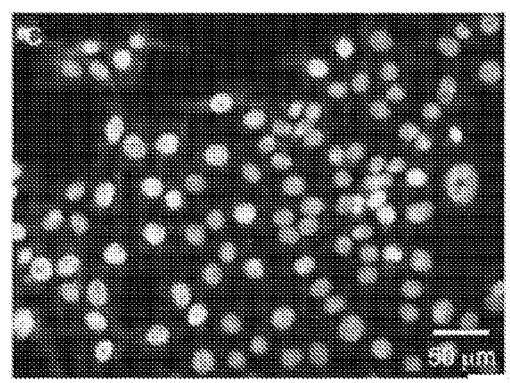
Figure 32D:
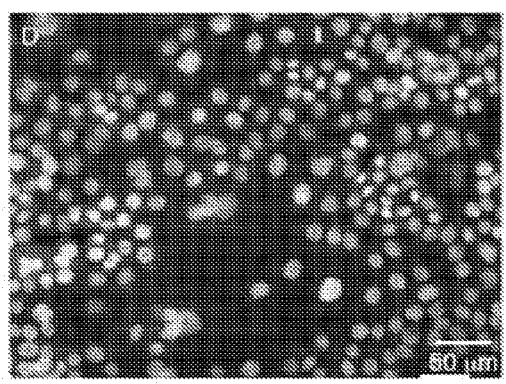
Figure 33A:
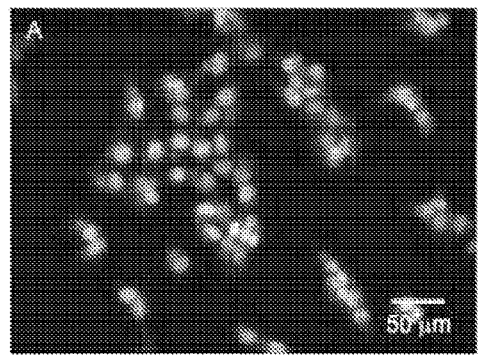
FIGS. 33(A), (B), (C), and (D) illustrate LNCaP cells growing in culture after encapsulation and recovery, in accordance with various embodiments.
Figure 33B:
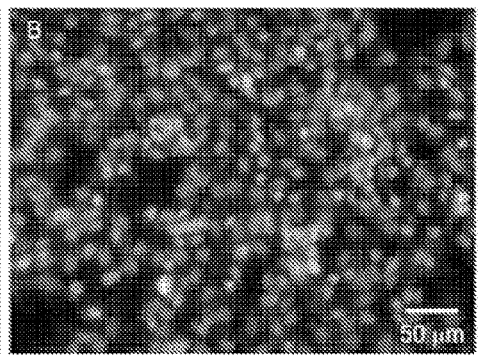
Figure 33C:
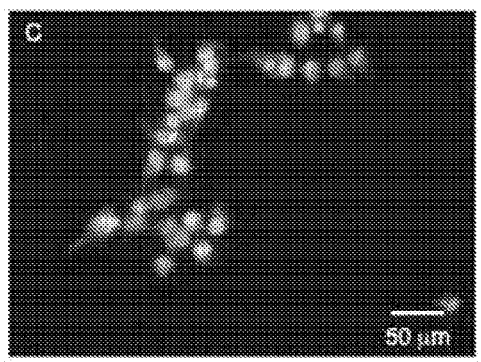
Figure 33D:
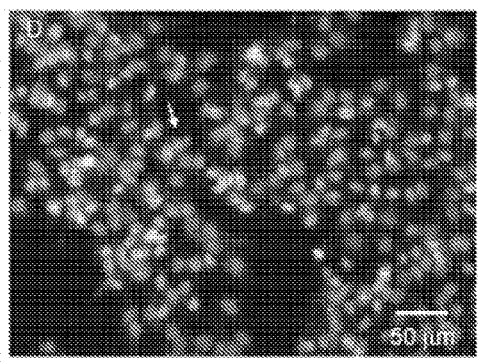

Another parameter that was explored was whether the viable cells extracted from the gels could attach on tissue culture flasks and proliferate and grow normally. The experiments conducted with selected cells showed that the cells recovered from the gels can actually continue to grow normally (FIG. 31), at the same rate as the un-encapsulated free cells (control). FIG. 31 illustrates the post-extraction proliferation of encapsulated MCF10A cells.

The fluorescent images in FIGS. 32 and 33 show that the cell extracted from the gels can attach to the tissue culture flasks and continue to grow normally as shown by the proliferation assay results in FIG. 31. The experiments conducted in FIGS. 32 and 33 were conducted with mixed populations of normal and cancer cells. In FIGS. 32 (A)-(D), OVCARs and HFFs were co-encapsulated and extracted after 24 hours. FIG. 8 illustrates OVCAR cells growing in culture after encapsulation and recovery. The cells were stained with EPCAM/TROP-1 antibody (primary), and anti-Mouse IgG secondary antibody. In FIG. 33, LNCaPs and HFFs were co-encapsulated and extracted after 24 hours. FIGS. 33(A)-(D) illustrate LNCaP cells growing in culture after encapsulation and Recovery. The cells were stained with EPCAM/TROP-1 antibody (primary), and anti-Mouse IgG secondary antibody. The samples were then stained with anti-EPCAM to determine the populations that express EPCAM, that is specific to the cancer cells. The results (as seen) showed that all the cells that were recovered expressed EPCAM, which initially led to the conclusion that all of the cells recovered were the cancer cells while all of the HFFs died. However, it was observed that HFFs occasionally stained with anti-EPCAM as well, complicating the interpretation of the results. Detailed examination of these images show that the cells that are in the field of view are morphologically resemble cancer cell lines, not HFFs.

Figure 34A:
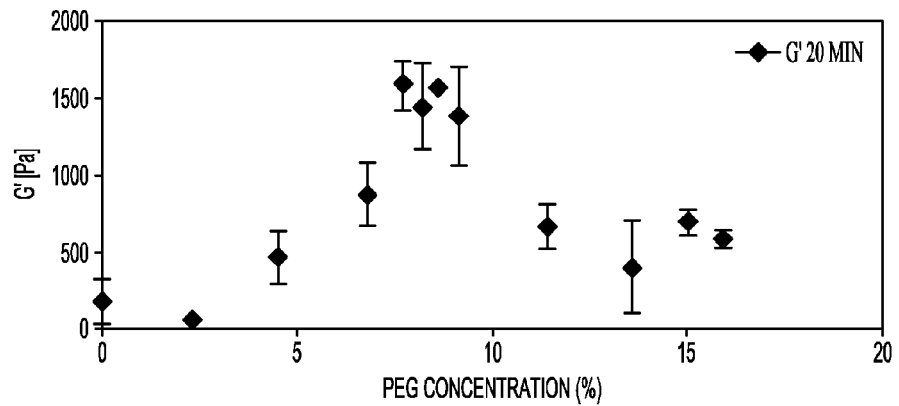
FIG. 34(A) illustrates the storage moduli of gels with varying PEG concentration, in accordance with various embodiments.
Figure 34B:
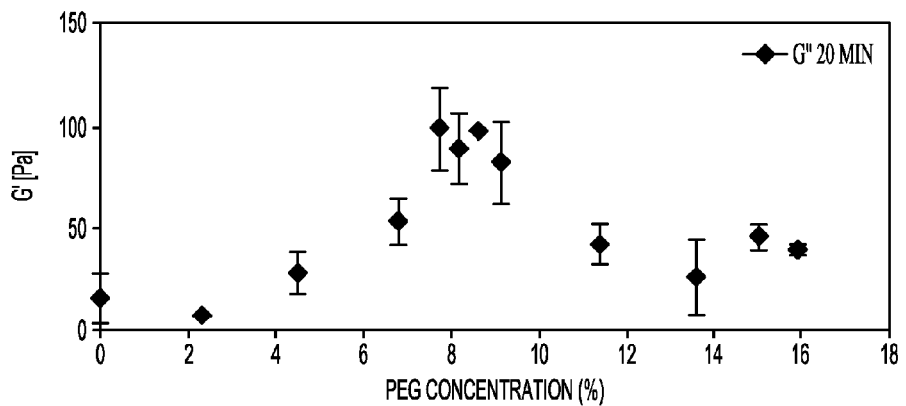
FIG. 34(B) illustrates the loss moduli of gels with varying PEG concentration, in accordance with various embodiments.

Normal and cancer cells are differentially affected by the mechanical stiffness of the extracellular matrix around them. Therefore, by changing the mechanical properties of the matrix, the survival response of the encapsulated cells can be altered. Mechanical properties of the gels were altered by altering the PEG concentration and rheometry was conducted to measure the loss and storage moduli of the THEOS-PEG "irreversible" gels used in metabolic activity measurement experiments. FIGS. 34A and B below show that the mechanical properties of the gels can be significantly changed by altering the PEG concentration. FIG. 34 illustrates A) storage moduli and B) loss moduli of the gels with varying PEG concentration measured 20 minutes after the onset of gelation. The mechanical properties increase with increasing PEG concentration up to 8.5% PEG concentration, where they reach a maximum. After this concentration, a decrease is observed.

Figures 35A, 35B, 35C:
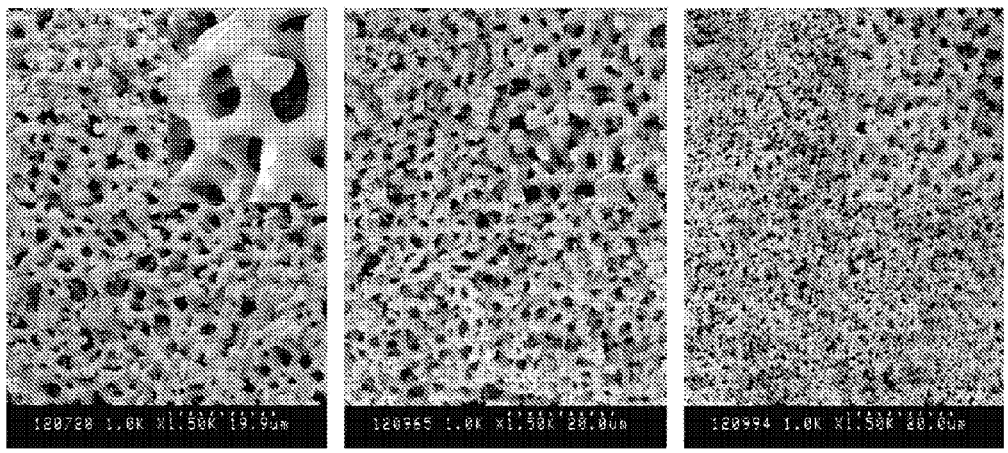
FIGS. 35(A), (B), and (C) illustrate the PEG concentration of the gels decreasing from the left image (A), to the center image (B), to the right image (C), in accordance with various embodiments.
Figure 36:
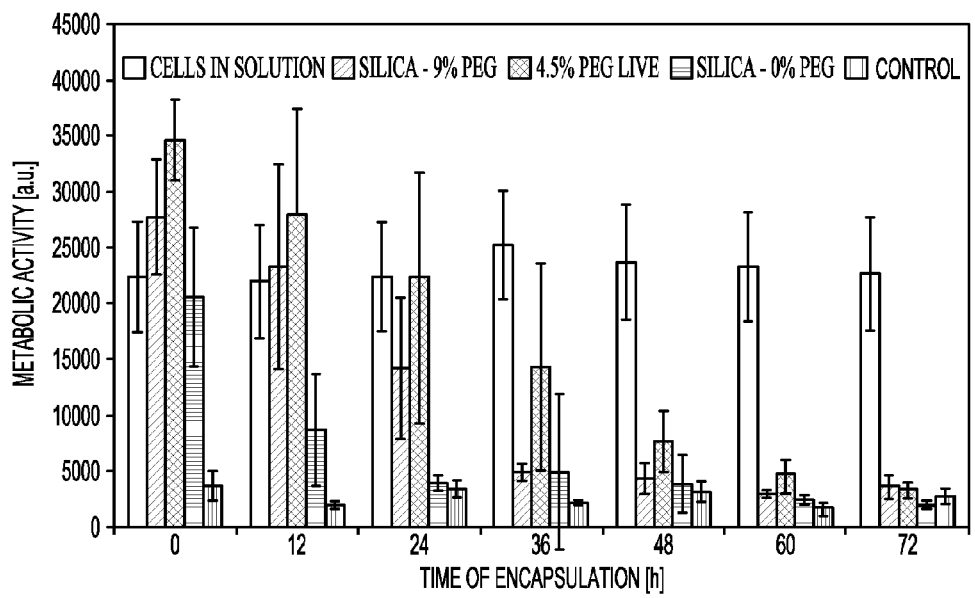
FIG. 36 illustrates the change in metabolic activity of encapsulated cells with changing gel mechanical properties, in accordance with various embodiments.
Figure 37A:
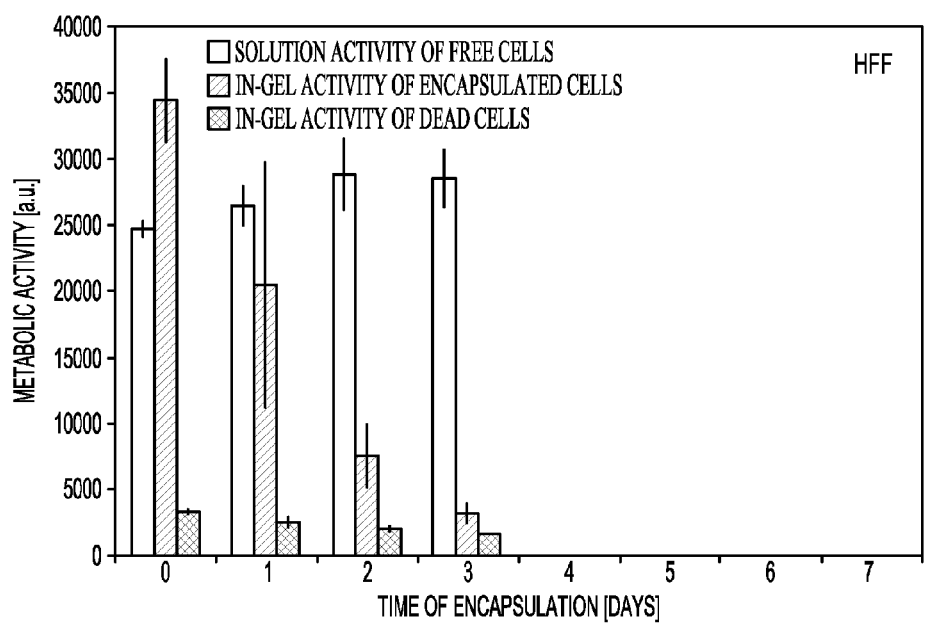
FIG. 37(A) illustrates in-gel metabolic activity of encapsulated HFF cells, in accordance with various embodiments.
Figure 37C:
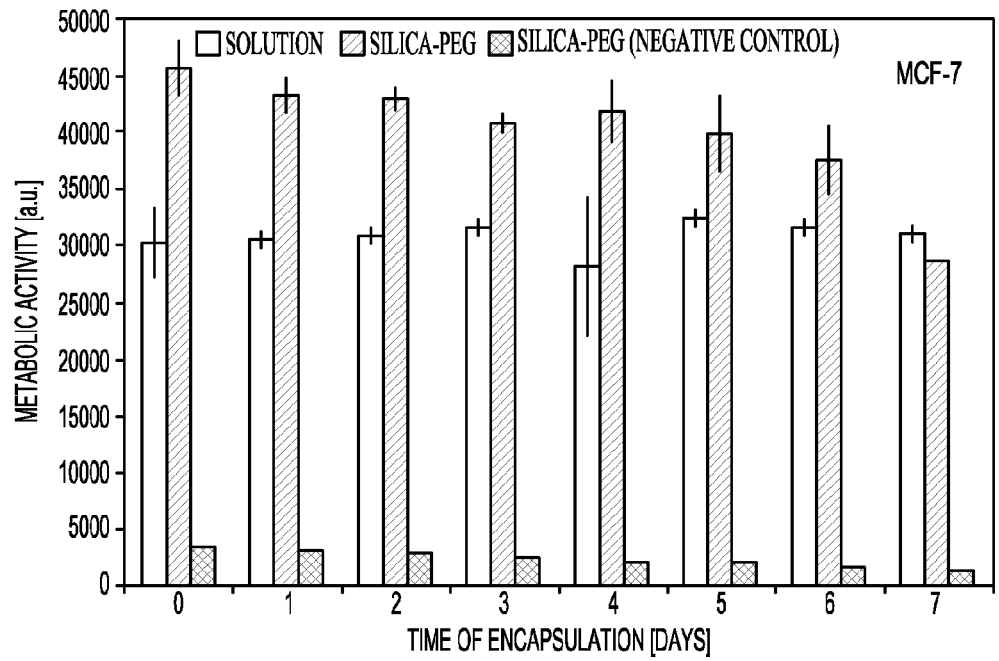
FIG. 37(C) illustrates in-gel metabolic activity of encapsulated MCF-7 cells, in accordance with various embodiments.
Figure 37D:
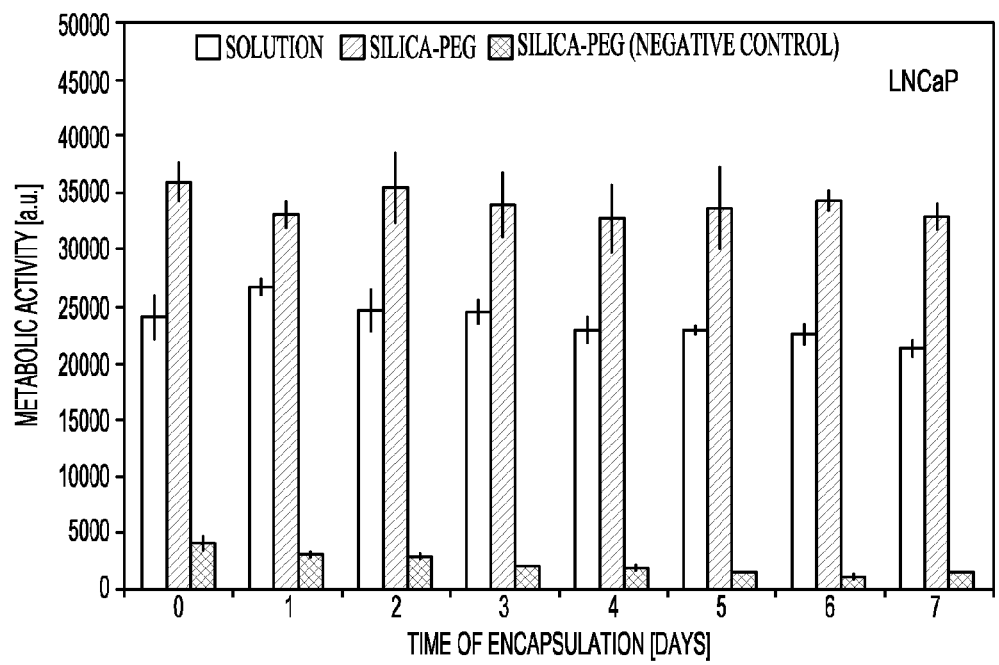
FIG. 37(D) illustrates in-gel metabolic activity of encapsulated LNCaP cells, in accordance with various embodiments.
Figure 37E:
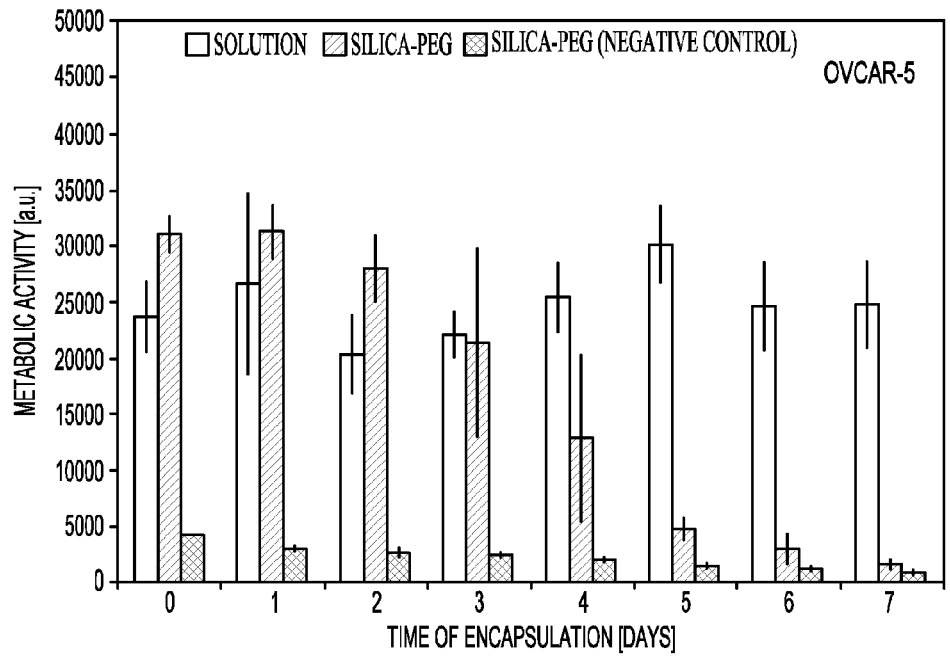
FIG. 37(E) illustrates in-gel metabolic activity of encapsulated OVCAR-5 cells, in accordance with various embodiments.
Figure 37F:
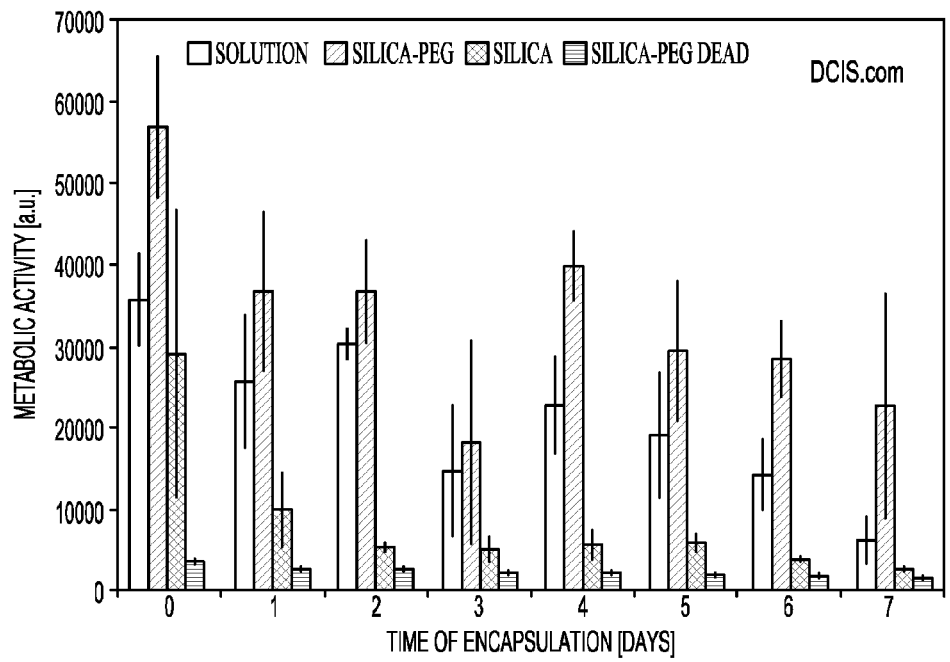
FIG. 37(F) illustrates in-gel metabolic activity of encapsulated DCIF cells, in accordance with various embodiments.
Figure 37G:
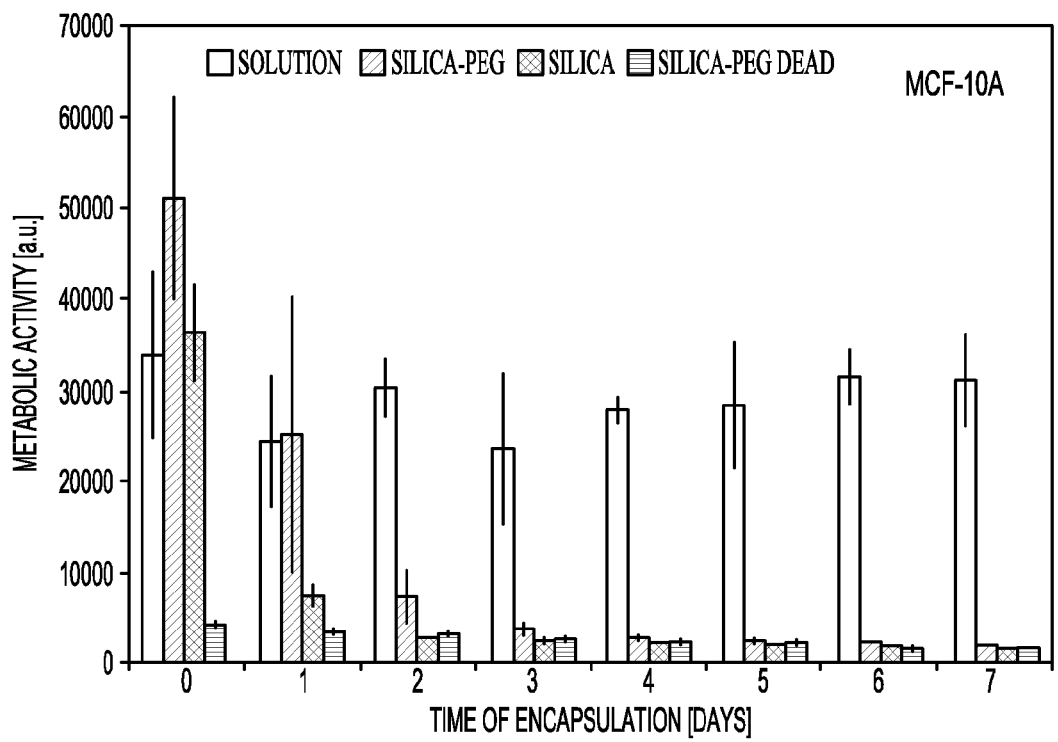
FIG. 37(G) illustrates in-gel metabolic activity of encapsulated MCF-10A cells, in accordance with various embodiments.
Figure 37H:
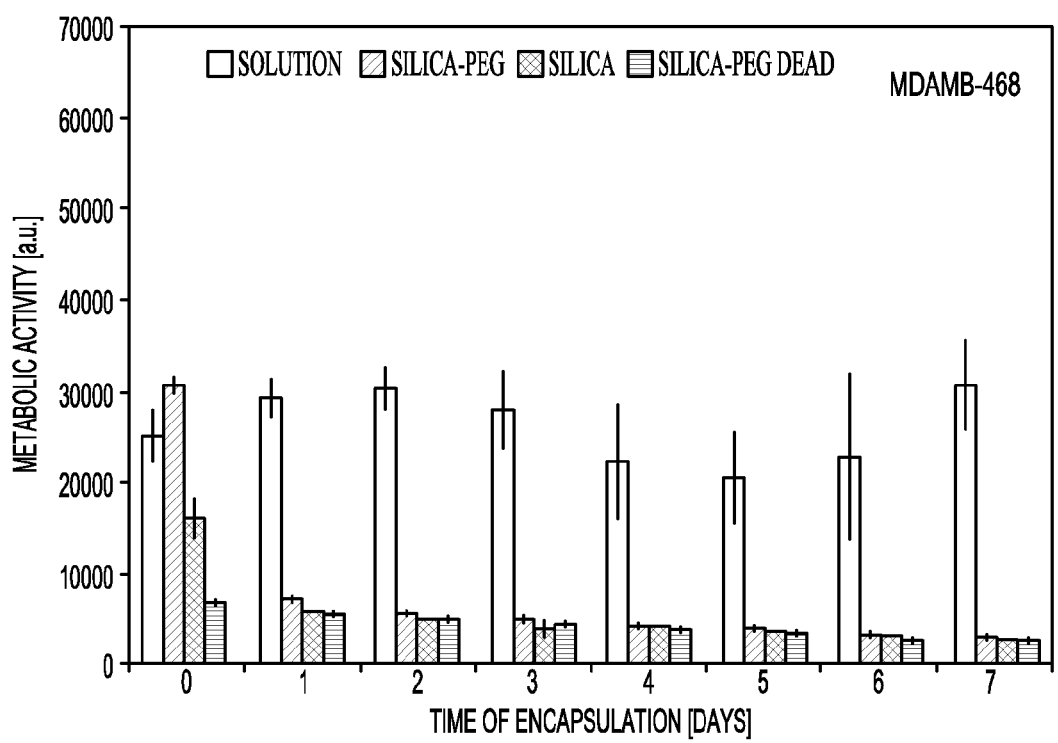
FIG. 37(H) illustrates in-gel metabolic activity of encapsulated MDAMB-468 cells, in accordance with various embodiments.

These results showed that the mechanical properties of the PEG gels can be modified by changing the PEG concentration. Altering the PEG concentration is known to change the ultrastructure of the gels and this is expected to alter the mechanical properties. For example, as shown by the SEM images, increasing PEG concentration decreases the porosity of the gels (FIG. 35). FIG. 35 illustrates PEG concentration in the silica gels decreasing from the left image (A) to the middle image (B) to the right image (C) resulting in a decrease in the permeability of the gel.

Preliminary experiments were conducted to determine the change in the metabolic activity of the encapsulated cells with the mechanical properties of the gels. Using HFFs, no dependence was detected of in-gel metabolic activity on the mechanical properties of the "irreversible" gels.

Summary: A variety of gels have been made to encapsulate mammalian cells and successfully recover the cells from these gels. The recovered cells can attach and normally grow in growth medium at the same rate as the un-encapsulated cells. There is a difference between the metabolic activities of cancer cells and normal cells when they are encapsulated. This was initially attributed to the ability of the cancer cells to transition into "dormancy," a state where they can stay for long periods of time without dividing. However, recent evidence in the literature showed that inhibition of attachment (which could be the case when cells are encapsulated in silica gels) could induce selective survival behavior. It is thus believed that the technology developed may not select cells based on their ability to transition to dormancy but their ability to survive while un-attached and thus metastasize. Independent of what the mechanism of selection could be, by optimizing the mechanical and structural properties of the gel, it can be possible to select for cancer cells in a heterogeneous population of cancer cells and normal cells, or a sub-population of cancer cells in a heterogeneous population of cancer cells based on their differential characteristics. This is potentially useful for selection of cancer cells that have metastatic properties and would be useful for drug screening and therapy planning in personalized medicine.

In various embodiments, the method allows isolation of cancer cells from a heterogeneous population of cancer cells and normal cells and may be used by pathologists to isolate and grow cancer cell lines for example, from tumor samples collected from patients (e.g., from fine needle aspirates, which contain a lot of red blood cells, white blood cells, and the host's own fibroblasts, endothelial cells, etc. in addition to the cancer cells). These cell lines can then be used to detect the phenotype of the cancer the patient has and help devise treatment strategies as well as developing/screening drugs for the specific kind of cancer the patient has. Advantageously, the cells can be encapsulated and kept for a long time. Also they can be extracted from the matrix at a desired time and the cells can continue to grow (to our knowledge this has never before been done with mammalian cells).

4.0. Additional Gels. Methods for Making Different Gels Used in Encapsulation of Mammalian Cells 4.1) PEG-Sodium Silicate Gels For this gel, 1.2 g of 20 kDa PEG were dissolved in 3.7 mL of 2M acetic acid and 3.7 ml of water. Once dissolved, for each gel made various amounts of a nanoparticle additive were added and mixed until uniform. A solution of 1.85 ml of 0.5 M Sodium Silicate and 5.15 ml water was added drop by drop to the PEG solution. The solution was left to stir for 30 minutes before the beaker was covered in parafilm and incubated at 37 degrees Celsius overnight. There were five gels that were made by this way. The first gel contained no nanoparticle additive. The second contained 400 mg of Cabosil, and the third contained 800 mg Cabosil. The fourth and fifth gels contained 800 mg of nanoclay, one hydrophilic bentonite, and the other montmorillonite.

The gels that contained the nanoclay additive did not form a gel. The nanoclay precipiatated out of the solution. The gel that did not have any additive formed a very weak gel. When Cabosil was added a stiffer gel formed. A quick inspection under the microscope showed that the particles formed were not uniform in either size nor shape. Rheological tests were performed on a PEG-Sodium Silicate gel with Cabosil as an additive, but clean data was not acquired.

4.1.1) 35 kDa Dextran-0.5M Sodium Silicate Gel

This gel was made very similarly to the PEG-SS gel previously. 1.2 g of 35-45 kDa Dextran were dissolved in 3.7 ml of 2M acetic acid and 3.7 ml of water. A nanoparticle additive was added once the Dextran was fully dissolved in the acetic acid. The nanoparticle was stirred until uniform. A solution of 1.85 ml of 0.5 M Sodium silicate and 5.15 ml of water was added drop by drop and then stirred for 30 minutes. The beaker was taken off ice, wrapped in parafilm, and incubated overnight. Two gels were made this way. The first gel contained 600 mg of Cabosil as the nanoparticle additive, and the other gel contained 400 mg of nanoclay.

The gels that had the nanoclay additive did not form. However, the gels that had the Cabosil additive formed a thixotropic gel. A brief examination under the microscope showed that the gel formed particles of nonuniform size and shape. Further experimentation was done on this gel.

4.1.2) 100 kDa Dextran-0.5M Sodium Silicate Gel

Another set Dextran-Sodium silicate gels were made. 1.2 g of 100 kDa Dextran were dissolved in 3.7 ml of 2 M acetic acid and 3.7 ml of water. Nanoparticles were added, stirred until uniform. A solution of 1.85 ml of 0.5 M Sodium Silicate and 5.14 ml of water was added drop-wise to the polymer solution. This was left to stir for 30 minutes before being taken off ice, wrapped in parafilm, and incubated at 37 degrees overnight. Two gels were made of this kind: one with 600 mg of Cabosil nanoparticles and the other with 400 mg of nanoclay nanoparticles.

Again, the gels that had the nanoclay additive did not form. It was concluded that a nanoclay additive would not form a useful product. It was rejected in favor of the Cabosil enhanced gel. However, the Cabosil enhanced gel still had nonuniform size and shape. Further experimentation was done on this gel.

4.1.3) 100 kDa Dextran-Sodium Silicate 500 Mg Cabosil Gel

The next gel that was made took 1.2 g of 100 kDa Dextran and dissolved it in 3.7 ml of 2 M acetic acid and 3.7 ml of water. 500 mg of Cabosil were added and mixed until uniform. A solution of 1.85 ml of Sodium Silicate and 5.15 ml of water were mixed together and added drop by drop to the polymer solution. The solution was mixed for 30 minutes, wrapped in parafilm, then incubated at 37 degrees Celsius overnight. Six gels were made with this protocol all with varying molarities of sodium silicate: 3.5 M, 3.0 M, 2.5 M, 2.0 M, 1.5 M, and 1.0 M. This gel varied the molarity of sodium silicate to see if a relationship between the rheology and the molarity could be seen. Clean rheology was not seen.

4.1.4) 35 kDa Dextran-Sodium Silicate 500 Mg Cabosil Gel 1.2 g of 35-45 kDa dextran were dissolved in 3.7 ml of 2 M acetic acid and 3.7 ml of water. 500 mg of Cabosil were added and mixed until uniform. A solution of 1.85 ml of Sodium Silicate and 5.15 ml water was added drop-wise to the polymer solution. The solution stirred for 30 minutes before being transferred to a 50 ml capped tube and incubated at 37 degrees Celsius overnight. Six gels of varying sodium silicate molarities were made using this protocol: 4.5 M, 3.5 M, 3.0 M, 2.5 M, 2.0 M, and 1.5 M.

This set of gels was also found to have nonuniform size and shape. Rheology was performed, giving clean results. There was full recovery to the solid gel state after the shear force was removed. It was found that gels made with a lower molarity of Sodium Silicate take longer to recover to a gel state than gels with a higher molarity.

4.2) Dextran Gels

Even though the dextran-sodium silicate gels were made to have the desired rheologic properties, they all had a significant amount of sodium leaching out into the surrounding medium. This sodium was proposed to affect the osmolarity of gel, and no easy way was found to remove it. Therefore, other gels were experimented with that were not made with sodium silicate. The 35-45 kDa Dextran was focused on, because it was shown to have better rheology than the PEG gel.

4.2.1) Dextran-0.5 Ml TMOS-Cabosil Gel 250 mg of 35-45 kDa dextran were completely dissolved in 2.5 ml of 0.01M acetic acid. Various amounts of a nanoparticle additive were added and mixed until uniform. The solution was then put on ice and cooled to 0 degrees Celsius. 0.5 ml of TMOS was added drop by drop and then stirred for 30 minutes. The gel was taken off the stir plate, and transferred to a 50 ml capped tube, and left to sit at room temperature overnight. Three gels were made of varying amounts of nanoparticle. The first gel did not contain any nanoparticles. The second and third gels contained 100 mg and 200 mg of Cabosil respectively.

4.2.2) Dextran Varient Dextran-1.5 Ml TMOS Gel

The next set of gels were made by varying the amount of Dextran that was added to the gel. Two gels were made using this protocol. 50 mg and 100 mg of 35-45 kDa Dextran were completely dissolved in 2.5 ml of 0.01M Acetic acid, respectively. To the solution was added 200 mg of Cabosil nanoparticles, and then solution was placed on ice. 1.5 ml of TMOS were added drop by drop to the solution and left to stir for 30 minutes. The solution was removed from the stir plate, covered in parafilm, and sat at room temperature overnight.

4.2.3) Dextran-1.5 Ml TMOS-Cabosil Gel 250 mg of 35-45 kDa Dextran were dissolved in 2.5 ml of 0.01M acetic acid. Various amounts of Cabosil nanoparticles were added depending on the gel. When the nanoparticles were homogeneously distributed, the solution was chilled to 0 degrees Celsius, and 1.5 ml of TMOS were added drop by drop. The solution was left on ice stirring for another 30 minutes before being removed from the ice and stir plate. The gel was transferred to a 50 ml capped tube and left to solidify at room temperature. Three gels were made using this protocol just varying in the amount of Cabosil added: 100 mg, 150 mg, 200 mg respectively.

These gels were found also to have nonuniform size and shape when examined under a microscope. While this particular set of gels did not have the previous problem of being hypertonic, when these gels form they release a by-product of Methanol into the gel environment. This is definitely not desirable as far as cell viability is concerned, but the majority of Methanol can be washed out of the gel.

4.3) PEG Gels

In other studies, PEG gels were found to form sphere particulates. A better regulation of the gel could be achieved if the particles were uniform.

4.3.1) PEG-TEOS 1.0 ml of TEOS and 6 ml of 0.5 M acetic acid were added to a 50 ml tube and placed on ice. This solution was sonicated at 30% for 30 minutes making sure that the top of the tube was wrapped in parafilm to prevent splashing and evaporation. This step hydrolyzed the TEOS to make it more reactive. In a microcentrifuge tube, the desired amount of Cabosil was added. To this Cabosil, 400 μl of 4-arm 2 kDa PEG were added. Due to the viscous nature of the PEG, the 400 μl were estimated based off of 400 μl of water. The Cabosil and the PEG were mixed until homogeneous. 240 μl of the hydrolyzed TEOS were added to the Cabosil and PEG solution, and mixed well. The pH, being acidic, was raised to a pH of 7 by the addition of ammonium hydroxide. The gel was left to solidify at room temperature. This particular gel when solidified formed a monolith. To turn this into a reversible gel, it was particulated. 500 μl of water were added to each microcentrifuge tube and stirred vigorously until the water was evenly dispersed throughout the gel. More water was added to form a suitable mixture. The gel and water were then centrifuged at 1500 rpm for 5 minutes and the excess water was removed. Three gels using this protocol were made all with various amounts of Cabosil: 22.5 mg, 45 mg, and 67.5 mg, respectively.

This gel is unique in that it initially forms a monolith, but is converted to a reversible through particulation. This gel gives a by-product of Ethanol, which is not conducive to cell viability. However, a lot of this ethanol can be flushed out of the gel with water.

4.3.2) PEG-DEXTRAN-TMOS 250 mg of 15-20 kDa Dextran were dissolved in 2.5 ml of 0.01M acetic acid, stirring for 30 minutes to ensure the polymer was completely dissolved. 40 mg of 20 kDa PEG were added and stirred for another 30 minutes. Various amounts of Cabosil were added depending on the gel and stirred for yet another 30 minutes. The solution was then placed on ice and chilled to 0 degrees Celsius. 1.25 ml of TMOS were added dropwise and left to stir for 30 minutes on ice. After that time, the ice was removed, but the solution was left to stir overnight. Three gels were made this way, each with various amounts of Cabosil nanoparticles: 100 mg, 150 mg, and 200 mg, respectively.

The goal of mixing PEG with Dextran was to see if a gel could be made that had the rheology of Dextran and the uniform shape that PEG was capable of. When this gel is made without nanoparticles, a monolith form. Therefore, this gel varies the amount of Cabosil added in order to see if a naturally particulated gel would form. When examined under a microscope, the gel was found to have a nonuniform size and shape. These gels had a different rheology.

4.4) Silicate Gels

Silicate gels were discovered when experimenting with different gel types. These silicate gels were not thixotropic, but they still were reversible. No chemical reaction was involved when making these gels. The gel structure was formed purely through hydrogen bonding.

4.4.1) 0.6 kDa PEG-TM40 Gel

Three gels were made all of which varied in the amount of polymer added. 0.5 ml, 1.0 ml, and 1.5 ml of 0.6 kDa PEG were the respective amounts used in making this gel. The PEG was dissolved in 1 ml of water. 400 mg of Cabosil were then mixed in to the polymer solution. Some of the gels were mixed by hand after the Cabosil was added. 1 ml of TM40 was added and mixed until uniform. More Cabosil was then added until the gel solidified. Therefore, the total amount of Cabosil varied with each gel.

4.4.2) 20 kDa PEG-TM40 Gel

Three gels were made all of which varied in the amount of polymer added. 0.5625 mg, 1.125 mg, and 1.687 mg of 20 kDa PEG were the respective amounts used in making this gel. The PEG was dissolved in 1 ml of water. 1 ml of TM40 was then added to the polymer solution. Once thoroughly mixed, Cabosil was added until the gel solidified. Each gel therefore contained different amounts of Cabosil. An initial inspection of this gel under a microscope indicated that the gel was contained of particles that varied in both size and shape. A simple cell encapsulation was done on these two gels in order to get a qualitative feel for how the gel supports cell integration. Hex and propidium iodide were used to measure cell membrane integrity. The initial experiment showed that there was high viability the day of encapsulation, indicating that the gel conditions are not so harsh as to kill cells upon initial encapsulation. In addition to the viability test, the gels containing cells were diluted with deionized water to around 7 ml and centrifuged at 800 rpm. For the 0.6 kDa PEG-TM40 gel, a pellet formed consisting mostly of cells, while the majority of the gel remained in solution. When the 20 kDa PEG-TM40 gel was centrifuged, the gel in addition to the cells pelleted to the bottom making separation of the cells from the gel impossible by this method. From this initial look at this gel, it can be concluded that the 20 kDa PEG is too large to use for the removal of cells.

5.0. Hypothetical Example. Capturing Low Abundance Normal and Tumor Cells

Various embodiments of the present invention can be used to capture low abundance normal and cancer cells (exfoliated cancer cells, circulating tumor cells, or anchorage independent cancer cells with metastatic potential) that exist in biological fluids such as serum, plasma, blood, urine, saliva, semen, and bronchial lavage fluid.

First, a small amount of functionalized silica microparticle power is added to a mononucleated cell solution obtained from whole blood. Next, silica microparticles precipitate with and encapsulate the cells in a solid, porous silica gel. The supernatant may be discarded or sent out for analysis. Then, the gel containing the encapsulated cells is incubated for 3-4 days at 37° C. in growth media. During this time the normal cells (white blood cells, etc.) in the blood die off while the circulating tumor cells survive. Then, growth media is added to gel, which contains only the encapsulated circulating tumor cells. The gel is liquefied by vortexing and the tumor cells are collected.

In various embodiments, the method can facilitate the detection of small numbers of exfoliated tumor cells and tumor-derived sub-cellular materials in biological fluids. Advantageously, various embodiments of the method 1) can capture circulating tumor cells in the blood efficiently much cheaper than existing technologies; 2) can be carried out with no additional equipment (e.g. centrifuge) and little operator training; 3) can capture any and substantially all anchorage-dependent cancer cells as opposed to the existing methods that can only capture cells that over-express EpCAM (since the isolation process can be based on different mechanotransduction behavior between normal and cancerous cells; thus various embodiments can even capture, pre-cancerous, differentiated cells that do not express EpCAM or only express EpCAM at very low levels, and cells of different phenotype); 4) can be developed into a platform to not only capture CTCs and release them on demand but utilize them for drug-screening; 5) can be flexible to be produced in any geometry or shape to be suitable for many applications; 6) can preserve the cells without the use of or with minimal use of cryoprotectant (e g dimethylsulfoxide) thereby enabling the use of the isolated cells for, for example, epigenetic research.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.
Additional Embodiments.

The present invention provides for the following exemplary embodiments, the numbering of which is not to be construed as designating levels of importance:

Embodiment 1 provides a silica-matrix encapsulated biomaterial, including a reaction product of a mixture including: a reactive silicon compound; and, a biomaterial including at least one cell including a non-cancerous mammalian cell or a cancerous mammalian cell, the at least one cell having a metabolic activity; wherein after formation of the silica-matrix encapsulated biomaterial, the at least one cell at least partially retains its metabolic activity.

Embodiment 2 provides the silica-matrix encapsulated biomaterial of Embodiment 1, wherein the reactive silicon compound includes a silanol.

Embodiment 3 provides the silica-matrix encapsulated biomaterial of any one of Embodiments 1-2, wherein the reactive silicon compound includes a silanol provided by hydrolysis of an alkoxysilane.

Embodiment 4 provides the silica-matrix encapsulated biomaterial of Embodiment 3, wherein the hydrolysis is acid-catalyzed hydrolysis.

Embodiment 5 provides the silica-matrix encapsulated biomaterial of Embodiment 3, wherein the hydrolysis is base-catalyzed hydrolysis.

Embodiment 6 provides the silica-matrix encapsulated biomaterial of any one of Embodiments 3-5, wherein alkanol byproducts from hydrolysis of the alkoxysilane have been substantially removed.

Embodiment 7 provides the silica-matrix encapsulated biomaterial of any one of Embodiments 1-6, wherein the reactive silicon compound includes a compound provided by hydrolysis of an alkoxysilane.

Embodiment 8 provides the silica-matrix encapsulated biomaterial of Embodiment 7, wherein the alkoxysilane includes a silicon compound substituted with at least one $C_{1-20}$ alkoxy group.

Embodiment 9 provides the silica-matrix encapsulated biomaterial of Embodiment 8, wherein the $C_{1-20}$ alkoxy group is further substituted with a functional group selected from the group consisting of H, hydroxyl, $C_{1-20}$ alkoxy, $C_{1-20}$ alkyl, $C_{1-20}$ alkylthio, amino, halo, nitro, mercapto, cyano, isocyanato, $C_{1-20}$ alkyloyl, $C_{5-10}$ cycloalkyl, $C_{6-10}$ aryl, and $C_{1-10}$ heterocycle; wherein the aryl or heterocycle is further substituted with a functional group selected from the group consisting of H, hydroxyl, $C_{1-20}$ alkoxy, $C_{1-20}$ alkyl, $C_{1-20}$ alkylthio, amino, halo, nitro, mercapto, cyano, and isocyanato.

Embodiment 10 provides the silica-matrix encapsulated biomaterial of any one of Embodiments 8-9, wherein the alkoxysilane includes a silicon compound substituted with four independently selected $C_{1-20}$ alkoxy groups.

Embodiment 11 provides the silica-matrix encapsulated biomaterial of Embodiment 10, wherein the four independently selected $C_{1-20}$ alkoxy groups are the same.

Embodiment 12 provides the silica-matrix encapsulated biomaterial of any one of Embodiments 1-11, wherein the reactive silicon compound includes a compound provided by hydrolysis of at least one of tetramethylorthosilicate (TMOS), tetraethylorthosilicate (TEOS), tetrakis(2-hydroxyethyl)orthosilicate (THEOS), methyldiethoxysilane (MDES), 3-(glycidoxypropyl)triethoxysilane (GPTMS), 3-(trimethyoxysilyl)propylacrylate (TMSPA), N-(3-triethoxysilylpropyl)pyrrole (TESPP), vinyltriethyoxysilane (VTES), methacryloxypropyltriethoxysilane (TESPM), diglycerylsilane (DGS), methyltriethoxysilane (MTMOS), trimethylmethoxysilane (TMMS), ethyltriethoxysilane (TEES), n-propyltriethoxysilane (TEPS), n-butyltriethyoxysilane (TEBS), 3-aminopropyltriethoxysilane (APTS), 2-(2,4-dinitrophenylamino)propyltriethoxysilane, mercaptopropyltriethoxysilane (TEPMS), 2-(3-aminoethylamino) propyltriethoxysilane, isocyanatopropyltriethoxysilane, hydroxyl-terminated polydimethylsiloxane, triethoxysilyl-terminated polydimethylsiloxane, methyltriethoxysilane (MTES), and triethoxysilyl-terminated poly(oxypropylene).

Embodiment 13 provides the silica-matrix encapsulated biomaterial of any one of Embodiments 1-12, wherein the reactive silicon compound includes a compound provided by treatment of a silicate with acid.

Embodiment 14 provides the silica-matrix encapsulated biomaterial of any one of Embodiments 1-13, wherein the reactive silicon compound includes a compound provided by treatment of an aqueous solution of a silicate salt with acid.

Embodiment 15 provides the silica-matrix encapsulated biomaterial of Embodiment 14, wherein the aqueous solution of the silicate salt is formed by treatment of silica with a base.

Embodiment 16 provides the silica-matrix encapsulated biomaterial of any one of Embodiments 1-15, wherein the reactive silicon compound includes a compound provided by the treatment of colloidal silica with acid.

Embodiment 17 provides the silica-matrix encapsulated biomaterial of any one of Embodiments 1-16, wherein the reactive silicon compound includes a silanol provided by treatment with acid of an aqueous sodium silicate solution or an aqueous potassium silicate solution.

Embodiment 18 provides the silica-matrix encapsulated biomaterial of any one of Embodiments 1-17, further including water.

Embodiment 19 provides the silica-matrix encapsulated biomaterial of any one of Embodiments 1-18, further including an organic precursor.

Embodiment 20 provides the silica-matrix encapsulated biomaterial of Embodiment 19, wherein the organic precursor includes at least one of a synthetic polymer or monomer, a natural polymer or monomer, and an amino acid.

Embodiment 21 provides the silica-matrix encapsulated biomaterial of any one of Embodiments 19-20, wherein the organic precursor includes a hydroxyl-terminated polymer.

Embodiment 22 provides the silica-matrix encapsulated biomaterial of any one of Embodiments 19-21, wherein the organic precursor includes a polymer terminating in at least one of hydroxyl, amino, vinyl, and carboxylic acid.

Embodiment 23 provides the silica-matrix encapsulated biomaterial of any one of Embodiments 19-22, wherein the organic precursor includes a hydroxyl-terminated poly(alkyleneoxide) polymer, wherein each alkyleneoxide unit is individually a $C_{1-10}$ alkylene oxide, wherein the polymer is at least one of linear and branched.

Embodiment 24 provides the silica-matrix encapsulated biomaterial of any one of Embodiments 19-23, wherein the organic precursor includes at least one of a saccharide and polysaccharide.

Embodiment 25 provides the silica-matrix encapsulated biomaterial of any one of Embodiments 19-24, wherein the organic precursor includes trehalose.

Embodiment 26 provides the silica-matrix encapsulated biomaterial of any one of Embodiments 19-25, wherein the organic precursor includes at least one of polyethylene glycol (PEG), polyvinyl alcohol (PVA), polyacrylic acid (HPAA), polymethyl methacrylate (PMMA), poly(2-hydroxyethyl methacrylate) (PHEMA), Pluronic™ F127 (ethylene oxide polypropylene oxide block copolymer), and Pluronic™ P123 (ethylene oxide propylene oxide ethylene oxide triblock copolymer).

Embodiment 27 provides the silica-matrix encapsulated biomaterial of any one of Embodiments 19-26, wherein the organic precursor includes at least one of a peptide, amino acid, alginate, gelatin, chitosan, sucrose, trehalose, dextrin, casein, bovine serum, and collagen.

Embodiment 28 provides the silica-matrix encapsulated biomaterial of any one of Embodiments 1-27, further including silica.

Embodiment 29 provides the silica-matrix encapsulated biomaterial of any one of Embodiments 1-28, further including silica nanoparticles.

Embodiment 30 provides the silica-matrix encapsulated biomaterial of any one of Embodiments 1-29, further including colloidal silica.

Embodiment 31 provides the silica-matrix encapsulated biomaterial of any one of Embodiments 1-30, further including colloidal silica nanoparticles.

Embodiment 32 provides the silica-matrix encapsulated biomaterial of any one of Embodiments 1-31, wherein the pH of the composition is between about 5 and about 10.

Embodiment 33 provides the silica-matrix encapsulated biomaterial of any one of Embodiments 1-32, wherein the pH of the composition is adjusted sufficiently to allow formation of the silica-encapsulated biomaterial within about 5 min to about 24 hours.

Embodiment 34 provides the silica-matrix encapsulated biomaterial of any one of Embodiments 1-33, wherein the pH of the composition is adjusted sufficiently to allow gelation of the composition within about 5 min to about 24 hours.

Embodiment 35 provides the silica-matrix encapsulated biomaterial of any one of Embodiments 1-34, wherein the silica-matrix includes a thixotropic silica gel.

Embodiment 36 provides the silica-matrix encapsulated biomaterial of any one of Embodiments 1-35, wherein before encapsulation the biomaterial includes at least one living cancerous mamallian cell and at least one living non-cancerous mammalian cell, wherein after formation of the silica-matrix encapsulated biomaterial, the at least one non-cancerous cell dies, and the at least one cancerous cell survives.

Embodiment 37 provides the silica-matrix encapsulated biomaterial of Embodiment 36, wherein the biomaterial includes a plurality of cancerous cells, and a plurality of non-cancerous cells.

Embodiment 38 provides the silica-matrix encapsulated biomaterial of any one of Embodiments 36-37, wherein after encapsulation of the biomaterial with the silica-matrix, the non-cancerous cells die faster than the cancerous cells.

Embodiment 39 provides the silica-matrix encapsulated biomaterial of any one of Embodiments 36-38, wherein the non-cancerous cells die at a rate of about 2 times faster than the rate of death of the cancerous cells.

Embodiment 40 provides the silica-matrix encapsulated biomaterial of any one of Embodiments 36-39, wherein after encapsulation of the biomaterial with the silica-matrix, some of the cancerous cells remain living after substantially all of the non-cancerous cells have died.

Embodiment 41 provides the silica-matrix encapsulated biomaterial of any one of Embodiments 36-40, wherein at about 12 hours after encapsulation of the biomaterial with the silica-matrix, less than 40% of the non-cancerous cells have died, and greater than about 60% of the cancerous cells have died.

Embodiment 42 provides the silica-matrix encapsulated biomaterial of any one of Embodiments 36-41, wherein at about 24 hours after encapsulation of the biomaterial with the silica-matrix, less than 40% of the non-cancerous cells have died, and greater than about 60% of the cancerous cells have died.

Embodiment 43 provides a method of using the composition of any one of Embodiments 1-42 to generate cancerous cells substantially free of non-cancerous cells.

Embodiment 44 provides the silica-matrix encapsulated biomaterial of any one of claims 1-35, wherein before encapsulation the biomaterial comprises at least one living first cancerous mammalian cell and at least one living second cancerous mammalian cell, the first living cancerous mammalian cell and the second living cancerous mammalian cell being having different phenotypes, wherein after formation of the silica-matrix encapsulated biomaterial, the at least one first cancerous cell dies, and the at least one second cancerous cell survives.

Embodiment 45 provides a method for formation of a silica-matrix encapsulated biomaterial, including: forming a silica-matrix encapsulated biomaterial, including the reaction product of a mixture including a reactive silicon compound; and, a biomaterial including at least one cell including a non-cancerous mammalian cell or a cancerous mammalian cell, the at least one cell having a metabolic activity; wherein forming the silica-matrix encapsulated biomaterial, the at least one cell at least partially retains its metabolic activity.

Embodiment 46 provides a method of generating cancerous cells substantially free of non-cancerous cells, including: forming a silica-matrix encapsulated biomaterial, including a reaction product of a mixture including a reactive silicon compound; and, a biomaterial including at least one living cancerous mammalian cell and at least one living non-cancerous mammalian cell; wherein after forming the silica-matrix encapsulated biomaterial, the at least one non-cancerous cell dies, and the at least one cancerous cell survives; and removing the at least one cancerous cell from the silica-matrix.

Embodiment 47 provides a method of selectively purifying cancerous cells, including: forming a silica-matrix encapsulated biomaterial, including a reaction product of a mixture including a reactive silicon compound; and, a biomaterial including at least one living cancerous mammalian cell and at least one living non-cancerous mammalian cell; wherein after forming the silica-matrix encapsulated biomaterial, the at least one non-cancerous cell dies, and the at least one cancerous cell survives; and removing the at least one cancerous cell from the silica-matrix.

Embodiment 48 provides a method of selectively purifying cancerous cells, including: forming a silica-matrix encapsulated biomaterial, comprising a reaction product of a mixture comprising a reactive silicon compound; and, a biomaterial comprising at least one first living cancerous mammalian cell and at least one second living cancerous mammalian cell, the first living cancerous mammalian cell and the second living cancerous mammalian cell being having different phenotypes; wherein after forming the silica-matrix encapsulated biomaterial, the at least one first cancerous cell dies, and the at least one second cancerous cell survives; and removing the at least one second cancerous cell from the silica-matrix.

Embodiment 49 provides the apparatus or method of any one or any combination of Embodiments 1-48 optionally configured such that all elements or options recited are available to use or select from.

We claim:
1. A method of selectively purifying cancerous cells, comprising:
   obtaining or providing a mixture comprising:
      a reactive silicon compound; and,
      a biomaterial comprising at least one first living cancerous mammalian cell and at least one second living cancerous mammalian cell, the second living cancerous mammalian cell having a metabolic activity, the first living cancerous mammalian cell and the second living cancerous mammalian cell having different phenotypes;

forming a reaction product of the mixture comprising a silica-matrix encapsulated biomaterial, wherein the second cancerous mammalian cell at least partially retains metabolic activity within the silica-matrix such that the first living cancerous mammalian cell dies at a faster rate than the second living cancerous mammalian cell; and removing the second cancerous mammalian cell from the silica-matrix after a period of time in which the second cancerous mammalian cell remains living after the first cancerous cell dies.

2. The method of claim 1, wherein the reactive silicon compound comprises a silanol.

3. The method of claim 1, wherein the reactive silicon compound comprises a compound provided by hydrolysis of an alkoxysilane and/or a silica nanoparticle.

4. The method of claim 3, wherein the alkoxysilane comprises a silicon compound substituted with at least one substituted or unsubstituted $C_{1-20}$ alkoxy group.

5. The method of claim 4, wherein the alkoxysilane comprises a silicon compound substituted with four independently selected substituted or unsubstituted $C_{1-20}$ alkoxy groups.

6. The method of claim 1, wherein the reactive silicon compound comprises a compound provided by hydrolysis of at least one of tetramethylorthosilicate (TMOS), tetraethylorthosilicate (TEOS), tetrakis(2-hydroxyethyl)orthosilicate (THEOS), methyldiethoxysilane (MDES), 3-(glycidoxypropyl)triethoxysilane (GPTMS), 3-(trimethyoxysilyl)propylacrylate (TMSPA), N-(3-triethoxysilylpropyl)pyrrole (TESPP), vinyltriethyoxysilane (VTES), methacryloxypropyltriethoxysilane (TESPM), diglycerylsilane (DGS), methyltriethoxysilane (MTMOS), trimethylmethoxysilane (TMMS), ethyltriethoxysilane (TEES), n-propyltriethoxysilane (TEPS), n-butyltriethyoxysilane (TEBS), 3-aminopropyltriethoxysilane (APTS), 2-(2,4-dinitrophenylamino)propyltriethoxysilane, mercaptopropyltriethoxysilane (TEPMS), 2-(3-aminoethylamino)propyltriethoxysilane, isocyanatopropyltriethoxysilane, hydroxyl-terminated polydimethylsiloxane, triethoxysilyl-terminated polydimethylsiloxane, methyltriethoxysilane (MTES), and triethoxysilyl-terminated poly(oxypropylene).

7. The method of claim 6, wherein the reactive silicon compound comprises a compound provided by hydrolysis of at least one of tetramethylorthosilicate (TMOS), tetraethylorthosilicate (TEOS), and tetrakis(2-hydroxyethyl)orthosilicate (THEOS).

8. The method of claim 7, wherein the reactive silicon compound comprises a compound provided by hydrolysis of tetramethylorthosilicate (TMOS).

9. The method of claim 7, wherein the reactive silicon compound comprises a compound provided by hydrolysis of tetraethylorthosilicate (TEOS).

10. The method of claim 7, wherein the reactive silicon compound comprises a compound provided by hydrolysis of tetrakis(2-hydroxyethyl)orthosilicate (THEOS).

11. The method of claim 1, wherein the reactive silicon compound comprises a compound provided by treatment of a silicate with acid.

12. The method of claim 1, further comprising an organic precursor.

13. The method of claim 12, wherein the organic precursor comprises polyethylene glycol.

14. The method of claim 13, wherein the mixture further comprises at least one of silica, silica nanoparticles, colloidal silica, and colloidal silica nanoparticles.

* * * * *